US009642998B2

(12) United States Patent
Nordsiek et al.

(10) Patent No.: US 9,642,998 B2
(45) Date of Patent: May 9, 2017

(54) PUMP SYSTEMS AND METHODS FOR STORING AND DISPENSING A PLURALITY OF PRECISELY MEASURED UNIT-DOSES OF IMIQUIMOD CREAM

(71) Applicant: MEDICIS PHARMACEUTICAL CORPORATION, Scottsdale, AZ (US)

(72) Inventors: Michael T. Nordsiek, Wayne, PA (US); Kodumudi S. Balaji, Lansdale, PA (US)

(73) Assignee: MEDICIS PHARMACEUTICAL CORPORATION, Scottsdale, AZ (US)

( * ) Notice: Subject to any disclaimer, the term of this patent is extended or adjusted under 35 U.S.C. 154(b) by 0 days.

(21) Appl. No.: 14/641,089

(22) Filed: Mar. 6, 2015

(65) Prior Publication Data
US 2015/0314115 A1 Nov. 5, 2015

Related U.S. Application Data

(62) Division of application No. 12/875,787, filed on Sep. 3, 2010, now Pat. No. 9,072,876.

(60) Provisional application No. 61/402,251, filed on Aug. 26, 2010, provisional application No. 61/377,336, filed on Aug. 26, 2010, provisional application No. 61/402,052, filed on Aug. 23, 2010, provisional application No. 61/376,154, filed on Aug. 23, 2010, provisional application No. 61/401,997, filed on Aug. 20, 2010, provisional application No. 61/375,580, filed on Aug. 20, 2010, provisional application No. 61/371,137, filed on Aug. 5, 2010.

(51) Int. Cl.
| *A61K 31/00* | (2006.01) |
| *A61M 35/00* | (2006.01) |
| *B05B 11/00* | (2006.01) |
| *A61K 9/00* | (2006.01) |
| *A61K 9/06* | (2006.01) |
| *A61K 31/4745* | (2006.01) |
| *A61K 47/10* | (2017.01) |

(52) U.S. Cl.
CPC ......... *A61M 35/003* (2013.01); *A61K 9/0014* (2013.01); *A61K 9/0031* (2013.01); *A61K 9/0034* (2013.01); *A61K 9/06* (2013.01); *A61K 31/4745* (2013.01); *A61K 47/10* (2013.01); *B05B 11/0024* (2013.01); *B05B 11/0037* (2013.01); *B05B 11/0048* (2013.01); *B05B 11/3001* (2013.01); *B05B 11/3042* (2013.01); *B05B 11/3047* (2013.01)

(58) Field of Classification Search
None
See application file for complete search history.

(56) References Cited

U.S. PATENT DOCUMENTS

| 4,689,338 | A | 8/1987 | Gerster | |
| 6,991,139 | B2 | 1/2006 | Garcia et al. | |
| 7,654,418 | B2 | 2/2010 | Law et al. | |
| 2002/0020715 | A1* | 2/2002 | Gueret | B05B 7/2462 222/153.11 |
| 2005/0267144 | A1* | 12/2005 | Mandrea | A61K 31/137 514/292 |
| 2006/0043118 | A1 | 3/2006 | Law et al. | |
| 2006/0255071 | A1 | 11/2006 | Behar et al. | |
| 2007/0251910 | A1* | 11/2007 | Mastin | B65D 51/2807 215/228 |
| 2007/0264317 | A1 | 11/2007 | Yosha et al. | |
| 2008/0119572 | A1 | 5/2008 | Owens et al. | |
| 2009/0232755 | A1* | 9/2009 | Baumann | A61K 8/365 424/59 |
| 2009/0236374 | A1 | 9/2009 | Pardes et al. | |

(Continued)

FOREIGN PATENT DOCUMENTS

| CA | 1271458 | 7/1990 |
| CA | 2649893 | 8/2010 |
| EP | 1629900 A2 | 3/2006 |

(Continued)

OTHER PUBLICATIONS

Arany, I. et al., "Enhancement of the innate and cellular immune response in patients with genital warts treated with topical imiquimod cream 5%," *Antiviral Res*, 1999, vol. 43:55-63.
Berman, B. et al., "Actinic keratosis: sequelae and treatments," Recommendations from a consensus panel, *J Fam Pract*, May 2006, vol. 55(5)(suppl):1-8.
Bernstein, DI et al., Effects of the immunomodulating agent R-837 on acute and latent herpes simplex virus type 2 infections, *Antimicro Agents and Chemo*, 1989, 33(9):1511-1515.

(Continued)

*Primary Examiner* — Robert A Wax
*Assistant Examiner* — Quanglong Truong
(74) *Attorney, Agent, or Firm* — Kilpatrick Townsend & Stockton LLP

(57) ABSTRACT

The present invention is directed to airless storage and dispensing systems that include a pump or dispensing package pre-filled with a topical semi-solid imiquimod pharmaceutical formulation ("pump systems") and methods for storing and dispensing from the pump systems a plurality of precisely measured and uniform unit doses of a topical semi-solid imiquimod pharmaceutical formulation, and more particularly to pump systems, pre-filled with a topical imiquimod pharmaceutical cream and methods for delivering multiple precisely measured unit doses of a topical imiquimod pharmaceutical cream, and methods for using a controlled delivery pump system to store and dispense a plurality of consistent and precisely measured unit doses of a topical imiquimod pharmaceutical cream for use in topically treating a dermal and mucosal-associated condition, such as, external genital warts and/or perianal warts (EGWs), actinic keratosis or actinic keratoses (AK or AKs) and superficial basal cell carcinoma (sBCC).

25 Claims, 11 Drawing Sheets

(56) References Cited

U.S. PATENT DOCUMENTS

| | | | |
|---|---|---|---|
| 2011/0021555 A1 | 1/2011 | Nordsiek et al. | |
| 2011/0207766 A1 | 8/2011 | Nordsiek et al. | |

FOREIGN PATENT DOCUMENTS

| | | | |
|---|---|---|---|
| WO | 2010/080345 A1 | 7/2010 | |
| WO | 2011/008324 A1 | 1/2011 | |
| WO | 2012/019158 A2 | 9/2012 | |

OTHER PUBLICATIONS

Bernstein, DI et al., "Effects of therapy with an immunomodulator (Imiquimod, R-837) alone and with acyclovir on genital HSV-2 infection in guinea pigs when begun after lesion development," *Antiviral Res*, 1993, 20:45-55.

Dahl, MV, "Imiquimod: An immune response modifier," *J Am Acad Dermatol*, 2000, 43(1):S1-5.

Edwards, L., "Imiquimod in clinical practice," *J Am Acad Dermatol*, 2000, 43(1):S12-17.

Edwards, L., "Self-administered topical 5% imiquimod cream for external anogenital warts," *Arch Dermatol*, 1998, 134:25-30.

Einspahr, JG et al., Reproducibility and expression of skin biomarkers in sun-damaged skin and actinic keratosis, *Cancer Epidemiol Biomarkers Pres*, Oct. 2006, 15(10):1841-1848.

Fact Sheet: "Human Papillomaviruses and Cancer: Questions and Answers," National Cancer Institute, pp. 1-11, www.cancer.gov/cancertopics/factsheet/RishkHPV (Reviewed Feb. 14, 2008).

Gaspari, AA et al., "Immunotherapy of basal cell carcinoma: evolving approached," *Derm Surg*, 2003, 29(10): 1027-1034.

Gearhart, PA et al., "Human papillomavirus," emedicine, pp. 1-33, http://emedicine.medscape.com/article/219110 (Updated Mar. 8, 2010).

Gollnick H. et al., "Safety and efficacy of imiquimod 5% cream in the treatment of penile genital warts in uncircumcised men when applied three times weekly of once per day," *Int J STD and AIDS*, 2001, 12:22-28.

Harrison CJ et al., "Post therapy suppression of genital herpes simplex virus (HSV) recurrences and enhancement of HSV-specific T-cell memory by imiquimod in guinea pigs," *Antimicro Agents and Chemo*, 1994, 38(9):2059-2064.

Kende, M. et al., "Treatment of experimental viral infections with immunomodulators," *Adv Biosci*, 1988, 68:51-63.

Koutsky, L., "Epidemiology of genital human papillomavirus infection," *Am J Med*, 1997, 102(5A):3-8.

Koutsky, L., "Epidemiology of human papillomavirus infection," *Epidemiol Rev*, 1998, 10:122-163.

Kreuter, A., et al., "5% Imiquimod suppositories decrease the DNA load of intra-anal HPV types 6 and 11 in HIV-infected men after surgical ablation of condylomata acuminate [letter]," *Arch Dermatol*, Feb. 2006, 142(2):243-244.

Lebwohl, M et al., "Imiquimod 5% cream for the treatment of actinic keratosis: results from two phase III, randomized, double-blind, parallel group, vehicle-controlled trials," *J Am Acad Dermatol*, May 2004, 50(5):714-721.

Lyttle, PH, Surveillance report: disease trends at New Zealand sexually transmitted disease clinics 1977-1993, *Genitourin Med*, 1994, 70:329-335.

Mayeaux, EJ et al., Noncervical human papillomavirus genital infections, *Am Fam Physician*, 1995, 52:1137-1146.

Miller, RL et al., "Imiquimod cytokine induction and antiviral activity," *Intl Antiviral News*, 1995, 3(7):111-113.

Miller, RL et al., Imiquimod applied topically: a novel immune response modifier and new class of drug, *Int J Immunopharm*, 1999, 21:1-14.

Phelps, W. et al., "Antiviral therapy for human papillomaviruses: rationale and prospects," *Ann Intern Med*, 1995, 123:368-382.

Quatresooz, P. et al., "Crossroads between actinic keratosis and squamous cell carcinoma, and novel pharmacological issues," *Eur J Dermatol.*, Jan.-Feb. 2008, 18(1):6-10.

Sauder, DN., "Immunomodulatory and pharmacologic properties of imiquimods," *J Am Acad Dermatol*, 2000, 43(1):S6-11.

Shah KV, Howley PM, "Papillomaviruses," In: Fields BN, Knipe DM, ed. *Fields Virology*, 1990, 2nd ed. New York, NY: Raven Press, (2)59:1651-1666.

Stockfleth E. et al., "Guidelines for the management of actinic keratosis," *Eur J Dermatol*, Nov.-Dec. 2006, 16(6):599-606.

Testerman, TL et al., "Cytokine induction by the immunomodulators imiquimod and S-27609," *J Leuk Biol*, 1995, 58:365-372.

Torres, A. et al., "Microarray analysis of aberrant gene expression in actinic keratosis: effect of the Toll-like receptor-7 agonist imiquimod," *Br J Dermatol*, Dec. 2007, 157(6):1132-47. Epub Oct. 28, 2007.

Tyring, SK et al., "A randomized, controlled, molecular study of condylomata acuminate clearance during treatment with imiquimod," *J Infect Dis*, 1998, 178(August):551-555.

Tyring, SK, "Immune-response modifiers: A new paradigm in the treatment of human papillomavirus," *Curr Ther Res*, 2000, 60(9):584-596.

Vatve, M. et al., "Management of field change in actinic keratosis," *Br J. Dermatol*, Dec. 2007, 157(S2):21-24.

Weeks, CE et al., "Induction of interferon and other cytokines by imiquimod and its hydroxylated metabolite R-842 in human blood cells in vitro," *J Interferon Res*, 1994, 14:81-85.

Office Action issued in Canadian Patent Application No. 2713777, dated May 28, 2013, 5 pages.

First Examination Report dated Oct. 15, 2013, from corresponding New Zealand Application No. 607844; Owner: Medicis Pharmaceutical Corporation; 2 pages.

Office Action dated Dec. 5, 2013 in corresponding Canadian Application No. 2,713,777; Owner: Medicis Pharmaceutical Corporation; 5 pages.

Extended European Search Report dated Jul. 8, 2014, from corresponding European Application No. 11815401.2; Owner: Medicis Pharmaceutical Corporation; 9 pages.

Office Action mailed Aug. 14, 2014, from U.S. Appl. No. 12/875,787 (14 pages).

Notice of Allowance mailed Dec. 23, 2014, from U.S. Appl. No. 12/875,787 (13 pages).

Documentary Report and Search Report dated Dec. 26, 2014, in corresponding Georgian Application No. AP 2011013020; 3 pages.

Further Examination Report dated Feb. 10, 2015, from corresponding New Zealand Application No. 607844; Owner: Medicis Pharmaceutical Corporation; 3 pages.

Patent Examination Report No. 1 dated Feb. 25, 2015, from corresponding Australian Application No. 2011285567 (3 pages).

\* cited by examiner

Subject Accountability (External Genital Warts)

PUMP SYSTEMS AND METHODS FOR STORING AND DISPENSING A PLURALITY OF PRECISELY MEASURED UNIT-DOSES OF IMIQUIMOD CREAM

CROSS REFERENCE TO RELATED APPLICATIONS

This application claims priority benefit under 35 U.S.C. §119(e) to (1) U.S. Provisional Application No. 61/402,251, which was filed on Aug. 26, 2010 via U.S. Express Mail No. EG463456778US and is entitled "Pump Systems and Methods for Storing and Dispensing A Plurality of Precisely Measured Unit Doses of Imiquimod Cream", (2) U.S. Provisional Application No. 61/377,336, which was filed on Aug. 26, 2010 and is entitled "Pump Systems and Methods for Storing and Dispensing A Plurality of Precisely Measured Unit Doses of Imiquimod Cream", (3) U.S. Provisional Application No. 61/402,052, which was filed on Aug. 23, 2010 via U.S. Express Mail No. EG463456733US and is entitled "Pump Systems and Methods for Storing and Dispensing A Plurality of Precisely Measured Unit Doses of Imiquimod Cream", (4) U.S. Provisional Application No. 61/376,154, which was filed on Aug. 23, 2010 and is entitled "Pump Systems and Methods for Storing and Dispensing a Plurality of Precisely Measured Unit-Doses of Imiquimod Cream", (5) U.S. Provisional Application No. 61/401,997, which was filed on Aug. 20, 2010 via U.S. Express Mail No. EG463456781US and is entitled "Pump Systems and Methods for Storing and Reproducibly Dispensing Precisely Measured Unit Doses of Imiquimod Cream", (6) U.S. Provisional Application No. 61/375,580, which was filed on Aug. 20, 2010 and is entitled "Pump Systems and Methods for Storing and Reproducibly Dispensing Precisely Measured Unit Doses of Imiquimod Cream", and (7) U.S. Provisional Application No. 61/371,137, which was filed on Aug. 5, 2010 and is entitled "Systems and Methods for Storing and Dispensing Unit Doses of Imiquimod Cream", each of which, including its respective content, is incorporated herein by reference in its entirety.

FIELD OF THE INVENTION

The subject invention relates to unique storage and dispensing systems that include a pump or dispensing package pre-filled with a topical semi-solid imiquimod pharmaceutical formulation ("pump systems") and methods for storing and dispensing a plurality of precisely measured unit doses of a topical semi-solid imiquimod pharmaceutical formulation, and more particularly to pump systems pre-filled with an imiquimod pharmaceutical cream and methods for delivering multiple precisely measured unit doses of an imiquimod pharmaceutical cream, and methods for using a controlled delivery pump to store and dispense a plurality of precisely measured unit doses of a topical semi-solid imiquimod pharmaceutical formulation for use in treating a dermal and/or mucosal-associated condition, such as, external genital warts and/or perianal warts (EGWs), actinic keratosis or actinic keratoses (AK or AKs) and superficial basal cell carcinoma (sBCC).

BACKGROUND

External genital warts and perianal warts, i.e., condylomata acuminate, are caused by infection with human papilloma virus (HPV), the most common sexually transmitted virus in the Western world. See, e.g., Lyttle P H.: Surveillance report: disease trends at New Zealand sexually transmitted disease clinics 1977-1993. *Genitourin Med.*, 70:329-335 (1994); Mayeaux E J, Harper M B, Barksdale W, Pope J B.: Noncervical human papillomavirus genital infections. *Am Fam Physician.*, 52:1137-1146 (1995); and Shah K V, Howley P M.: Papillomaviruses. In: Fields, B N, Knipe D M, ed *Fields Virology.* 2nd ed. New York, N.Y.: Raven Press; (2)59:1651-1666 (1990). Approximately 1% of the sexually active population between 15 and 49 years of age in the United States is estimated to have external genital warts. See, e.g., Koutsky L.: Epidemiology of human papillomavirus infection. *Epidemiol Rev.*, 10:122-163 (1998); and Koutsky L.: Epidemiology of genital human papillomavirus infection. *Am J Med.*, 102(5A):3-8 (1997). Most external genital warts are associated with HPV types 6 and 11. See, e.g., Phelps W, Alexander K A.: Antiviral therapy for human papillomaviruses: rationale and prospects. *Ann Intern Med.*, 123:368-382 (1995). HPV types 6 and 11 are typically labeled as low risk because infection with these types has low oncogenic potential and usually results in the formation of condylomata and low-grade precancerous lesions. See, e.g., Gearhart, P. A. and Randall, T. C.: Human Papillomavirus, emedicine, pages 1-33, http://emedicine.medscape-.com/article/219110 (Updated: Mar. 8, 2010); and Fact Sheet: *Human Papillomaviruses and Cancer: Questions and Answers*, National Cancer Institute, pages. 1-11, www.cancer.gov/cancertopics/factsheet/RiskHPV (Reviewed Feb. 14, 2008).

Specific antiviral therapy for the treatment of external genital warts and perianal warts is lacking, but drug and other therapies have been used. Ablative treatment modalities include procedures such as surgical excision, laser therapy, and cryotherapy. Other approaches include topical treatments, such as acetic acid, podophylline, podophyllotoxin, and 5-fluorouracil, which are cytodestructive, and sinecatechins, whose mechanism of action is unknown. Each of these therapies have disadvantages such as inconvenient regimens, pain, burning associated with the therapy, scarring, itching and/or high recurrence rates.

On Feb. 27, 1997, imiquimod 5% cream was approved for the very first time by the U.S. Food and Drug Administration (FDA) for the treatment of external genital and perianal warts, i.e., condyloma acuminate (EGW or EGWs), in patients 12 years or older. See Aldara® Package Insert (Label) Revised: March 2007 (Attachment VIII). Imiquimod, an immune response modifier that stimulates the innate and adaptive immune response, has been demonstrated to be an effective and safe treatment for external genital warts and perianal warts. Stimulation of the immune response has been shown to decrease HPV viral load, Kreuter A, Brockmeyer N H, Weissenborn S J, et al.: 5% Imiquimod suppositories decrease the DNA load of intra-anal HPV types 6 and 11 in HIV-infected men after surgical ablation of condylomata acuminata [letter]. *Arch Dermatol.*; 142(2):243-4 (February, 2006), and thus may decrease the recurrence rate of visible warts, although observed rates after treatments do vary.

In the treatment of EGWs diagnosed in adults, the approved dosing regimen for Aldara® (imiquimod) 5% cream is 3 times per week, for up to 16 weeks of treatment. Aldara® (imiquimod) 5% cream should be applied 3 times per week to external genital/perianal warts. Aldara® (imiquimod) 5% cream treatment should continue until there is total clearance of the genital/perianal warts or for a maximum of 16 weeks. Examples of 3 times per week application schedules are: Monday, Wednesday, Friday or Tuesday, Thursday, Saturday. Aldara® (imiquimod) 5% cream should be applied prior to normal sleeping hours and left on the skin for 6-10 hours, after which time the cream should be removed by washing the area with mild soap and water. The prescriber should demonstrate the proper application technique to maximize the benefit of Aldara® (imiquimod) 5% cream therapy. It is recommended that patients wash their hands before and after applying Aldara® (imiquimod) 5% cream.

A study in 22 patients with genital/perianal warts comparing Aldara® (imiquimod) 5% cream and vehicle shows that Aldara® (imiquimod) 5% cream induces mRNA encoding cytokines including interferon-α at the treatment site. In addition, HPVL1 mRNA and HPV DNA are significantly decreased following treatment. However, the clinical relevance of these findings is unknown.

A thin layer of Aldara® (imiquimod) 5% cream should be applied to the wart area and rubbed in until the cream is no longer visible. The application site should not be occluded. Following the treatment period, the Aldara® (imiquimod) 5% cream should be removed by washing the treated area with mild soap and water. Local skin reactions at the treatment site are common. A rest period of several days may be taken if required by the patient's discomfort or severity caused by the treatment-related local skin reactions. Treatment may resume once the reactions subside. Non-occlusive dressings such as cotton gauze or cotton underwear may be used in the management of skin reactions. Aldara® (imiquimod) 5% cream is currently packaged in single-use packets or sachets which contain sufficient cream to cover a wart area of up to about 20 cm². Use of excessive amounts of cream and passive transfer of the cream should be avoided.

Actinic keratosis is a precancerous (premalignant) skin disorder caused by or associated with chronic exposure to radiant energy, such as sunlight. Actinic keratosis lesions (AKs) are small, red, rough spots or lesions occurring on sun exposed areas of the skin. Actinic keratosis lesions possess many of the same cellular changes observed in a skin cancer called squamous cell carcinoma (SCC). Research shows that a mutated version of the p53 gene is found in sun-damaged cells in the body and is present in more than about 90% of people who have AKs and SCC. Although most actinic keratosis lesions do not actually become cancerous, some AKs can become malignant.

It is believed that actinic keratosis develops in skin cells called "keratinocytes", which are the cells that constitute about 90% of the epidermis, the outermost layer of skin. Chronic sun exposure, over time, generates mutations in these cells and causes the cells to change in size, shape, the way they are organized, and the way they behave. In addition, the cellular damage can even extend to the dermis, the layer of skin beneath the epidermis.

Actinic keratosis lesions generally measure in size between about 2 to about 6 millimeters in diameter. AK lesions can range in color from skin-toned to reddish and often have a white scale on top. On occasion, AK lesions will form into the shape of animal horns. When this occurs, the AKs are known as "cutaneous horns."

People who are at higher risk for developing actinic keratosis tend to be fair-skinned and spend significant time outdoors, e.g., at work or at play, over the course of many years. AKs usually develop on those areas of the body that have been constantly exposed to the sun for years. Additionally, the skin often becomes wrinkled, mottled, and discolored from chronic sun exposure. Common locations for AKs include the face, ears, lips, balding scalp, back of the neck, upper chest, the tops of the hands and forearms. When AKs develop on the lips, the condition is known as actinic cheilitis. Actinic cheilitis can be characterized by a diffuse scaling on the lower lip that cracks and dries. In some cases, the lips will have a whitish discoloration on the thickened lip.

Actinic keratosis is generally more common after age 40, because actinic keratosis takes years to develop. However, even younger adults may develop actinic keratosis when living in geographic areas that are exposed to high-intensity sunlight year round, such as Florida and Southern California.

Actinic keratosis has become a significant health care issue in the United States of America. It is estimated that over 20 million Americans suffer from actinic keratoses, and that that number continues to grow. In fact, actinic keratosis is so common today that treatment for actinic keratosis ranks as one of the most frequent reasons people consult dermatologists.

Once an immunocompetent adult is diagnosed with clinically visible AKs, a variety of treatment options are currently available. These options include physically removing the AKs by (1) freezing them with liquid nitrogen, (2) using a laser to burn the AKs, (3) scraping the AKs off, or (4) using topical creams to treat the AKs. One such cream that can be applied to the skin for the treatment of AKs is Aldara® (imiquimod) 5% cream.

On Mar. 2, 2004, Aldara® (imiquimod) 5% cream was approved by the FDA, under section 505(b) of the Federal Food, Drug and Cosmetic Act, for the treatment of clinically typical, nonhyperkeratotic, nonhypertrophic actinic keratoses on the face and scalp in immunocompetent adults. Imiquimod, an immune response modifier that stimulates the innate and adaptive immune response, has been demonstrated to be an effective and safe treatment for AKs. Aldara® (imiquimod) 5% cream works from within by activating the adult's own immune system to treat disease.

In the treatment of adults diagnosed with actinic keratosis, the approved dosing regimen for Aldara® (imiquimod) 5% cream is 2 times per week, for a full 16 weeks to a defined treatment area on the face or scalp (but not both concurrently). See Aldara® Package Insert (Label) Revised: March 2007 (Attachment VIII).

According to the approved Aldara® Package Insert (Label) Revised: March 2007 (Attachment VIII), the treatment area is defined as one contiguous area of up to approximately 25 cm² (e.g., 5 cm×5 cm) on the face (e.g. forehead or one cheek) or on the scalp, and examples of 2 times per week application schedules are Monday and Thursday, or Tuesday and Friday. The Aldara® Package Insert (Label) Revised: March 2007 (Attachment VIII) further instructs that the Aldara® (imiquimod) 5% cream should be applied to the entire treatment area and rubbed in until the cream is no longer visible. The Aldara® Package Insert (Label) Revised: March 2007 (Attachment VIII) cautions that no more than one packet of Aldara® (imiquimod) 5% cream should be applied to the contiguous treatment area at each application, and the Aldara® (imiquimod) 5% cream should be applied prior to normal sleeping hours and left on the skin for approximately 8 hours, after which time the cream should be removed by washing the area with mild soap and water.

The Aldara® Package Insert (Label) Revised: March 2007 (Attachment VIII) further advises that prescribers should demonstrate the proper application technique to maximize the benefit of Aldara® (imiquimod) 5% cream therapy.

The Aldara® Package Insert (Label) Revised: March 2007 (Attachment VIII) also recommends that patients should wash their hands before and after applying the Aldara® (imiquimod) 5% cream as well as the treatment area with mild soap and water and allow the area to dry thoroughly (at least 10 minutes) before applying Aldara® (imiquimod) 5% cream.

The Aldara® Package Insert (Label) Revised: March 2007 (Attachment VIII) further cautions that contact with the eyes, lips and nostrils should be avoided and warns that Aldara® (imiquimod) 5% cream is not for oral, ophthalmic, or intravaginal use.

Because the Aldara® (imiquimod) 5% cream is currently packaged in single-use packets, with 12 packets supplied per box, the Aldara® Package Insert (Label) Revised: March 2007 (Attachment VIII) instructs that patients should be prescribed no more than 3 boxes (36 packets) for the 16-week treatment period, and that unused packets should be discarded. The Aldara® Package Insert (Label) Revised: March 2007 (Attachment VIII) clearly warns that partially-used packets should be discarded and not reused.

Aldara® (imiquimod) 5% cream is also FDA approved to treat superficial basal cell carcinoma (sBCC), a form of skin cancer. See, e.g., Aldara® Package Insert (Label) Revised: March 2007 (Attachment VIII).

Skin cancer can occur anywhere on the body. Skin cancer, however, is most commonly diagnosed on skin that, like with AKs, has been in constant exposure to intense sunlight, especially during childhood or young adulthood. According to the American Cancer Society, the most common type of skin cancer is basal cell carcinoma (BCC), affecting about 800,000-900,000 Americans each year.

BCC develops within the basal cells, which are found within the basal layer of the epidermis or the top layer of the skin. Basal cells are typically small and round and continually divide to produce new skin cells and replace old ones.

BCC is typically a slow growing disease which can metastasize to other areas of the body including the lymph nodes, bone or other tissues beneath the skin if left untreated. Basal cell carcinoma occurs most often on sun exposed areas of the skin such as the head or neck. Although basal cell carcinoma rarely spreads to other parts of the body, it may cause local tissue destruction and it can be very destructive and disfiguring.

There are several types of BCC, including nodular basal cell carcinoma, superficial basal cell carcinoma (sBCC), small basal cell carcinoma, morpheaform basal cell carcinoma, infiltrating basal cell carcinoma, pigmented basal cell carcinoma, micronodular basal cell carcinoma and cystic basal cell carcinoma, each of which manifests a different pattern of behavior.

If allowed to progress without treatment, BCC can cause clinically significant morbidity. Because BCC most commonly affects the head and neck, cosmetic disfigurement is common. In addition, if there is orbital involvement, loss of vision or even loss of an eye may occur. BCC lesions are prone to ulceration and infection and, if there is perineural spread or deep and extensive skin invasion, nerve function can be lost. Death from BCC, however, is uncommon.

A history of chronic recreational or occupational sun exposure is typically observed in patients diagnosed with basal cell carcinoma. Common symptoms presented at diagnosis include lesions or sores that (a) won't heal, (b) vary in duration, and (c) often bleed when exposed to mild trauma, such as towel washing or drying.

Because there are several subtypes of BCC, it is critical for the health care provider to recognize and distinguish between the various subtypes in order to prescribe appropriate therapy. For example, aggressive therapy is often necessary for variants such as micronodular, infiltrating, morpheaform and superficial basal cell carcinoma.

Superficial basal cell carcinoma (sBCC) is one subtype of basal cell carcinoma. sBCC is the most common form of skin cancer, but it is readily treatable if identified and treated early. sBCC is generally diagnosed by a healthcare provider after biopsy. Typically, sBCC slowly progresses and clinically appears as erythematous eruptions or lesions. sBCC lesions may appear as new growths on the skin, as open sores that fail to heal, or as changes in appearance of an old growth on the skin. Generally, however, the sBCC lesions are usually not painful and may have different shapes and colors. sBCC lesions often present as pink to red-brown scaly patches or papules with a whitish scale. The sBCC lesions appear multicentric wherein clinically normal skin and clinically involved skin often intervene or commingle. The sBCC patches or papules may mimic eczema or psoriasis. sBCC skin changes to look for include the following:

A small, smooth, shiny lump that may be pale or waxy
A firm, red lump;
A sore or lump that bleeds or is covered by a scab; and/or
A red or brown patch that is rough or scaly and may itch or become tender.

sBCC is usually treated by surgical removal.

On Jul. 14, 2004, the FDA approved the use of Aldara® (imiquimod) 5% cream under biopsy-confirmed, primary superficial basal cell carcinoma (sBCC) in immunocompetent adults, with a maximum tumor diameter of 2.0 cm, located on the trunk (excluding anogenital skin), neck, or extremities (excluding hands and feet), only when surgical methods are medically less appropriate and patient follow-up can be reasonably assured. According to the Aldara® Package Insert (Label) Revised: March 2007 (Attachment VIII), the histological diagnosis of sBCC should be established prior to treatment with Aldara® (imiquimod) 5% cream, because Aldara® (imiquimod) 5% cream at that time was not approved for the treatment of other types of basal cell carcinomas, such as nodular and morpheaform (fibrosing or sclerosing) types.

In the treatment of sBCC diagnosed in adults, the approved dosing regimen for Aldara® (imiquimod) 5% cream is 5 times per week for a full 6 weeks to a biopsy-confirmed superficial basal cell carcinoma. See Aldara® Package Insert (Label) Revised: March 2007. An example of a 5 times per week application schedule is to apply Aldara® (imiquimod) 5% cream, once per day, Monday through Friday, for six full weeks. Aldara® (imiquimod) 5% cream should be applied prior to normal sleeping hours and left on the skin for approximately 8 hours, after which time the cream should be removed by washing the area with mild soap and water.

According to the Aldara® Package Insert (Label) Revised: March 2007, the prescriber should demonstrate the proper application technique to maximize the benefit of Aldara® (imiquimod) 5% cream therapy.

It is also recommended in the Aldara® Package Insert (Label) Revised: March 2007 that patients should wash their hands before and after applying Aldara® (imiquimod) 5% cream and that the patient should wash the treatment area with mild soap and water and allow the area to dry thoroughly before applying the cream.

According to the Aldara® Package Insert (Label) Revised: March 2007, the target sBCC tumor should have a maximum diameter of 2 cm and be located on the trunk (excluding anogenital skin), neck, or extremities (excluding hands and feet). Also according to the Aldara® Package Insert (Label) Revised: March 2007, the treatment area should include a 1 cm margin of skin around the tumor, and that sufficient cream should be applied to cover the treatment area, including 1 centimeter of skin surrounding the tumor. The Aldara® Package Insert (Label) Revised: March 2007 further instructs that the Aldara® (imiquimod) 5% cream should be rubbed into the treatment area until the cream is no longer visible.

As reported in the Aldara® Package Insert (Label) Revised: March 2007, the amount of Aldara® (imiquimod) 5% cream that should be used to treat sBCC is reproduced in Table 1 as follows.

TABLE 1

Amount of Aldara ® Cream to Use for sBCC

| Target Tumor Diameter | Size of Cream Droplet to be Used (diameter) | Approximate Amount of Aldara ® to be Used |
| --- | --- | --- |
| 0.5 to <1.0 cm | 4 mm | 10 mg |
| .1.0 to <1.5 cm | 5 mm | 25 mg |
| .1.5 to 2.0 cm | 7 mm | 40 mg |

According to the Aldara® Package Insert (Label) Revised: March 2007, contact with the eyes, lips and nostrils should be avoided and warns that Aldara® (imiquimod) 5% cream is not for oral, ophthalmic or intravaginal use.

Aldara® (imiquimod) 5% cream is packaged in single-use packets or sachets, with 12 packets supplied per box. Patients should be prescribed no more than 3 boxes (36 packets) for the 6-week treatment period. Unused packets and partially-used packets should be discarded and not reused. See Aldara® Package Insert (Label) Revised: March 2007 (Attachment VIII).

Thus, to date, the FDA has approved imiquimod 5% cream, commercially available under the brand name Aldara®, to treat dermal and/or mucosal-associated conditions, namely, the topical treatment of: (1) external genital and perianal warts, i.e., condyloma acuminate, in patients 12 years or older; (2) clinically typical, nonhyperkeratotic, nonhypertrophic AKs on the face or scalp in immunocompetent adults; and (3) biopsy-confirmed, primary sBCC in immunocompetent adults.

More recently, lower dosage strength formulations of imiquimod cream have been developed for use in effectively treating AKs and EGWs, which contain imiquimod in an amount by weight of between about 1% to about 4.25%, and preferably about 2.5% or about 3.75%. In conjunction with these lower dosage strength formulations, the treatment regimens for AKs and EGW have been uniquely shortened and simplified. These reduced dosage strength formulations and modified treatment regimens are disclosed in (1) U.S. patent application Ser. No. 12/636,613, (2) U.S. patent application Ser. No. 12/771,076, (3) PCT Publication No. WO/2010/080345, (4) PCT International Application No. PCT/US2009/067759, (5) PCT International Application No. PCT/US2010/33245, (6) Canadian Patent No. 2,649,893, issued on Aug. 3, 2010 and entitled "Lower Dosage Strength Imiquimod Formulations and Short Dosing Regimens for treating Actinic Keratosis", (7) the Zyclara® Package Insert (Label) (Attachment IX) for AK treatment with Zyclara® (imiquimod) 3.75% cream, (8) the proposed Zyclara® Package Insert (Label) (Attachment X) submitted to the FDA for EGW treatment with Zyclara® (imiquimod) 3.75% cream, (9) the Zyclara® Canada Product Monograph (Attachment XI) for AK treatment with Zyclara® (imiquimod) 3.75% cream, (10) the proposed Zyclara® Canada Product Monograph (Attachment XII) submitted to Health Canada for EGW treatment with Zyclara® (imiquimod) 3.75% cream, (11) the proposed Zyclara® Package Insert (Label) (Attachment XIII) for submission to the FDA for AK treatment with a pump pre-filled with Zyclara® (imiquimod) 3.75%, (12) the proposed Zyclara® Canada Product Monograph (Attachment XIV) for submission to Health Canada for AK treatment with a pump pre-filled with Zyclara® (imiquimod) 3.75%, and (13) the draft Zyclara® Package Insert (Label) (Attachment XV) for submission to the FDA for AK treatment with a pump pre-filled with Zyclara® (imiquimod) 2.5% cream, each of which is incorporated herein by reference in its entirety.

As discussed in U.S. patent application Ser. No. 12/771,076, and PCT International Application No. PCT/US2010/33245, a patient diagnosed with EGW can apply an effective amount of a lower strength formulation of imiquimod cream, such as a 2.5% or a 3.75% w/w formulation, to the wart area once a day for up to 8 weeks to achieve at least partial, if not complete, clearance of the wart.

Results from a Phase III program evaluating imiquimod 3.75% and 2.5% creams for the treatment of EGW, applied once daily for up to 8 weeks, demonstrated that both dosage strengths were well-tolerated and more efficacious than placebo. According to investigators conducting the study, strong efficacy results with the 3.75% unique formulation along with an enhanced safety profile were observed. More specifically, of those who achieved initial complete clearance and entered the 12-week follow-up, complete clearance was sustained in about 69.6% of the subjects on Zyclara® (imiquimod) 3.75% cream. As to the safety profile, a low incidence of treatment-related adverse events such as itching (2.5%), burning (5.8%) or pain (6.8%) at the application sites were observed, and no treatment-related reported systemic adverse events of headache or flu-like symptoms were observed. These surprising data were included in a New Drug Application (NDA) accepted for review by the FDA for the use of Zyclara® (imiquimod) 3.75% cream in an eight-week treatment regimen for the treatment of EGW.

With respect to AK treatment, the FDA, on Mar. 30, 2010, approved a topical 3.75% imiquimod pharmaceutical cream, commercially available under the brand name Zyclara®, to treat clinically visible or palpable actinic keratosis lesions (AKs), of the full face or balding scalp in immunocompetent adults. This newly approved dosing regimen with Zyclara® (imiquimod) 3.75% cream to treat AKs is a novel 6-week treatment regimen involving three cycles, that are equal in duration. In the first cycle of the 6-week treatment regimen, the Zyclara® (imiquimod) 3.75% cream is applied daily for two weeks to the targeted area, i.e., the full face or balding scalp diagnosed with AKs. In the second cycle of the 6-week treatment regimen designated as a rest period cycle, the Zyclara® (imiquimod) 3.75% cream is not applied to the targeted area. In the third or final cycle of the 6-week treatment regimen, the Zyclara® (imiquimod) 3.75% cream is again applied daily for two weeks to the targeted area. This unique 6-week treatment regimen to treat AKs with Zyclara® (imiquimod) 3.75% cream is referred to as a "2-week×2-week×2-week" or simply a "2×2×2" treatment regimen. See Zyclara® Package Insert (Label) (Attachment IX) attached hereto. See also the proposed Zyclara® Package Insert (Label) for Zyclara® (imiquimod) 2.5% cream to treat AKs in accordance with the 2×2×2" treatment cycle (Attachment XV).

Alternatively, a unique 9-week treatment regimen may be employed to treat AKs with Zyclara® (imiquimod) 3.75% cream or Zyclara® (imiquimod) 2.5% cream, wherein the 9 week treatment regimen involves three cycles as follows:

"3-week×3-week×3-week" or simply a "3×3×3" treatment regimen. Like with the 2×2×2 treatment regimen, the Zyclara® cream is applied daily to the targeted or treatment area in the first and third cycles, i.e., applied daily during the first and last 3-week cycles. However, during the second or middle 3-week cycle, it too is a rest period wherein no Zyclara® cream is applied during the second cycle.

One of the unique benefits associated with this new and improved treatment regimen, the Zyclara® (imiquimod) 3.75% cream serendipitously treats sub-clinical AKs (not clinically visible—not initially detected) located in the targeted treatment area at the same time of treatment of clinically visible AKs. Because the Zyclara® (imiquimod) 3.75% cream is applied to the "entire" face or "entire" balding scalp diagnosed with clinically visible AKs, unlike with current Aldara® treatment, the sub-clinical AKs within such treatment area are simultaneously treated with the Zyclara® (imiquimod) 3.75% cream during this "2×2×2" treatment regimen of the clinically visible AKs. These previously unseen AKs, that could appear during treatment, may therefore clear before they have a chance to develop further as a result of this unique "2×2×2" treatment regimen with Zyclara® (imiquimod) 3.75% cream.

The drug imiquimod, contained in both Aldara® and Zyclara®, is an immune response modifier. Chemically, imiquimod is known as 1-(2-methylpropyl)-1H-imidazo[4,5-c]quinolin-4-amine or 1-isobutyl-1H-imidazo[4,5-c]-quinolin-4-amine. Imiquimod has a molecular formula of $C_{14}H_{16}N_4$ and a molecular weight of 240.3. The chemical structural formula for imiquimod is as follows:

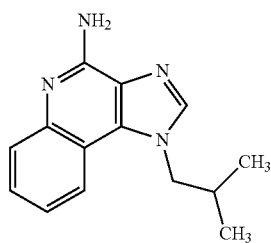 [SMILES: CC(C)Cn1cnc2c(N)nc3ccccc3c21]

Common to each of the FDA-approved treatments with imiquimod for treating EGWs, AKs and sBCC, the correct amount of cream or a specific unit dose to be applied each time by the patient is required for effective therapy. Also common to each of such FDA-approved treatments with imiquimod, is the inconvenient and imprecise use of single-use packets or sachets to apply the topical imiquimod pharmaceutical creams to the treatment areas.

For example, if the Aldara® (imiquimod) 5% cream or Zyclara® (imiquimod) 3.75% cream is applied too thickly or generously, the over dosage can exacerbate unwanted site reactions or local skin reactions, such as erosions or ulcerations, causing pain or dysfunction (e.g., of the foreskin or urethra), and cause undesirable systemic absorption of the imiquimod leading to flu-like symptoms and headaches. Moreover, if the patient is not careful, the patient will inadvertently apply residual Aldara® (imiquimod) 5% cream or Zyclara® (imiquimod) 3.75% cream to other areas of the body compounding over dosage issues that can further exacerbate the unwanted side effects.

If, however, too little imiquimod cream is applied to the targeted areas, the patient may not achieve the maximum level or even an effective level of therapeutic benefit.

Also common to each of the FDA-approved treatments with imiquimod for treating EGW, AK and sBCC, the pharmaceutical concentration and stability of the imiquimod formulation provided to the patient must be maintained throughout the duration of the treatment, which could be for as long as 16 weeks when treating EGWs and AKs with Aldara® (imiquimod) 5% cream or for up to 8 weeks when treating EGWs with Zyclara® 3.75% (imiquimod) cream or for up to 6 weeks when treating sBCC with Aldara® (imiquimod) 5% cream. Thus, the storage devices should not adversely impact the stability, uniformity, dosing concentration or dosing technique of the pre-filled topical semi-solid imiquimod pharmaceutical formulation.

Each gram of Aldara® (imiquimod) 5% cream contains 50 mg of imiquimod and each gram of the Zyclara® (imiquimod) 3.75% cream contains 37.5 mg of imiquimod. The Aldara® (imiquimod) 5% cream and the Zyclara® (imiquimod) 3.75% cream are each formulated in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben. The Aldara® (imiquimod) 5% cream is packaged in single-use packets or sachets, each containing 250 mg of cream, equivalent to 12.5 mg of imiquimod. The Zyclara® (imiquimod) 3.75% cream is packaged in single-use packets or sachets, each containing 250 mg of cream, equivalent to 9.375 mg of imiquimod.

Unfortunately, single-use packets or sachets pre-filled with an imiquimod pharmaceutical cream are not without drawback. There are several disadvantages associated with providing an imiquimod pharmaceutical cream to a patient in a single-use packet or sachet. Single-use packets or sachets pre-filled with a topical imiquimod pharmaceutical cream are, for example, notoriously messy, difficult and clumsy to use, and more importantly notably imprecise. These known drawbacks can lead to needless product waste, overdosing, inadequate dosing, failed compliance, contamination and/or passive (unintended) transfer to other areas of the patients' bodies, such as the eyes, ears, nose, mouth and vagina.

To underscore these drawbacks, patients often fail to apply the appropriate dosage amount or to ensure that all of the imiquimod cream is squeezed out of the single-use packet or sachet during appplication to the treatment area. Consequently, patients are frequently under-dosed or over-dosed, which can lead to poor patient compliance.

This problem is recognized in the FDA-approved Labels and Health Canada-approved Labels for both the Aldara® (imiquimod) 5% cream and the Zyclara® (imiquimod) 3.75% cream, as well as in the proposed FDA Labels and Health Canada Labels for the Zyclara® (imiquimod) 3.75% cream and in the draft FDA-Label for Zyclara® (imiquimod) 2.5% cream, each of which are incorporated herein by reference in their entireties. See, for example, Attachments VIII and XV, respectively. In each of the FDA-approved and FDA-proposed Labels and in each of the Health Canada-approved and Health Canada-proposed Labels, the prescriber is clearly instructed to demonstrate the proper application technique for the Aldara® (imiquimod) 5% cream, the Zyclara® (imiquimod) 3.75% cream and the Zyclara® (imiquimod) 2.5% cream, respectively, to the patients to minimize or avoid these drawbacks. Thus, dosing inconsistencies and product waste associated with single-use packets or sachets pre-filled with a topical imiquimod pharmaceutical cream are problematic, common and cause for concern.

Another drawback associated with single-use packets or sachets pre-filled with a topical imiquimod pharmaceutical cream concerns excessive contact with and improper application technique of the dispensed imiquimod pharmaceutical creams from the single-use packets or sachets by the patients. Because imiquimod is an immune response modifier, minimal patient contact and proper application technique is important to avoid imiquimod cream contamination, imprecise dosing, product waste, passive transfer to other parts of the patient's body that are outside of the treatment area, such as the eyes, ears, nose, mouth and vagina. These problems are also recognized in each of the FDA-approved, Health Canada-approved and proposed Labels wherein each Label (a) instructs the patients to thoroughly wash their hands "before" and "after" imiquimod cream application, (b) cautions that topical imiquimod creams contact with eyes, lips and nostrils should be avoided, and (c) warns that topical imiquimod creams are not for oral, ophthalmic, or intravaginal use. See Attachments VIII-XV, each of which is incorporated herein by reference in its entirety.

In yet another drawback, single-use packets or sachets pre-filled with a topical imiquimod pharmaceutical cream can be very difficult and cumbersome to use, especially when elderly patients are involved. Opening a single-use packet or sachet pre-filled with a topical imiquimod cream to dispense the imiquimod cream to "only" the targeted area without excessive handling or passive transfer can in some instances present real application technique challenge to those patients inflicted with, for example, limited dexterity, crippling arthritis, vision loss and/or visual acuity loss, which are commonly observed in elderly patients.

In still another drawback, needless product waste often occurs with single-use packets or sachets pre-filled with a topical imiquimod cream. Clear instruction to patients provides that undispensed imiquimod cream and unopened individual packets or sachets pre-filled with a topical imiquimod cream must be discarded. This particular drawback is highlighted in all Labels, the FDA-approved and proposed Labels and the Health Canada approved and proposed Labels for Aldara® (imiquimod) 5% cream and Zyclara® (imiquimod) 3.75% cream, respectively. As stated above, and according to such Labels, unopened and partially used single-use packets or sachets pre-filled with a topical imiquimod cream must be discarded and not reused. See Attachments VIII-XII. See also Attachments XIII-XV.

In yet another drawback associated with single-use packets or sachets pre-filled with a topical imiquimod cream, the single use packets or sachets can be easily lost or misplaced due to the fact that several single-use packets or sachets must be purchased to complete a full course of therapy. This drawback and inconvenience can cause further product waste and needless elevated treatment costs due to necessary product replacement. More seriously, this drawback and inconvenience can lead to failed patient compliance and ineffective imiquimod therapy.

In still another drawback associated with such single-use packets or sachets, imiquimod cream degradants may develop over time as a result of storage in the single-use packets or sachets. This drawback can cause an adverse effect on overall efficacy and/or stability of the imiquimod cream formulations packaged within the single-use packets or sachets.

Thus, given the numerous drawbacks associated with single-use imiquimod cream packets or sachets, there is a real need for a simple, safe, clean, easy-to-use, compact, reliable and all-in-one storage system for dispensing topical semi-solid imiquimod pharmaceutical formulations that: (i) can dispense a controlled and precise amount of imiquimod cream each and every time the topical imiquimod formulation is applied to a treatment area, (ii) is easy and convenient for any patient, young or old, to use; (iii) improves imiquimod therapy compliance and effectiveness, (iv) provides the same unit dose, such as approximately 250 mg of imiquimod formulation, per each actuation, i.e., a reproducible dose amount, so that an effective dose is administered each and every time; (v) does not interfere with or hinder imiquimod application technique, (vi) minimizes if not eliminates product waste and product loss, (vii) minimizes if not eliminates excessive patient contact to avoid passive transfer, (viii) minimizes and/or prevents degradant formation during imiquimod formulation storage; and (ix) is compatible for use with topical semi-solid imiquimod formulations, for example, topical 2.5%, 3.75% and 5% weight to weight imiquimod creams, for treating dermal and/or mucosal-associated conditions, such as external genital warts, perianal warts, actinic keratoses and superficial basal cell carcinoma.

SUMMARY OF THE INVENTION

The present invention overcomes certain of the above-mentioned problems and drawbacks of the present state of the art of topical imiquimod therapy using single-use packets or sachets pre-filled with an imiquimod pharmaceutical cream through the development of a novel and unique storage and dispensing system that includes a pump or dispensing package pre-filled with a topical semi-solid imiquimod pharmaceutical formulation (hereinafter, a "pump system"), preferably a topical imiquimod pharmaceutical cream, in a selected dosage strength for dispensing a plurality of precisely measured unit-doses of the imiquimod formulation over pump life, in which each precisely measured unit dose dispensed is consistent in uniformity and amount, for effectively treating dermal and/or mucosal-associated conditions, such as external genital warts or perianal warts (EGWs), actinic keratosis or actinic keratoses (AK or AKs) or superficial basal cell carcinoma (sBCC).

Uniquely, the novel pump systems of the present invention are clean and sanitary, safe and simple and easy to use. In addition, the novel and unique pump systems of the present invention are compact (hand held) and easy to store, they are reliable, they minimize product waste, and they improve application technique of the dispensed topical semi-solid imiquimod pharmaceutical formulations when treating dermal and/or mucosal-associated conditions, such as EGWs, AKs or sBCC.

In view of these and other novel and unique features of the pump systems of the present invention, it is believed that the effectiveness and benefits of topical imiquimod therapy can now be maximized and that certain if not all drawbacks associated with the use of single-use packets or sachets to deliver topical imiquimod pharmaceutical cream can now be minimized if not eliminated.

The unique pump systems of the present invention include, inter alia, a dispensing package that has a tubular main body portion and a manually-operated airless pumping device mounted on the main body portion. The main body portion of the dispensing package defines a fluid storage chamber. The airless pumping device defines a dispensing duct which terminates in a self-closing discharge orifice. In alternative embodiments, the airless pumping device can include a cap or cover for sealing or covering the discharge orifice. The cap or cover can be operated automatically or manually.

The pump system of the present invention further includes a topical semi-solid imiquimod pharmaceutical formulation, such as a topical imiquimod pharmaceutical cream formulation, which is disposed at least partially within the fluid storage chamber defined in the main body portion of the dispensing package. The system is constructed such that manual operation of the airless pumping device causes a portion of the imiquimod cream to be withdrawn from within the fluid storage chamber into the dispensing duct thereby causing the self-closing discharge orifice to open and to dispense, per actuation, a predefined, uniform and precisely measured unit-dose amount of a topical imiquimod pharmaceutical cream formulation from the dispensing package.

Thus, the novel pump systems of the present invention now afford patients with the unique advantage of applying a consistent, precisely measured and uniform unit-dose of a topical semi-solid imiquimod pharmaceutical formulation from a clean, safe, easy and simple to use, compact and reliable pump system to a treatment area per each application, so that application technique and patient compliance are improved and the effectiveness and benefits of topical imiquimod therapy are maximized, while minimizing (a) imprecise or inconsistent dosing amounts, i.e., under-dosing or over-dosing, (b) unwanted passive transfer of the dispensed topical imiquimod cream due to improper handling of the imiquimod cream and poor application technique, (c) imiquimod cream waste, and (d) unused product and/or product loss, each of which can contribute to poor patient compliance and less effective, if not ineffective, topical imiquimod therapy.

Preferably, a topical semi-solid imiquimod pharmaceutical formulation contains imiquimod in an amount by weight of between about 1% and about 10% w/w and more preferably a topical semi-solid imiquimod pharmaceutical formulation contains imiquimod in an amount by weight of between about 1% and about 5%. Even more preferably, the topical semi-solid imiquimod pharmaceutical formulations can contain imiquimod in an amount by weight of between about 1% and 4.25% w/w, and most preferably, the topical semi-solid imiquimod pharmaceutical formulations can contain imiquimod in an amount by weight of about 2.5%, about 3.75% or about 5%.

In a preferred embodiment, the fluid storage chamber formed in the main body portion of the dispensing device is adapted and configured for storing about 15 grams of a topical semi-solid imiquimod pharmaceutical formulation, namely, a topical imiquimod pharmaceutical cream formulation, e.g., Aldara® (imiquimod) 5% cream, Zyclara® (imiquimod) 3.75% cream or a 2.5% imiquimod pharmaceutical cream described herein. In alternative constructions, the fluid storage chamber can be adapted and configured for storing about 7.5 grams of a topical semi-solid imiquimod pharmaceutical formulation, such as a topical imiquimod pharmaceutical cream formulation, namely, Aldara® (imiquimod) 5% cream, Zyclara® (imiquimod) 3.75% cream or a 2.5% imiquimod pharmaceutical cream described herein.

It should be understood by those versed in this art that the pump systems of the present invention can be pre-filled with any suitable topical semi-solid imiquimod pharmaceutical formulation, such as a cream, an ointment, a lotion, a balm, a salve or the like, that can be effectively dispensed there from in accordance with the teachings of the present invention without departing from the purpose or scope of the present invention. Thus, when the pump systems of the present invention are described as being pre-filled with a topical imiquimod pharmaceutical cream, such description is done so for exemplary purposes without intent to be bound to any particular topical semi-solid imiquimod dosage form or formulation.

It is envisioned that certain constructions of the present invention further include a take-up piston which is slidably disposed within the tubular main body portion so as to partially define the fluid storage chamber. The take-up position moves axially towards the pumping device when the pumping device is manually operated, so as to reduce the volume of the fluid storage chamber by an amount which is equivalent to the volume of imiquimod cream formulation dispensed from the dispensing package, i.e., the unit-dose amount. In constructions wherein the take-up piston defines a portion of the fluid storage chamber, it can be positioned during assembly to established the desired volume of the fluid storage chamber. For example, if it is desired to pre-fill the dispensing device with 15 g of an imiquimod cream, the piston can be initially positioned during the filling operation at a distance from the top of the main body portion of the dispensing package such that the volume of the fluid storage chamber corresponds to the volume required to hold 15 g of imiquimod cream. Alternatively, if 7.5 grams of cream is to be stored, the piston can be moved the appropriate distance towards the top of the main body portion of the dispensing package to accommodate 7.5 g of imiquimod cream. Of course, it should be appreciated by those versed in this art that the imiquimod pump systems of the present invention contemplate functional fluid storage chambers that can accommodate any desired volume of imiquimod cream, including fluid storage chambers that can hold and store volumes greater or lesser than 7.5 g or 15 g of imiquimod cream, so long as the objectives of the present invention are not defeated.

Preferably, with each operation of the pumping device, an amount of the imiquimod cream formulation which is within about 15% of the predefined unit dose is discharged from the dispensing device per actuation. Still further, after multiple operations of the pumping device, the overall average of the dose value is within about 10% of the predefined unit dose per actuation. In certain constructions, it is envisioned that the predefined unit dose amount dispensed per actuation is about 250 mg, and more preferably about 240 mg.

It is preferred that no more than about 5 manual actuations of the pumping device are required to effectively prime the pumping device and start observing the discharging of imiquimod cream formulation from the self-closing discharge orifice.

Following the initial operation or priming of the pumping device, imiquimod cream uniquely remains within the dispensing duct, i.e., the pump is now primed. Preferably, about 85% or more of the imiquimod cream contained within the dispensing duct of the pumping device following each actuation remains in the dispensing duct during storage and prior to the next actuation by the patient, so that the same uniform and consistent unit dose amount is dispensed per each actuation, even when a pump system of the present invention has been stored (static—not actuated) for a few days or a few weeks between actuations, consistent with the prescribed treatment regimens and/or rest periods taken when treating a diagnosed dermal and/or mucosal-associated condition, such as, external genital warts, perianal warts, actinic keratosis or superficial basal cell carcinoma, with a topical semi-solid imiquimod pharmaceutical formulation as described herein.

The present invention is further directed to a pump system for treating a subject diagnosed with a dermal and/or mucosal-associated conditions, such as genital warts or perianal warts, actinic keratosis or superficial basal cell carcinoma, which includes, inter alia, a dispensing package that is pre-filled with a topical semi-solid imiquimod pharmaceutical formulation, such as an imiquimod cream formulation. The dispensing package includes a lower subassembly and an upper subassembly. The lower subassembly has a tubular body portion that defines an elongated interior fluid storage chamber into which a take-up piston element is slidably disposed. The upper subassembly is mounted upon the lower subassembly and includes a dispensing head and an airless pumping mechanism. The dispensing head has an internal fluid passage or discharge duct formed therein which terminates in a self-closing outlet. The dispensing head also includes a finger-operated actuator which is operatively associated with the airless pumping mechanism. The dispensing package may further include a cap to seal or cover the dispensing head or nozzle.

The topical semi-solid imiquimod pharmaceutical formulation, e.g., an imiquimod cream formulation, is disposed at least partially within the fluid storage chamber defined in the tubular body portion of the lower subassembly of the dispensing package. Operation of the finger-operated actuator causes the airless pumping mechanism to withdraw a portion of the imiquimod cream from within the interior chamber and to dispense the imiquimod cream into the internal fluid passage formed in the dispensing head wherein the pressure of the dispensed cream causes the self-closing outlet to open thereby discharging a predetermined final unit dose of imiquimod cream from the dispensing head.

In certain preferred embodiments, the take-up piston is disposed within the tubular body portion so as to partially define the fluid storage chamber. The take-up position is arranged such that it moves axially towards the pumping device when the pumping device is manually operated, so as to reduce the volume of the fluid storage chamber by an amount which is equivalent to the volume of imiquimod cream dispensed from the dispensing package, i.e., the unit dose amount, as discussed above.

In a pump system for treating a subject diagnosed with a dermal and/or mucosal-associated conditions, such as EGWs, AKs or sBCC, the pump system includes a dispensing package that has a tubular main body portion and a manually-operated airless pumping device mounted on the main body portion. The main body portion of the dispensing package defines a fluid storage chamber which is in fluid communication with a dispensing duct which is defined in the pumping device and that terminates in a discharge orifice.

The pump system of the present invention further includes a mechanism for closing the discharge orifice when the dispensing package is not in use and a topical semi-solid imiquimod pharmaceutical formulation, e.g., an imiquimod cream formulation, that is disposed at least partially within the fluid storage chamber defined in main body portion of the dispensing package. Wherein, manual operation of the airless pumping device causes a portion of the imiquimod cream to be withdrawn from within the fluid storage chamber and a predefined unit dose of imiquimod cream to be dispensed from the discharge orifice of the dispensing package. Preferably, the mechanism for closing the discharge orifice when the dispensing package is not in use includes a shutter element that has a self-closing orifice. Alternatively or additionally, the mechanism for closing the discharge orifice when the dispensing package is not in use can include a cap, a cover or a plug.

The present invention is also directed to methods for treating dermal and/or mucosal-associated conditions with the novel and unique pump systems pre-filled with topical semi-solid imiquimod pharmaceutical formulations. Generally speaking, the methods of the present invention comprise treating a dermal and/or mucosal-associated condition with a topical semi-solid imiquimod pharmaceutical formulation dispensed from a novel and unique imiquimod pump system of the present invention in accordance with effective treatment regimens, such as those treatment regimens described herein. For example, the methods of the present invention comprise (1) actuating a primed dispensing pump system pre-filled with a topical semi-solid imiquimod pharmaceutical formulation to dispense there from an effective precisely measured unit-dose amount of the pre-filled topical semi-solid imiquimod pharmaceutical formulation for treating a dermal and/or mucosal-associated condition, wherein the unit-dose amount dispensed per each actuation is the same effective precisely measured unit-dose amount for consistent dose application over the course of the treatment regime, and (2) applying the dispensed unit-dose amount to a treatment area diagnosed with a dermal and/or mucosal-associated condition in accordance with the treatment regimen to treat the diagnosed dermal and/or mucosal-associated condition.

It of course should be understood that the methods of the present invention contemplate the use of any suitable topical semi-solid imiquimod pharmaceutical formulation, preferably imiquimod pharmaceutical creams, wherein the imiquimod is present in an amount by weight of about 1% to about 10% w/w, and more preferably in an amount by weight of about 1% to about 5% w/w, and even more preferably in an amount by weight of about 2.5% w/w, about 3.75% w/w and about 5% w/w.

It should also be understood, as discussed above, that the methods of the present invention envision treatment of dermal and/or mucosal-associated conditions such as external genital warts and/or perianal warts (EGWs), actinic keratosis (AKs) and superficial basal cell carcinoma (sBCC) in accordance with effective treatment regimens such as those described here in throughout.

Thus, when practicing the pump systems of the present invention, each unit-dose amount dispensed from an imiquimod pump system per each actuation is the same precisely measured unit-dose amount, preferably pre-selected at the time of pump fill, so that the same precisely measured unit-dose amount of the pre-filled topical semi-solid imiquimod pharmaceutical formulation is delivered to the targeted treatment area per each application in accordance with an effective treatment regimen, so that the effectiveness and benefits of topical imiquimod treatment of a treated dermal and/or mucosal-associated condition, such as EGWs, AKs or sBCC, are maximized and the drawbacks associated with single-use imiquimod packets or sachets are minimized, if not eliminated.

To further illustrate certain unique advantages of the pump systems of the present invention, once such a pump system pre-filled with a topical semi-solid imiquimod pharmaceutical formulation, such as a 3.75% w/w imiquimod cream as described herein, is primed, each pre-selected unit-dose amount of the 3.75% w/w imiquimod cream dispensed there after will be repeatedly and consistently dispensed over pump life. Thus, if the pre-selected unit-dose amount to be delivered per actuation is about 240 mg, each single actuation of a primed pump system will consistently deliver about 240 mg of the 3.75% imiquimod cream.

Of course, it should be appreciated that the number of single unit-doses that will be dispensed over pump life will be a function of the total pre-fill volume and the pre-selected unit-dose amount. Thus, if the pre-fill volume is, e.g., 15 g, and the pre-selected unit-dose amount per actuation or pump is about 240 mg, such a pre-filled pump will have the ability to deliver about 62 unit-doses of imiquimod cream at about 240 mg/pump over pump life. If, however, the pre-fill pump volume is, e.g., 7.5 g, such a pre-filled pump will have the ability to deliver about 31 unit-doses of imiquimod cream at about 240 mg/pump over pump life.

Thus, a pump system of the present invention pre-filled with about 15 g of, for example, a 3.75% w/w imiquimod cream or a 5% w/w imiquimod cream, can accommodate, for example, the following two treatment regimens for treating EGWs when each unit-dose dispensed is: (1) single unit doses of about 240 mg of a 3.75% imiquimod cream/pump that is to be applied daily for up to 8 weeks or for up to a total of about 56 single unit-doses of 3.75% imiquimod cream (56 individual pumps) over the course of the treatment regimen; or (2) single unit-doses of about 240 mg of a 5% imiquimod cream/pump to be applied three times a week for up to 16 weeks or for up to a total of about 48 single unit-doses of 5% imiquimod cream (48 individual pumps) over the course of the treatment regimen. On the other hand, if a pump system of the present invention is prefilled with about 7.5 g of, for example, a 3.75% w/w imiquimod cream or a 5% w/w imiquimod cream, such a pre-filled pump can accommodate the following two treatment regimens for treating AKs or sBCC when each unit-dose dispensed is: (1) single unit doses of about 240 mg of a 3.75% imiquimod cream/pump applied daily in accordance with a 2×2×2 treatment regimen to treat AKs or for up to a total of about 28 single unit-doses of 3.75% imiquimod cream (28 individual pumps) over the course of the 2×2×2 treatment regimen for AK treatment; or (2) single unit-doses of about 240 mg of a 5% imiquimod cream/pump applied five times a week for up to 6 weeks to treat sBCC or for up to a total of about 30 single unit-doses of 5% imiquimod cream (30 individual pumps) over the course of the treatment regimen for sBCC treatment.

It should be appreciated that the above is described when only a single pump for dispensing an unit-dose amount of about 240 mg/unit-dose is to be applied during the appropriate treatment regimen. However, when a unit-dose of about 480 mg/unit-dose is required per application in accordance with an appropriate treatment regimen, two pumps or actuation will be required (if the pre-set unit dose per pump is about 240 mg/pump) to deliver the necessary 480 mg unit-dose per application and that at least two 7.5 g or at least two 15 g pumps should be prescribed and dispensed to complete the prescribed treatment regimen when appropriate. Thus, it should be realized by those of skill in the art that the number of pump systems pre-filled with a topical semi-solid imiquimod pharmaceutical formulation that are to be prescribed and dispensed will, of course, depend upon (1) the pre-fill volume of the pump system, (2) the precisely measured amount of the unit-dose dispensed per pump or actuation, and (3) the appropriate treatment regimen selected to treat a treatment area diagnosed with a dermal and/or mucosal-associated condition, such as EGWs. AKs or sBCC.

To illustrate further, a method of the present invention contemplates treating a patient diagnosed with a dermal and/or mucosal-associated condition, such as EGWs, AKs or sBCC, with a topical semi-solid imiquimod pharmaceutical formulation, wherein such method includes: (1) priming a pump system pre-filled with a topical semi-solid imiquimod pharmaceutical formulation, e.g., an imiquimod cream, to prepare the pump system to dispense a plurality of pre-defined, precisely measured and consistent unit-doses of the topical imiquimod formulation to treat the diagnosed dermal and/or mucosal condition in accordance with an appropriate treatment regimen; (2) pumping the primed pump system no more than twice to dispense one of the predefined and precisely measured unit-doses onto a treatment area diagnosed with the dermal and/or mucosal-associated condition in accordance with an appropriate treatment regimen, (3) rubbing the dispensed unit dose amount of topical imiquimod cream into the treatment area until the dispensed unit-dose is no longer visible, (4) leaving the rubbed-in unit dose on the treatment area for a sufficient treatment period in accordance with the appropriate treatment regimen, for effectively treating the diagnosed dermal and/or mucosal condition; and (5) repeating the above-recited pumping or actuating step (2), the above-recited rubbing step (3) and the above-recited leaving step (4) a number of times as specified by the appropriate treatment regimen to effectively treat the diagnosed dermal and/or mucosal-associated condition and to maximize the benefit of topical imiquimod treatment.

When practicing the methods of the present invention, it is preferable for the patient to wash his/her hands with mild soap and water before and after dispensing each prescribed unit-dose from an imiquimod pump system of the present invention. It is also preferable to wash the treatment area diagnosed with a dermal and/or mucosal-associated condition with soap and water and to allow the washed treatment area to dry before dispensing the prescribed unit-dose from the pump system and applying such dispensed unit-dose to the targeted treatment area. Also, when carrying out the methods of the present, it is preferable to avoid contacting the dispensed unit-dose with the eyes, lips, nostrils, mouth and/or vagina of the patient.

More specifically, a method of the present invention comprises applying a topical semi-solid imiquimod pharmaceutical formulation, and preferably applying a topical imiquimod pharmaceutical cream, dispensed from an airless pump system of the present invention, equipped with a cap for protecting the dispensing head, to a treatment area of a patient diagnosed with a dermal and/or mucosal-associated condition to treat the dermal and/or mucosal-associated condition. More particularly, this one such method comprises (a) washing a treatment area diagnosed with a dermal and/or mucosal-associated condition to treat the dermal and/or mucosal-associated condition where the imiquimod cream will be applied with mild soap and water, (b) allowing the washed treatment area to dry, (c) washing the hands of the patient and allowing the washed hands to dry, (d) removing the cap from the pump system prefilled with a topical imiquimod pharmaceutical cream, (e) tilting the pump system for dispensing the imiquimod cream there from, (f) priming the pump system by firmly pressing the top of the pump or dispensing head all the way down up to about five times as needed until the imiquimod cream appears at the dispensing head outlet, (g) dispensing the primed imiquimod cream from the dispensing head into a paper tissue and then discarding such dispensed cream, (h) pressing the top of the pump system or dispensing head all of the way down up to two times as needed to dispense a precisely measured unit-dose of the topical imiquimod pharmaceutical cream into the hand of the patient, (i) applying the precisely measured unit-dose of the topical imiquimod pharmaceutical cream to the washed and dried treatment area in accordance with a prescribed treatment regimen for treating the treatment area diagnosed with the dermal and/or mucosal-associated condition, (j) rubbing the applied unit-dose all the way into the washed and dried treatment area, (k) re-washing the hands of the patient after the unit-dose has been rubbed into the washed and dried treatment area, (l) leaving the rubbed-in imiquimod cream on the treatment area, without wetting or washing the treated treatment area, for up to about 8 hours to treat the dermal and/or mucosal-associated condition, (m) re-washing the treated treatment area with soap and water after the 8 hours has passed, and (n) repeating the said steps (h) through (m) herein in accordance with a prescribed treatment regimen to dispense and apply precisely measured and reproducible unit-doses of the topical imiquimod pharmaceutical cream to effectively treat the diagnosed dermal and/or mucosal-associated condition, wherein each said unit-dose dispensed from the pump system of the present invention during step (h) is a precisely measured, consistent, reproducible and uniform amount, so that they same dosage amount of the topical imiquimod pharmaceutical cream is applied each and every time over the course of the prescribed treatment regimen, thereby avoiding dosing inconsistencies and other drawbacks observed or associated with single-use packets or sachets.

It is also a feature of the present invention to instruct prescribers and patients as to: (1) the correct use of the pre-filled imiquimod pump systems and treatment regimens in order to optimally practice the pre-filled imiquimod pump systems of the present invention to effectively treat dermal and/or mucosal associated conditions, such as EGWs, AKs or sBCC, with topical imiquimod therapy; (2) the correct way for prescribers to prescribe the pre-filled imiquimod pump systems, including the treatment regimens, of the present invention to effectively treat dermal and/or mucosal associated conditions, such as EGWs, AKs or sBCC; and (3) the correct way for patients in need of therapy to practice the pre-filled imiquimod pump systems in accordance with the present invention to effectively treat dermal and/or mucosal associated conditions, such as EGWs, AKs or sBCC, and to maximize the benefits of topical imiquimod therapy.

The present invention also contemplates the use of instructions provided on, for example, a label, package insert or other communicative materials to teach prescribers and/or patients how to correctly and most effectively prescribe and use, respectively, the pre-filled imiquimod pump systems of the present invention to effectively treat dermal and/or mucosal associated conditions, such as EGWs, AKs or sBCC, and to maximize the benefits of topical imiquimod therapy.

Thus, it should now be clear that the present invention uniquely affords a proper, safe, convenient, easy and advantageous way to use the novel pre-filled imiquimod pumps to practice treatment regimens of the present invention to improve patient compliance and to more effectively treat dermal and/or mucosal-conditions, such as EGWs, AKs or sBCC, with topical semi-solid imiquimod pharmaceutical formulations, such as with topical semi-solid imiquimod pharmaceutical creams, while mitigating, if not eliminating, the drawbacks associated with the use of single-use packets or sachets pre-filled with topical imiquimod formulations to treat the same skin disorders.

The above summary of the present invention is not intended to describe each disclosed embodiment or every implementation of the present invention. The description and examples that follow more particularly exemplify illustrative embodiments. In several places throughout the specification, guidance is provided through lists of examples, which examples can be used in various combinations. In each instance, the recited list serves only as a representative group and should not be interpreted as an exclusive list.

BRIEF DESCRIPTION OF THE DRAWINGS

So that those having ordinary skill in the art to which the present invention pertains will more readily understand how to employ the pump systems and methods of the present invention, embodiments thereof will be described in more detail herein below with reference to the drawings, wherein.

Figure 1:
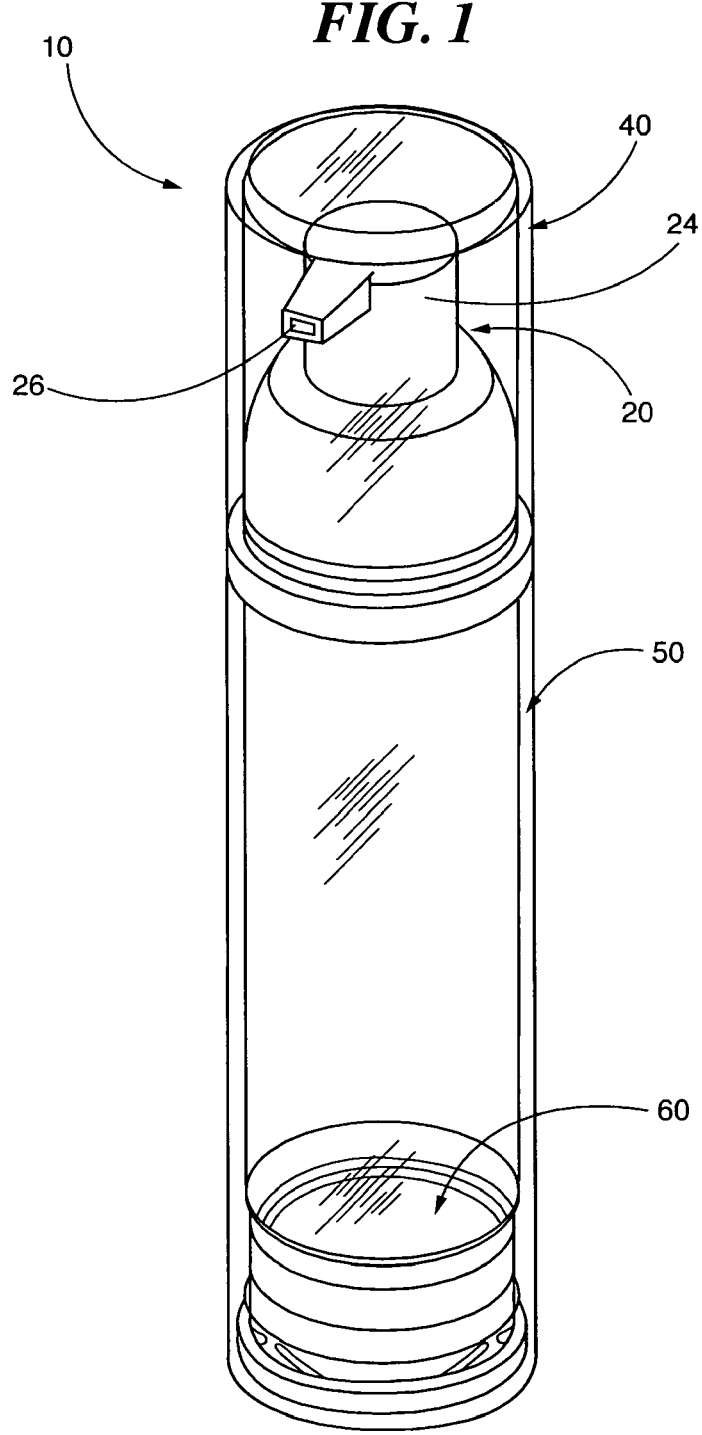
FIG. 1 is a perspective view of a dispensing package which has been constructed in accordance with a preferred embodiment of the present invention.

These and other aspects of the subject invention will become more readily apparent to those having ordinary skill in the art from the following detailed description of the invention taken in conjunction with the drawings and examples.

DETAILED DESCRIPTION

Disclosed herein are detailed descriptions of specific embodiments of the devices, systems and methods for storing and dispensing unit doses of a topical semi-solid imiquimod pharmaceutical formulation, such as an imiquimod cream. It will be understood that the disclosed embodiments are merely examples of the way in which certain aspects of the invention can be implemented and do not represent an exhaustive list of all of the ways the invention may be embodied. Indeed, it will be understood that the pump systems, devices, methods and package assemblies described herein may be embodied in various and alternative forms. The figures are not necessarily to scale and some features may be exaggerated or minimized to show details of particular components. Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention.

Thus, by way of illustrating and providing a more complete appreciation of the present invention and many of the attendant advantages thereof, the following detailed description and examples are given concerning the novel methods and compositions.

Unless otherwise indicated, all numbers expressing quantities, ratios, and numerical properties of ingredients, reaction conditions, and so forth used in the specification and claims are to be understood as being modified in all instances by the term "about".

All parts, percentages, ratios, etc. herein are by weight unless indicated otherwise.

As used herein, the singular forms "a" or "an" or "the" are used interchangeably and intended to include the plural forms as well and fall within each meaning, unless expressly stated otherwise. Also as used herein, "at least one" is intended to mean "one or more" of the listed elements. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

The compound imiquimod is a known antiviral agent that is also known to induce interferon biosynthesis. It can be prepared using the method disclosed in U.S. Pat. No. 4,689,338, the disclosure of which is incorporated herein by reference in its entirety. The compound can be used to treat dermal and/or mucosal-associated conditions, such as external genital and perianal warts (EGWs), actinic keratoses (AKs) or superficial basal cell carcinoma (sBCC). The amount of imiquimod present in a topical semi-solid imiquimod pharmaceutical formulation of the present invention will be an effective amount to treat a dermal and/or mucosal-associated condition, for example, (a) EGWs, (b) AKs or (c) sBCC, as described herein. An example of an effective amount of imiquimod in a formulation of the present invention is between about 1. percent and about 10 percent by weight based on the total weight of a formulation, more preferably between about 2.5% and 5%, and more preferably about 1.25%, 1.5%, 1.75%, 2.0%, 2.25%, 2.5%, 2.75%, 3.0%, 3.25%, 3.5%, 3.75%, 4.0%, 4.25%, 4.5%, 4.75% and 5%, even more preferably between about 2.0%, 2.25%, 2.5%, 2.75%, 3.0%, 3.25%, 3.5%, 3.75% and 4.0%, and still even more preferably between about 2.5%, 2.75%, 3.0%, 3.25%, 3.5% and 3.75%. Imiquimod formulations of the present invention that contain about 2.5% imiquimod, about 3.75% imiquimod or about 5% imiquimod by weight based on the total weight of the formulations are most preferred.

By the term "bioequivalence or bioequivalent", as used herein, it refers to topical semi-solid imiquimod pharmaceutical formulations in which they are pharmaceutically equivalent and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which imiquimod becomes available from such formulations at the site of imiquimod action when administered at the same molar dose under similar conditions, e.g., the rate at which imiquimod can leave such a formulation and the rate at which imiquimod can either cross the stratum corneum and/or become available at the site of action to treat a dermal and/or mucosal-associated condition, e.g., EGWs, AKs or sBCC. In other words, there is a high degree of similarity in the bioavailabilities of two topical semi-solid imiquimod pharmaceutical formulations (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, and/or (c) Health Canada.

By the term "bioavailability or bioavailable", as used herein, it means generally the rate and extent of absorption of imiquimod into the systemic circulation and, more specifically, the rate or measurements intended to reflect the rate and extent to which imiquimod becomes available at the site of action or is absorbed from a topical semi-solid imiquimod pharmaceutical formulation and becomes available at the site of action. In other words, and by way of example, the extent and rate of imiquimod absorption from a topical semi-solid imiquimod pharmaceutical formulation of the present invention as reflected by a time-concentration curve of imiquimod in systemic circulation.

By "pharmaceutical equivalence" or "pharmaceutically equivalent", as used herein, it refers to topical semi-solid imiquimod pharmaceutical formulations of the present invention that contain the same amount of imiquimod, in the same dosage forms, but not necessarily containing the same inactive ingredients, for the same route of administration and meeting the same or comparable compendia or other applicable standards of identity, strength, quality, and purity, including potency and, where applicable, content uniformity and/or stability.

By "therapeutic equivalence" or "therapeutically equivalent", it is meant herein to mean those topical semi-solid imiquimod pharmaceutical formulations which (a) will produce the same clinical effect and safety profile when practicing treatment regimens to treat a dermal and/or mucosal-associated condition, namely, EGWs, AKs or sBCC, in accordance with the present invention and (b) are pharmaceutical equivalents, e.g., they contain imiquimod in the same dosage form, they have the same route of administration; and they have the same imiquimod strength. In other words, therapeutic equivalence means that a chemical equivalent of a topical semi-solid imiquimod pharmaceutical formulation of the present invention (i.e., containing the same amount of imiquimod in the same dosage form) when administered to the same individuals in the same dosage regimen will provide essentially the same efficacy and toxicity.

The topical semi-solid imiquimod pharmaceutical formulations, such as the topical imiquimod pharmaceutical creams, according to the present invention can be applied to any suitable location, for example, applied topically to dermal and/or mucosal surfaces. In the case of dermal application, for example, depending on the imiquimod concentration, formulation composition, and dermal surface, the therapeutic effect of imiquimod may extend only to the superficial layers of the dermal surface or to tissues below the dermal surface. Thus, another aspect of the present invention is directed to a method for the treatment of a dermal and/or mucosal-associated condition comprising applying to skin one of the imiquimod creams via a pump system of the present invention. As used herein, a "dermal and/or mucosal-associated condition" means an inflammatory, infectious, neoplastic or other condition that involves a dermal and/or mucosal surface or that is in sufficient proximity to a dermal and/or mucosal surface to be affected by a therapeutic agent topically applied to the surface. Examples of a dermal and/or mucosal-associated condition include warts, atopic dermatitis, postsurgical scars, lesions caused by a herpes virus, and epidermal neoplasias, such as for example actinic keratosis, pre-actinic keratosis lesions, malignant melanomas, basal cell carcinoma, and squamous cell carcinoma.

In some embodiments, the topical semi-solid imiquimod pharmaceutical formulations, e.g., topical imiquimod pharmaceutical creams, are particularly advantageous for use with the pump systems of the present invention for dermal and/or mucosal application for a period of time sufficient to obtain a desired therapeutic effect without undesired systemic absorption of the imiquimod.

In view of the above, it should be understood by those versed in this art that the present invention contemplates pump systems and methods for storing and dispensing consistent and uniform unit dose amounts of an effective topical semi-solid imiquimod pharmaceutical formulation, and more particularly to pump systems, pre-filled with any effective topical semi-solid imiquimod pharmaceutical formulation, and methods for delivering a precisely measured unit dose amount of any effective topical semi-solid imiquimod pharmaceutical formulation, and still more particularly to pump systems pre-filled with an effective topical semi-solid imiquimod pharmaceutical formulation, and methods for using a controlled delivery pump to store and dispense multiple unit doses of an effective topical semi-solid imiquimod pharmaceutical formulation for use in treating dermal and mucosal-associated conditions, such as, EGWs, AKs and sBCC. It should therefore be understood by those versed in this art that the present invention also contemplates pump systems pre-filled with an effective topical semi-solid imiquimod pharmaceutical formulation that is bioequivalent, pharmaceutically equivalent and/or therapeutically equivalent to, for example, Aldara® (imiquimod) 5% cream, Zyclara® (imiquimod) 3.75% cream or a 2.5% imiquimod cream or any imiquimod formulation set forth herein, or which meets or has the same imiquimod bioavailability as, for example, Aldara® (imiquimod) 5% cream, Zyclara® (imiquimod) 3.75% cream, or a 2.5% imiquimod cream or any other imiquimod formulation set forth herein, as defined by the FDA, the C.F.R. and/or Health Canada.

For ease of description, the components of this invention are described in an upright operating position, and terms such as upper, lower, front, rear, horizontal, etc., are used with reference to this position. It will be understood, however, that the components of this invention may be manufactured, stored, transported, used and sold in an orientation other than the positions described herein.

FIGs. illustrating the components show some mechanical elements that are known and will be recognized by one skilled in the art. The detailed descriptions of such elements are not necessary to an understanding of the invention, and accordingly, are herein presented only to the degree necessary to facilitate an understanding of the novel and unique features of the present invention.

Referring now to FIG. 1, which illustrates a dispensing package which has been constructed in accordance with a preferred embodiment of the present invention and is designated generally by the reference numeral 10. As will be discussed herein below, package 10 is specially adapted for storing and dispensing unit doses of a topical semi-solid imiquimod pharmaceutical formulation, such as an imiquimod cream formulation.

The dispensing package 10 includes a dispensing head 20 having a projecting, finger-operable pump 22 (see FIGS. 3 and 4) and an external actuator button or plunger 24. The pump 22 is a non-venting type that has a pump chamber in which is disposed a pressurizing piston that can be actuated by pressing down on plunger 24, so as to dispense a quantity of the fluid product from a dispensing orifice or self-closing slit 26, which will be described in greater detail herein below.

An optional cover or cap 40 may be releasably mounted over dispensing head 20. The cap 40 is shown as molded from a substantially transparent material. However, in many applications, the cap 40 is preferably made from any suitable opaque material.

The dispensing package 10 includes a tubular structure or hollow body 50 for containing the imiquimod cream. The hollow body 50 is illustrated in the figures as being made from a substantially transparent material, such as a transparent thermoplastic material. However, in many applications, the body is preferably made from any suitable opaque material.

The body 50 most typically would have a circular, transverse cross section. However, the hollow body 50 may have an oval shape, or some other shape, wherein the internal, transverse cross section is substantially uniform along most of its length.

Figure 2:
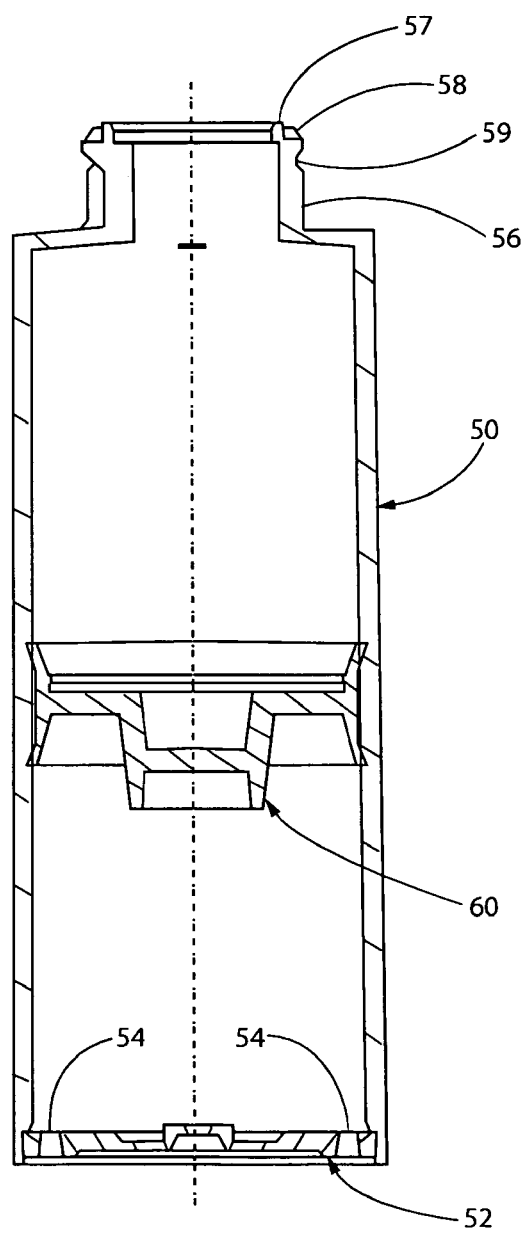
FIG. 2 is a cross-sectional view of a lower or first subassembly of the dispensing package of FIG. 1, which includes a hollow body along with the take-up piston and base closure member.

As shown in FIG. 2, the bottom of the hollow body 50 has an open end which is normally closed by a base closure member 52, which defines one or more apertures 54. The closure member 52 has a transverse cross-section corresponding generally to the transverse cross section of the hollow body 50. The closure member 52 is typically secured to the bottom of the hollow member 50 by means of a snap-fit engagement, by adhesive, or by other suitable means. However, prior to securing the closure member 52 to the hollow body 50, a follower or take-up piston 60 is inserted into the lower, open end of the hollow body 50. The piston sealingly engages the interior surface of the hollow body 50 and is adapted to slidingly move axially upwardly in the hollow body 50. The piston 60 can thus function as a take-up piston for moving toward the pump 22 at the upper, discharge end of the hollow body 50.

The take-up piston 60 moves toward the pump 22 at the discharge end of the body 50 in response to the discharge of any amount of fluid, such as imiquimod cream, from the body 50 so as to decrease the internal volume of the body 50 by an amount equal to the volume of the amount of fluid product which is discharged, i.e., the unit-dose amount. The movement of the piston 60 is effected by the atmospheric pressure of the ambient air which acts against the exterior, bottom surfaces of the piston 60. It will be appreciated that the vent passages 54 in the bottom end closure member 52 insure that the ambient atmosphere will be in continuous contact with the exterior of the piston 60 regardless of how far the piston 60 travels up in the hollow body 50.

The particular design and configuration of the take-up piston 60 are matters of design choice consistent with the configuration used for the hollow body 50. Any suitable conventional or special piston design may be employed. The details of the design per se of such a piston 60 form no part of the present invention. It should be noted that the initial position of the piston within the hollow body 50 is dictated by the total amount of imiquimod cream to be supplied to the patient based on the anticipated dosing regimen. For example, if it is desired to dispense to the patient 15 g of imiquimod cream, the piston would be initially located lower than the setting for 7.5 g of cream.

The upper, discharge end of the body 50 defines a reduced-diameter neck 56. The upper end of the neck defines an external, peripheral shoulder 58. The side of the neck defines an annular, outwardly open groove 59. The distal end of the neck 56 defines an upwardly projecting, annular rim 57 at the inside diameter of the shoulder 58. In a preferred embodiment, the hollow body 50 is injection molded from a suitable thermoplastic material.

The hollow body 50, along with the take-up piston 60 and base closure member 52, may be characterized as the lower subassembly or first subassembly. However, in some applications, the base closure member 52 may be omitted altogether from the first, or lower, subassembly. In any event, after the lower subassembly has been assembled, it can be filled with the imiquimod cream, and then the additional package components, comprising an upper subassembly or second subassembly as described below, are installed on the filled, first subassembly.

Figure 3:
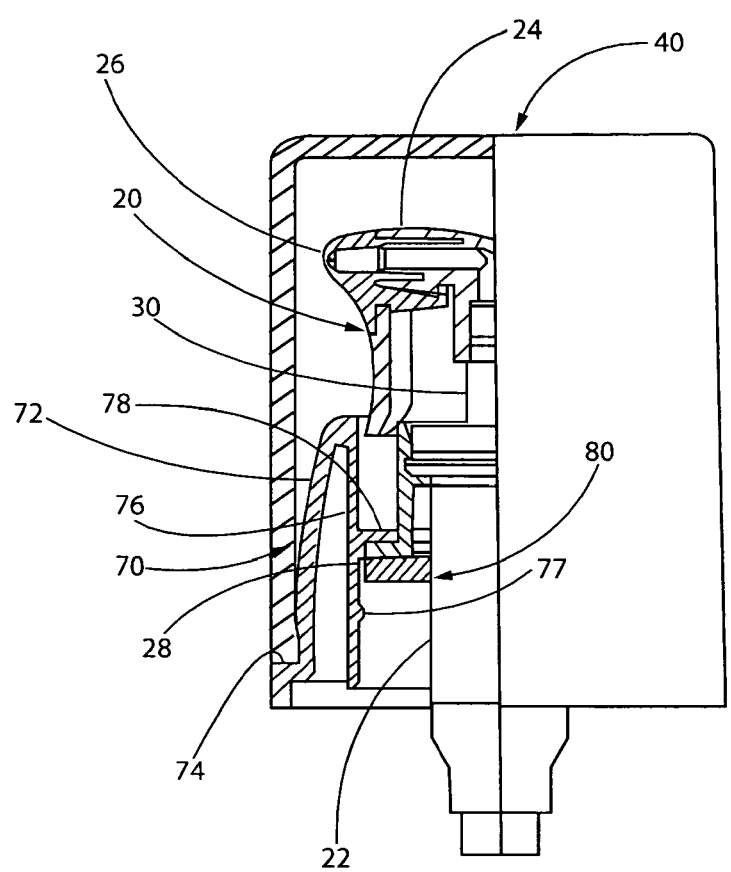
FIG. 3 is a partial cross-sectional view of an upper or second subassembly of the dispensing package of FIG. 1, which includes a dispensing head, a finger-operable pump, a holding member and a cap.

Referring now to FIG. 3, there is illustrated the second subassembly or upper subassembly, which is designed for being mounted to the lower subassembly and comprises at least three components; a finger operable pump 22, a dispensing head 20; and a holding member 70. The dispensing head 20 may be regarded as part of the pump 22. Additional components are also preferably included in the upper subassembly, and such additional components may include a gasket 80 (FIG. 4) and the cap or cover 40 (FIG. 3).

Figure 4:
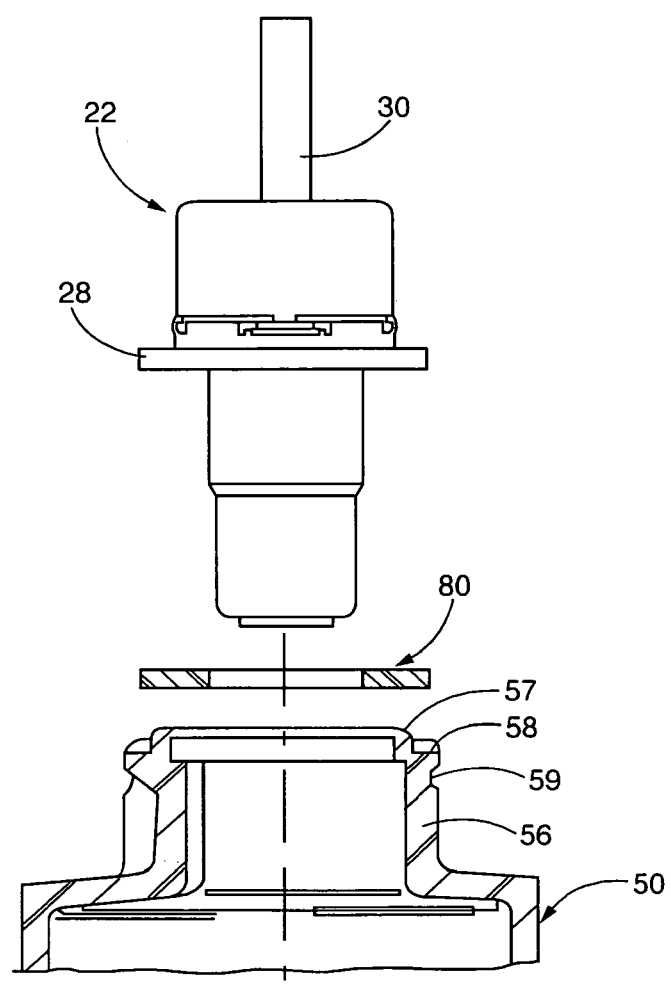
FIG. 4 provides a side elevational view of the finger-operable pump of the upper subassembly, and a cross-sectional view of an o-ring gasket and the hollow body associated with the lower subassembly.

The exterior of the pump 22 is designed to be mounted within the holding member 70, along with the gasket 80 if the gasket is employed. Specifically, the pump 22 has a radially extending mounting flange 28 (FIGS. 3 and 4). The pump 22 may also include one or more bosses or ribs (not shown) which are spaced above the pump flange 28 to define an annular recess between the flange 28 and the ribs and can be used to secure the pump 22 to the holding member 70.

The internal pumping mechanism of the pump 22 may be of any appropriate conventional or special non-venting design. Typically, a conventional, non-venting pump (airless), such as the pump 22 illustrated in the figures, has an interior chamber (not visible) which has a check valve at the lower end and in which is disposed a pressurizing piston (not visible). The pressurizing piston is arranged to cooperate with a hollow stem 30 which extends out through the top of the body of the pump 22 and which is received within the pump actuator button 24.

The stem 30 and the piston within the pump body can move downwardly together in the pump chamber, but the hollow stem 30 can also move for some distance separately relative to the piston, so as to establish communication through the hollow stem 30 between the pump chamber and the actuator button 24. One or more springs (not visible in the figures) act against the piston and/or stem 30 inside the pump body to bias the piston, stem 30, and actuator button 24 upwardly to an elevated rest position when finger pressure is released. As will be discussed in more detail herein below, when the actuator button 24 is pressed, an unit-dose amount of product is dispensed from the pump 22.

One conventional non-venting pump that may be employed in accordance with the present invention is the pump designated EV09/240 and sold by Valois S.A., 50 Avenue de L'Europe, 78160 Marly le roi, France. It will be appreciated, however, that the detailed design and operation of the internal components of such a pump, which may be employed for the pump 22 described herein, form no part of the present invention.

The holding member 70 includes a peripheral, convex shroud 72 providing a pleasing, external configuration. The bottom of the shroud 72 has a laterally projecting flange or shoulder 74. At four locations around the shroud 72 above the flange 74, there are small, outwardly projecting protuberances (not shown) which are adapted to establish a snap-fit engagement in an annular groove formed in the interior bottom of the cap or cover 40. The cap or cover 40 and/or the lower portion of the holding member shroud 72 are resiliently deflectable, so as to accommodate relative movement between the cap 40 and shroud 72 as the cap 40 is installed on the package. The cap 40 and/or shroud 72 deflect sufficiently so that the cap bead can be located below, and adjacent, the protuberances of the holding member shroud 72. This confronting relationship establishes the snap-fit engagement.

Projecting downwardly from the shroud 72 of the holding member 70 is an annular sleeve 76. See FIG. 3. The sleeve 76 defines an opening, bore, or passage for accommodating the annular neck 56 of the hollow body 50 and for accommodating the upwardly projecting portion of the pump 22.

An annular flange 78 extends radially inwardly from the holding member annular sleeve 76 for engaging the upper surface of the pump flange 28. See FIG. 3. The sleeve 76 also includes an inwardly extending bead 77 for being received in the annular groove 59 defined in the hollow body neck 50.

Typically, the pump 22 is initially disposed in the holding member 70, along with the gasket 80, if employed. To this end, the installation is accomplished with the pump actuator 24 initially removed from the pump. Relative movement between the pump 22 and the holding member 77 is effected so as to introduce the pump into the holding member 70 from the bottom end of the holding member.

As noted above, prior to mounting the two subassemblies together, the lower subassembly is filled with the topical semi-solid imiquimod pharmaceutical formulation, such as an imiquimod cream formulation. This can be conveniently done pursuant to a conventional or special filling process which is typically performed under vacuum. Preferably, vacuum (i.e., a reduced pressure) is created by a suitable vacuum system around the body 50. The air below the piston 60 within the body 50 is evacuated through the vent holes/apertures 54 in the base closure member 52 of the body 50. Then the fluid product is discharged from a filling machine into the hollow body 50 through the opening in the body neck 56. Next, with vacuum still enveloping the components, the upper subassembly (comprising the pump 22, holding member 70, gasket 80 if employed, and cap 40 if employed) is moved into position on the lower subassembly hollow body 50 so as to establish the snap-fit engagement between the hollow body 50 and holding member 70.

The particular process and detailed operation of filling the body 50 and mounting the upper subassembly on the lower subassembly form no part of the present invention.

When the two subassemblies are properly mounted together as shown in FIG. 1, the pump flange 28 urges the gasket 80 into sealing engagement with the upper end of the body neck rim 57. However, depending upon the materials employed in the construction of the pump 22 and/or body rim 57 or neck 56, the gasket 80 may either be omitted altogether or be included as a unitary part of either the pump flange 28 or the upper end of the body neck 56.

The set of components provided according to the present invention can be readily manufactured from material which is compatible with the imiquimod cream. Provided below are the results of a stability studies which have been conducted to ensure certain polymeric materials are compatible with an imiquimod cream.

The set of components can be readily assembled to provide a compact package which is clean, safe, reliable, simple and easy-to-use to dispense consistent and uniform unit-dose amounts of a topical semi-solid imiquimod pharmaceutical formulation, such as an imiquimod cream, to treat a dermal and/or mucosal-associated condition. Except for the removable cap 40, the components are not readily disassembled, and the completed package protects a topical semi-solid imiquimod pharmaceutical formulation from degradation, oxidation, and/or external contaminants.

Figure 5:
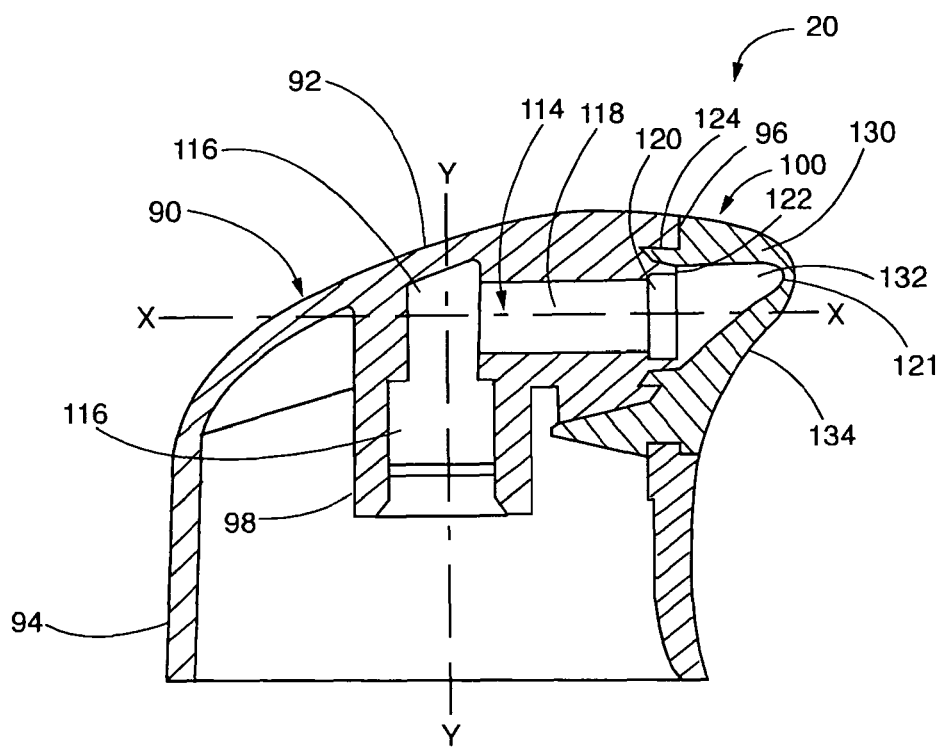
FIG. 5 is a cross-sectional view of the dispensing head used in the dispensing package of FIG. 1, the dispensing head including a body portion and a shutter member.
Figure 6:
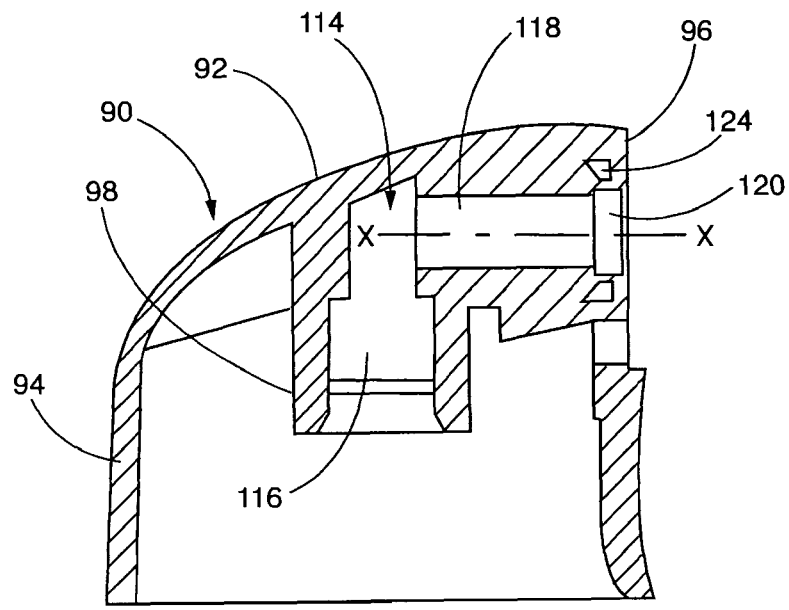
FIG. 6 is a cross-sectional view of the body portion of the dispensing head of FIG. 5.
Figure 7:
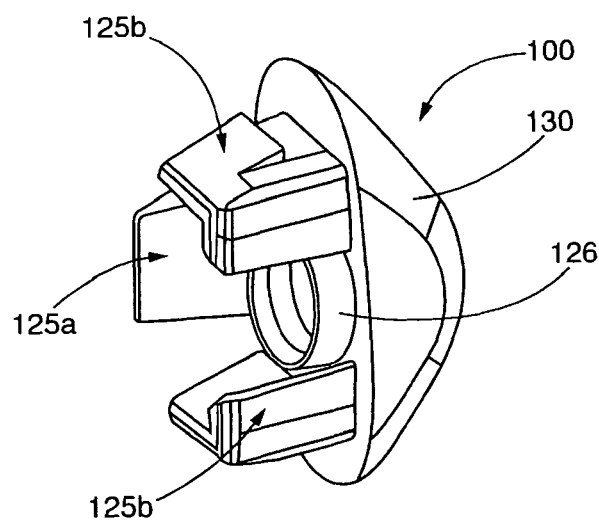
FIG. 7 is a perspective view taken from the rear side of the shutter member of the dispensing head of FIG. 5.

Referring now to FIG. 5, it provides a cross-sectional view of dispenser head 20. In the embodiment shown in the FIGs., the dispenser head 20 is made up of two component elements, namely a body 90, FIG. 6, and a shutter 100, FIG. 7. The two elements may be made by injecting suitable plastics materials into appropriate molds. The body 90 is preferably made of a plastics material that is harder or stiffer than the shutter 100.

The body 90, which is preferably integrally molded in one piece, comprises a push top wall 92 which serves a pusher surface against which one or more fingers of one hand can be applied and can exert a pressing force. In this example, the top wall 92 has a complex shape that is both rounded and inclined. This is an ergonomic shape for the position of a finger with the tip phalanx of the finger placed on the highest portion of the top wall 92. In addition, the body 90 forms a peripheral side skirt 94 which extends from the top wall 92 downwards. The skirt 94 has a configuration that is also complex, but that is substantially cylindrical.

Where the top wall 92 is at its highest, the skirt 94 forms a join surface 96 that is exactly plane in this example. The join surface 96 is provided with plurality of openings or slots, as is described below. Shutter 100, described below, is designed to be mounted on the body 90 at the join surface 96.

The body 90 of dispensing head 20 internally defines a connection sleeve 98 serving to receive the top end of the hollow stem 30 of pump 22. The socket formed by the connection sleeve 98 may be of the force-fitting type or of the snap-fastening type. The rod-receiving socket is extended by a dispensing duct 114 which defines an axial inlet 116. This inlet is disposed on a vertical longitudinal axis Y which coincides with the axis of the dispenser member and of its actuating rod. Naturally, the inlet 116 is open facing downwards so as to communicate with the socket formed by the connection sleeve 98 in which the top end of the hollow stem 30 of pump 22 is to be engaged.

In many cases, the body 90, and more generally the dispenser head 20, is mounted to rotate about said vertical axis Y. The dispensing duct 114 also forms a radial passageway 118 which opens out at the join surface 96 via an outlet 120. The outlet 120 and the passageway 118 that connects the inlet 116 to the outlet 120 extend along a dispensing or outlet axis X. The outlet axis X extends substantially perpendicularly to the vertical longitudinal axis Y. However, the axis X may extend slightly or significantly upwards or downwards relative to the axis Y.

Join surface 96 includes a circular groove 124 which extends from the join surface 96 into the body 90 in substantially the same direction as the outlet axis X. The groove 124 thus forms a sort of annular trench whose depth extends horizontally.

As explained below, the function of said groove 124 is to provide sealing with the shutter 100. The shutter 100 forms a dispensing spout 130 internally forming an outlet or dispensing chamber 132. The chamber 132 terminates at self-closing slit 26 that forms a dispensing orifice. The self-closing slit 28 has edges that are in touching leak-tight contact in the rest position, i.e., whenever the chamber 132 does not contain any fluid subjected to a pressure higher than a threshold pressure making it possible to separate the edges of the slit and thus to open the self-closing slit 28. In the embodiment shown in the FIGS., the bottom surface 134 of the dispensing chamber 132 is inclined upwards and thus constitutes a convergence wall suitable for directing the fluid under pressure towards the dispensing orifice.

Fixing catches 125*a* and 125*b* extend from the rear of the shutter 100 and secure the shutter to the body 90 in snap-fit engagement. In the non-limiting embodiment, there are a bottom catch 125*a* and two side catches 125*b*. The three catches extend from the rear of the shutter 100 around the sealing lip 126.

The shutter 100 is fitted to the body 90 by causing the catches 125A and 125*b* to penetrate into respective holding recesses formed in the body 90. When the shutter 100 is fitted to the body 90, the sealing lip 126 is caused to be pressed into the groove 124 so as to come into leak-tight contact with the two side walls of said groove, and advantageously also with the end-wall thereof. Leak-tight contact is thus obtained at three points that have very good sealing quality, since the lip is in tight-fitting engagement between the two facing side walls.

Once the package is filled, the priming of the actuator allows the imiquimod product to fill into the pump 22 and the dispensing duct 114. Once the pump 22 is fully primed with imiquimod product, each additional actuation will cause a precise dosage amount of the imiquimod product to be dispensed. Moreover, each actuation causes the take-up piston 60 to rise until ultimately, the piston reaches the top of the package and empties and remaining product.

A series of trials were conducted to determine the suitability of the dispensing device for use with topical imiquimod pharmaceutical cream. A series of pump systems were evaluated for 2.5%, 3.75% and 5% w/w imiquimod creams targeting a pump system that could deliver approximately 250 mg of the product per actuation mimicking the dosage/delivery of the commercially available single use 250 mg packets or sachets.

Two pump system constructions were evaluated: Albion EV09/1500-30 mL (hereinafter "Albion") and VP39/70 pl-15 mL Digital Actuator Nova Pump EV09/150 ("Nova"). Like the previously described dispensing package, the Albion pump system includes a tubular base member in which a topical imiquimod pharmaceutical cream is retained. The Nova pump system stores a topical imiquimod pharmaceutical cream in an aluminum pouch.

One difference between these two pumps are how they are designed to operate and the product contact materials used to manufacture the respective pump components. In order to determine which, if either, pump design and product contact components are best suited for consistently and uniformly dispensing precise unit-dose amounts of the 2.5%, 3.75% and 5% w/w imiquimod pharmaceutical creams, even after use interruption and storage for a period of time, a series of performance tests, filling trials and stability studies are conducted.

While the topical semi-solid imiquimod pharmaceutical formulations of the present invention can be formulated into any form known to the art, such as a cream, an ointment, a gel or a lotion, it should be understood that such semi-solids may be packaged into the multi-dose, pump systems of the present invention for treatment of a dermal and/or mucosal-associated condition, such as EGWs, AKs or sBCC. A packaged amount of a topical semi-solid imiquimod pharmaceutical formulation contemplated by the present invention includes any suitable packaged amount, for completing one or more treatment regimens for treating a dermal and/or mucosal-associated condition, such as EGWs, AKs or sBCC, such as an amount between about 5 grams and 30 about grams, more preferably about 5 grams, about 7.5 grams, about 10 grams, about 12.5 grams, about 15 grams, about 17.5 grams, about 20 grams, about 22.5 grams, about 25 grams, about 27.5 grams, about 30 grams or more, and more preferably about 7.5 grams and about 15 grams. An actuated unit-dose amount of a topical semi-solid imiquimod formulation that may be dispensed from a pump system of the present invention includes any effective unit-dose amount for treating a prescribed dermal and/or mucosal condition discussed herein above, such as an actuated unit dose amount of about 125 mg to about 500 mg or more, and preferably about 150 mg, about 175 mg, about 200 mg, about 225 mg, about 240 mg, about 250 mg, about 275 mg, about 300 mg, about 325 mg, about 350 mg, about 375 mg, about 400 mg, about 425 mg, about 450 mg, about 500 mg or more, and more preferably about 240 mg or about 250 mg per actuation.

As indicated herein above, the present invention also contemplates bioequivalent or interchangeable topical semi-solid imiquimod pharmaceutical formulations. By way of an example, bioequivalent or interchangeable dosage strength topical semi-solid imiquimod pharmaceutical formulations, as contemplated by the present invention, include topical semi-solid imiquimod pharmaceutical formulations that have respective comparable in-vivo serum profiles, i.e., wherein the in-vivo parameters are either the same or may vary up to about ±25% or more, when such a 2.5%, 3.75% or 5% topical semi-solid imiquimod pharmaceutical formulation is topically administered daily to the same individual in the same dosage regimen in accordance with dosage regimens described herein to treat a dermal and/or mucosal-associated condition, such as external or perianal warts, actinic keratosis or superficial basal cell carcinoma. In other words, two or more topical semi-solid imiquimod pharmaceutical formulations having the same imiquimod concentration but different formulations will be considered bioequivalent or interchangeable if their respective in-vivo parameters are either the same or vary up to about ±25% or more, when such topical semi-solid imiquimod pharmaceutical formulations are topically administered daily to an individual in the same dosage regimen in accordance with dosage regimens described herein to treat a dermal and/or mucosal-associated condition, such as EGWs, AKs or sBCC carcinoma.

By way of an example, bioequivalent or interchangeable 3.75% dosage strength topical semi-solid imiquimod pharmaceutical formulations, as contemplated by the present invention, include topical semi-solid 3.75% imiquimod pharmaceutical formulations that have comparable in-vivo serum profiles, i.e., wherein the following in-vivo parameters are either the same or may vary up to about ±25% or more, when approximately 500 mg of each such formulation (about 18.75 mg imiquimod) or less is applied daily for 21 days to an AK treatment area of about 200 cm2 on the face or balding scalp between about day 8 and day 14 and, selected from one or more of the following in-vivo serum profiles:

(a) a Day 21 $T_{max}$ of from about 4 hours to about 16 hours and preferably a mean $T_{max}$ of about 7.4 hours with a standard deviation ("SD") of about 3.5, a median $T_{max}$ of about 9 hours and a geometric mean $T_{max}$ of about 6.6 hours and a coefficient of variation ("CV") of about 48%;

(b) a Day 21 $C_{max}$ of from about 0.07 to about 0.6 ng/ml and preferably a mean $C_{max}$ of about 0.3 ng/ml with a standard deviation of about 0.16, a median $C_{max}$ of about 0.35 and a geometric mean $C_{max}$ of about 0.27 ng/ml and a coefficient of variation of about 49%;

(c) a Day 21 $T_{1/2}$ of from about 9.7 to about 84 hours and preferably a mean $T_{1/2}$ of about 29.3 hours with a standard deviation of about 17, a median $T_{1/2}$ of about 25.6 hours and a geometric mean $T_{1/2}$ of about 26 hours and a coefficient of variation of about 58%;

(d) a Day 21 $AUC_{10\text{-}24}$ of from about 1.1 to about 12 ng·hr/ml and preferably a mean $AUC_{0\text{-}24}$ of about 6 ng·hr/ml with a standard deviation of about 3, a median $AUC_{0\text{-}24}$ of about 7 ng·hr/ml and a geometric mean $AUC_{0\text{-}24}$ of about 5 ng-hr/ml and a coefficient of variation of about 52%;

(e) a Day 21 $\lambda z$ of from about 0.008 $hr^{-1}$ to about 0.07 $hr^{-1}$ and preferably a mean $\lambda z$ of about 0.03 $hr^{-1}$ with a standard deviation of about 0.01, a median $\lambda z$ of about 25.6 $hr^{-1}$ and a geometric mean $\lambda z$ of about 0.03 $hr^{-1}$ and a coefficient of variation of about 49%;

(f) a Day 21 $C_{min}$ of from about 0.06 to about 0.4 and preferably a mean $C_{min}$ of about 0.20 with an SD of about 0.11, a median $C_{min}$ of about 0.19 and a geometric mean $C_{min}$ of about 0.17 and a coefficient of variation of about 55%;

(g) at Day 14/7 (a ratio of the trough concentration at Day 14 over the trough concentration at Day 7), a trough concentration geometric mean ratio of about 1.09 with a 90% confidence interval ("CI") within a range of between about 0.8 and about 1.5;

(h) at Day 21/14 (a ratio of the trough concentration at Day 21 over the trough concentration at Day 14), a trough concentration geometric mean ratio of about 1.33 with a 90% confidence interval ("CI") within a range of between about 0.9 and about 1.9;

(i) at Day 22/21 (a ratio of the trough concentration at Day 22 over the trough concentration at Day 21) a trough concentration geometric mean ratio of about 0.93 with a 90% confidence interval ("CI") within a range of between about 0.6 and about 1.3;

(j) a mean peak imiquimod serum concentration of about 0.323 ng/ml at Day 21;

(k) a Day 21 RAUC of from about 1 to about 7 and preferably a mean RAUC of about 4 with a standard deviation of about 2, a median RAUC of about 3.5 and a geometric mean RAUC of about 3.3 and a coefficient of variation of about 56%;

(l) a Day 21 $RC_{max}$ of from about 0.5 to about 5 and preferably a mean $RC_{max}$ of about 3 with a standard deviation of about 1.5, a median $RC_{max}$ of about 2.7 and a geometric mean $RC_{max}$ of about 2.4 and a coefficient of variation of about 54%;

(m) a Day 21 $L\lambda z_{eff}$ of from about 0.006 $hr^{-1}$ to about 0.08 $hr^{-1}$ and preferably a mean $L\lambda z_{eff}$ of about 0.02 $hr^{-1}$ with a standard deviation of about 0.02, a median $L\lambda z_{eff}$ of about 0.01 $hr^{-1}$ and a geometric mean $L\lambda z_{eff}$ of about 0.16 $hr^{-1}$ and a coefficient of variation of about 97%; and (n) a Day 21 $T^{1/2}_{eff}$ of from about 8 hr to about 110 hr and preferably a mean $T^{1/2}_{eff}$ of about 55 hr with a standard deviation of about 36, a median $T^{1/2}_{eff}$ of about 50 hr and a geometric mean $T^{1/2}_{eff}$ of about 42 $hr^{-1}$ and a coefficient of variation of about 66%.

By way of another example, bioequivalent or interchangeable topical semi-solid 3.75% imiquimod pharmaceutical formulations contemplated by the present invention include topical semi-solid 3.75% imiquimod pharmaceutical formulations that, when approximately 250 mg of each such topical semi-solid imiquimod pharmaceutical formulation' (about 9.375 mg imiquimod) or less is applied daily for 21 days to EGWs in the genital/perianal area with a total wart area of greater than or equal to 100 $mm^2$, provide a comparable in-vivo serum profile selected from one or more of the following:

(a) a Day 21 mean $T_{max}$ of about 9.7 hours with a standard deviation ("SD") of about 4.0, a median $T_{max}$ of about 12 hours and a geometric mean $T_{max}$ of about 8.3 hours and a coefficient of variation ("CV") of about 41%;

(b) a Day 21 mean $C_{max}$ of about 0.488 ng/ml with a standard deviation of about 0.368, a median $C_{max}$ of about 0.45 and a geometric mean $C_{max}$ of about 0.39 ng/mL and a coefficient of variation of about 75%;

(c) a Day 21 $T_{1/2}$ of from about 6.8 to about 54 hours and preferably a mean $T_{1/2}$ of about 24.1 hours with a standard deviation of about 12, a median $T_{1/2}$ of about 22.8 hours and a geometric mean $T_{1/2}$ of about 21 hours and a coefficient of variation of about 51%;

(d) a Day 21 $AUC_{0-24}$ of from about 1.9 to about 14 ng-hr/mL and preferably a mean $AUC_{0-24}$ of about 6.8 ng·hr/mL with a standard deviation of about 3.6, a median $AUC_{0-24}$ of about 6.6 ng·hr/mL, and a geometric mean $AUC_{0-24}$ of about 5.8 ng-hr/mL and a coefficient of variation of about 53%;

(e) a day 21 $\lambda z$ of from about 0.013 $hr^{-1}$ to about 0.102 $hr^{-1}$ and preferably a mean $\lambda z$ of about 0.037 $hr^{-1}$ with a standard deviation of about 0.02, a median $\lambda z$ of about 0.03 $hr^{-1}$ and a geometric mean $\lambda z$ of about 0.03 $hr^{-1}$ and a coefficient of variation of about 60%;

(f) a Day 21 $C_{min}$ of from about 0.025 to about 0.47 and preferably a mean $C_{min}$ of about 0.158 with an SD of about 0.121, a median $C_{min}$ of about 0.14 and a geometric mean $C_{min}$ of about 0.11 and a coefficient of variation of about 77%;

(g) at Day 14/7 (a ratio of the trough concentration at Day 14 over the trough concentration at Day 7), a trough concentration geometric mean ratio of about 1.13 with a 90% confidence interval ("CI") within a range of between about 0.7 and about 1.7;

(h) at Day 21/14 (a ratio of the trough concentration at Day 21 over the trough concentration at Day 14), a trough concentration geometric mean ratio of about 0.84 with a 90% confidence interval ("CI") within a range of between about 0.5 and about 1.3;

(i) at Day 22/21 (a ratio of the trough concentration at Day 22 over the trough concentration at Day 21) a trough concentration geometric mean ratio of about 1.12 with a 90% confidence interval ("CI") within a range of between about 0.7 and about 1.6;

(j) a mean peak imiquimod serum concentration of about 0.488 ng/mL at Day 21;

(k) a Day 21 RAUC of from about 0.6 to about 7 and preferably a mean RAUC of about 2.2 with a standard deviation of about 1.8, a median RAUC of about 1.8 and a geometric mean RAUC of about 1.7 and a coefficient of variation of about 81%;

(l) a Day 21 $RC_{max}$ of from about 0.5 to about 5 and preferably a mean $RC_{max}$ of about 2.3 with a standard deviation of about 1.6, a median $RC_{max}$ of about 1.7 and a geometric mean $RC_{max}$ of about 1.8 and a coefficient of variation of about 70%;

(m) a Day 21 $L\lambda z_{eff}$ of from about 0.006 $hr^{-1}$ to about 0.09 $hr^{-1}$ and preferably a mean $L\lambda z_{eff}$ of about 0.04 $hr^{-1}$ with a standard deviation of about 0.03, a median $L\lambda z_{eff}$ of about 0.03 $hr^{-1}$ and a geometric mean $L\lambda z_{eff}$ of about 0.03 $hr^{-1}$ and a coefficient of variation of about 69%;

(n) a Day 21 $T^{1/2}_{eff}$ of from about 8 hr to about 111 hr and preferably a mean $T^{1/2}_{eff}$ of about 31 hr with a standard deviation of about 30, a median $T^{1/2}_{eff}$ of about 22 hr and a geometric mean $T^{1/2}_{eff}$ of about 23 $h^{-1}$ and a coefficient of variation of about 97%;

(o) a Day 21 $C_{max}$ in female patients about 61% higher in female subjects than in male subjects (0.676 versus 0.420 ng/mL) and total systemic exposure AUC 0-24 8% higher in female subjects than in male subjects (7.192 versus 6.651 ng-hr/mL) when data is not dose normalized;

(p) a Day 21 $C_{max}$ in female patients about 35% higher than in male subjects (0.583 versus 0.431 ng/mL) and AUC 0-24 about 6% lower in female subjects than in male subjects (6.428 versus 6.858 ng-hr/mL) when using dose normalization to adjust for differences in dosage and reported without subjects who missed an application of study drug during the last week of dosing; and/or (q) a median $T_{max}$ occurring approximately twice as quickly in female subjects (about 6.50 hours) as in male subjects (about 12.0 hours).

In accordance with the present invention, mean peak serum concentrations are achieved with the topical semi-solid imiquimod pharmaceutical formulations of the Examples (see also Attachments I-XV) when topically applied as discussed herein throughout. For example, a mean peak serum concentration of about 0.488 ng/mL is achieved with a 3.75% dosage strength imiquimod pharmaceutical formulation 202 of Example 21 after about 9.4 mg of imiquimod is applied to the affected treatment area each day for up to 8 weeks.

Examples of various embodiments of the present invention will now be further illustrated with reference to the following examples. Thus, the following examples are provided to illustrate the present invention, but are not intended to be limiting thereof. Parts and percentages are by weight unless otherwise specified. Examples of topical imiquimod cream and ointment compositions contemplated by the present invention are described in U.S. Pat. No. 4,689,338 and U.S. Pat. No. 5,238,944, which are incorporated herein by reference in their entireties. Percent modifications for, e.g., imiquimod and vehicle, to generate imiquimod formulations as described herein are likewise contemplated by the present invention. In addition, the formulations described and disclosed in U.S. Pat. No. 7,655,672, U.S. Patent Publication No. 2007/0123558, Ser. No. 11/276,324, U.S. Patent Publication No. 2007/0264317, U.S. Ser. No. 11/433,471, U.S. Patent Publication No. 2007/0900550 and PCT Publication No. WO2008098232 (A1), are also contemplated by the present invention and are incorporated herein by reference in their entireties.

EXAMPLE 1

Pump Performance Attribute Tests

A series of pump performance attribute testing is conducted to assess the best pump design for, for example, by weight 2.5%, 3.75% and 5% w/w imiquimod creams, such as described in Examples 16 and 20. The performance attributes tests and respective acceptance criteria are described below.

A. Priming:

The purpose of this test is to determine the number of actuations necessary to start observing delivery of the product dispensed from the actuator. Additionally, the number of pump depressions, i.e., the number of depressions/actuations required until the first full dose is delivered is also monitored.

Acceptance Criteria:

The number of actuations to start observing delivery of the product dispensed from the actuator must be less than or equal to 5 actuations.

B. Dosage Reproducibility:

The purpose of this test is to measure the doses restituted by the pump and verify the consistency of the dose value with time. Pumps are actuated manually.

Acceptance Criteria:

For each pump, the average of 10 individual dose values must be within about 10% of the pumps nominal value of about 240 mg and each individual dose value must be within about 15% of the pump's nominal value of about 240 mg.

C. Sealing Integrity Under Vacuum:

The purpose of this test is to evaluate the sealing integrity of a specific pump and container configuration when placed under vacuum. The sealing integrity of a pump corresponds to its ability to retain the product in the container and play its role in the closure of the system. Unprimed pump samples are filled with the product to be tested, are positioned horizontally for about 20 minutes at room temperature in a vacuum chamber at about 24" Hg depression.

Acceptance Criteria:

There must be no visual sign of leakage.

D. Weight Loss at Atmospheric Pressure:

The purpose of this test is to evaluate the sealing integrity of each pump and container configuration stored under specific conditions. For this test, filled samples are weighed, stored at specific conditions and then weighed again to measure for any weight loss.

Acceptance Criteria:

Weight loss values must typically not exceed about 0.3% after 4 weeks at room temperature and about 1.0% after about 4 weeks at about 45° C. (based on the total weight of the package).

E. Restitution Rate:

The purpose of this test is to determine the portion of product delivered by a package after the pump can no longer dispense any product and compare it to the quantity of product used to fill the package.

Acceptance Criteria:

The restitution rates depend on the type of package and the type of filling (airless or atmospheric).

F. Dose Through Life:

This test measures the dose restituted by the pump/device mechanism during each actuation until the container is empty. Devices are manually actuated.

Acceptance Criteria:

The overall average of the dose value must be within about 10% of the pump's nominal dose value of about 240 mg of product. Each individual dose value must be within about 15% of the pump's nominal dose value. The pump is considered to have met the Dose through life criteria if it provides about 240 mg of product and if it meets restitution rate criteria.

G. Loss of Prime:

The purpose of this test is to evaluate the ability of a pump to retain its prime over a specific storage time. The loss of prime is defined as the amount of product that returns from the dose chamber back into the container after storage in an upright position. "Shot" weights are measured before and after storage to determine the loss of prime and the percentage of dose retained.

Acceptance Criteria:

The pump must retain its prime during storage. The percentage of dose retained (ratio of dose after storage to dose before storage) must be more than about 85% in order to deliver a consistent, uniform and effective dosage amount.

H. Gasket Swelling:

This test measures the change in thickness of the gasket following storage in contact with the product. Relevant sets of gaskets (two gaskets per set) with the same chemical composition and similar thickness are stored at about 45° C. for about 8 weeks containers filled with product to be tested. The samples are stored at about 45° C. at about 1, about 4 and about 8 weeks interval are tested for the thickness of the gaskets at about room temperature. Additionally, the following conditions are observed: gaskets' deformation and color change in product or gaskets; samples will be compared with a control sample.

Acceptance Criteria:

The swelling of the gasket should be not more than about 15%. Also there should be no shrinking and no discoloration of the gasket and the product.

I. Migration:

The purpose of this test is to check that the pigments in a colored plastic material do not migrate into the customer's formulation. After priming, samples will be stored at about 45° C. for about 1 week. On each day, two samples will be actuated and the dispensed bulk will be compared to the control sample. Additionally after about 4 weeks at about 45° C. all samples will be emptied and bulk will be compared to the control sample. The dispensed product will be examined and inspected for the presence of pigments that might have migrated from the actuator or for any color modification of the bulk when compared to the bulk dispensed by the control sample.

Acceptance Criteria:

It is considered that migration has occurred if the presence of colored pigments is observed in the tested product when compared to the product dispensed by the controlled samples.

J. Corrosion of the Metal Components:

The purpose of this test is to assess the compatibility between the active formulation and the pump metal components after being in contact for a specific period of time.

Corrosion of the Pump Metal Components is defined as the oxidation of pump metal components when exposed to the active formulation. Relevant components (spring(s) and stainless steel ball) will be stored in containers in intimate contact with product, at ambient temperature and elevated temperature (about 45° C./75% RH). Components will be inspected at 3 days, 1 week, 2 weeks, 4 weeks, 8 weeks, 12 weeks and 24 weeks. Components are inspected for oxidation on the pump metal components at each time point.

Acceptance Criteria:

The results are verified against the reference sample.

K. Discoloration of Formulation:

The purpose of this test is to assess the compatibility between the product and the pump components after being in contact with the product for a specific period of time. Discoloration of Formulation is defined as the change of color of active formulation when in contact with pump components for a specific amount of time. The components will be stored in containers at ambient temperature and elevated temperature (about 45° C./75% RH). Change of color in the active product will be examined at 3 days, 1 week, 2 weeks, 4 weeks, 8 weeks, 12 weeks and about 24 weeks at Room Temperature and about 45° C./75% RH.

Acceptance Criteria:

The results are verified against the reference sample.

L. Pouch Compatibility (Nova System Only):

The purpose of this test is to verify the compatibility of a pouch foil material with the formulation after 4 weeks of aging at about 45° C. in terms of welding resistance and physical appearance. After aging, each sample will be cut into two 15 mm strip film and a total of 10 test strips is obtained. Strips will be measured for the split force using the dynamometer. Samples will be visually inspected to verify the absence of physical defects such as de-lamination, blistering or spotting.

Acceptance Criteria:

Pull force that is required to split the welded parts of the foil must be about 1.5 Kg minimum and no physical defects are observed after storage for about 4 weeks at 45° C.

EXAMPLE 2

Pump Filling Trials

A series of pump filling trials were conducted at two different facilities. In both facilities the filling process and equipment were identical. In each process, the cream formulation is filled under vacuum into the container barrel using volumetric dose pumps. The barrel and the pump head or upper assembly with the actuator is joined ("snapped on") to the pump body under vacuum. This packaging process enables delivery of a precise quantity of product by depression of the pump mechanism, avoiding any contact with air.

The filling trials as well as any salient observations and conclusions for each trial are described below.

A. Filling Trial #s F008-08 and F009-08 at Facility I

Initial fill trials are conducted on the Albion pump system to determine the capability of the filling equipment to fill the creams and also the flowability of the cream during the filling process. The pump body and the stem are made of polybutylene terephthalate, the actuator is made of polypropylene homopolymer/low density polyethylene and the piston is made of high density polyethylene material.

A fill weight of about 7.5 g and about 15 g are selected for these trial runs. These fill weights correspond to the quantity of cream necessary to provide a full course of therapy to the patient depending on which indication is being treated. The filling trial runs prove that Imiquimod cream about 2.5% w/w (Lot #GJB070) manufactured by 3M, Loughborough, UK, can successfully be packaged using the airless filling process per Valois filling parameters.

The filling trials prove that the about 2.5% w/w cream can be successfully filled into the pumps. However, it is also noted that filling issues causing lower pump delivery values, i.e., shot weight, are caused by air bubbles entrapped in the bulk cream. This problem is corrected by avoiding introduction of air during the transfer of the product from the storage drum to the filling hopper.

All performance tests and physical stability screening data support that the Albion Pump Model Albion 30 ml EV09/150 pl and VP39/70 µl-15 ml Digital actuator can be successfully filled and warrant further development.

B. Filling Trials #s 2027 Through 2324 at Facility II

These series of trials focuses on selecting which Albion and/or Nova Pump Model to commercialize, pump fill overages that are required to ensure a about 7.5 gm and about 15 gm pump delivery, pump actuator size, use of a cocoon tip, and contact materials to be used in each respective pumps. In addition, several of the package presentations are placed on RT and accelerated conditions to help select the most compatible pump design for Imiquimod about 2.5%, about 3.75% and about 5% w/w cream.

The trials and corresponding observations are discussed below:

1.) Filling #s 2022 (about 2.5%) and 2026 (about 3.75%)—about 7.5 g Fill Weight.

Albion 15 ml pump with standard actuator, standard piston and about 150 µl dosing is filled with imiquimod cream about 2.5% w/w (lot #GJJ067) and imiquimod cream about 3.75% w/w (Lot #GJJ068). The piston is made of high density polyethylene and the position of the piston inside the pump is set to deliver about 7.5 g.

The product-components compatibility are satisfactory but the weight loss for about 4 weeks at about RT and loss of prime at about 1 week are not acceptable in both trials.

2.) Filling #s 2023 about (2.5%) and 2027 (about 3.75%)—about 15 g Fill Weight.

Albion 15 ml pump with standard actuator, standard piston and about 150 µl dosing is filled with imiquimod cream about 2.5% w/w (lot #GJJ067) and imiquimod cream about 3.75% w/w (Lot #GJJ068). The piston is made of high density polyethylene and the position of the piston inside the pump was set to deliver about 15 g.

The product-components compatibility is satisfactory but loss of prime at about 2 weeks is not acceptable in both trials.

3.) Filling #s 2024 (about 2.5%)—about 7.5 g Fill Weight.

Nova 15 ml with aluminum pouch pack standard actuator about 150 µl is filled with about 7.5 g of Imiquimod cream about 2.5% w/w (Lot #GJJ067).

During the testing it is observed that the pouch material is delaminating and not suitable for this cream product. It is theorized that the high concentration (about 20%) of isostearic acid in the cream formulation causes the delamination of these pouches.

4.) Filling #s 2025 (about 2.5%)—about 15 g Fill Weight.

Nova 30 ml with aluminum pouch pack standard actuator about 150 μl with pouch is filled with about 15 g of about 2.5% w/w of the cream (Lot #GJJ067).

On testing, it is observed that the pouch material is delaminating and not suitable for this cream product.

5.) Filling #s 2028 (about 3.75%)—about 7.5 g Fill Weight.

Nova 15 ml with aluminum pouch pack standard actuator about 150 μl with pouch is filled with about 7.5 g of about 3.75% of the cream (Lot #GJJ068).

On testing it is observed that the pouch material is delaminating and not suitable for this cream product.

6.) Filling #2029 (about 3.75%)—about 15 g Fill Weight.

Nova 30 ml with aluminum pouch pack standard actuator about 150 μl with pouch is filled with about 15 g of the cream (Lot #GJJ068).

On testing, it is observed that the pouch material is delaminating and not suitable for this cream product.

7.) Filling #2060 (about 5.0%)—about 7.5 g Fill Weight.

Albion 15 ml piston pump with standard actuator dosage about 150 μl with the position of the piston inside the pack set to deliver about 7.5 g is filled with Aldara® Cream 5% w/w (lot #GJF033).

The product-components compatibility is satisfactory but loss of prime at 2 week is not acceptable.

8.) Filling #2061 (about 5.0%)—about 15 g Fill Weight.

Albion 15 ml piston pump with standard actuator dosage about 150 μl with the position of the piston inside the pack set to deliver about 15 g is filled with Aldara® Cream about 5% w/w (lot #GJF033).

The product-components compatibility is satisfactory but loss of prime at about 1 week is not acceptable.

9.) Filling #2062 (about 5%)—about 7.5 g Fill Weight.

Nova 15 ml with aluminum pouch pack standard actuator about 150 μl with pouch is filled with about 7.5 g of Aldara® Cream about 5% w/w (Lot #GJF033).

Delamination of pouch material and loss of prime at about 2 weeks are not acceptable.

10.) Filling #2063 (about 5%)—about 15 g Fill Weight.

Nova 30 ml with aluminum pouch pack standard actuator about 150 μl with pouch is filled with about 15 g of Aldara® Cream about 5% w/w (Lot #GJF033).

Delamination of pouch material and loss of prime at about 2 days are not acceptable.

11.) Filling #2084 (about 2.5%)—about 15 g Fill Weight.

Albion 15 ml EV09/240 μl pump with standard actuator dosage about 240 μl to deliver about 240 mg shot weight is filled with low strength Imiquimod cream about 2.5% w/w (Lot #GJJ067).

All physical test results are acceptable but there is a trend for loss of prime to decrease. However at about 4 weeks, the loss of prime is about 85.2% which is at the lower limit (about 85.0%) of the specification for loss of prime.

12.) Filling #s 2085 (3.75%)—about 15 g Fill Weight.

Albion 15 ml EV09/about 240 μl pump with standard actuator dosage about 240 μl to deliver about 40 mg shot weight is filled with low strength Imiquimod cream about 3.75% w/w (lot #GJJ068).

All the physical test results are acceptable; however loss of prime at 4 weeks testing is at about 78.2% which fails the acceptance criteria limit of about 85.0%.

13.) Filling #2103 (5%)—about 15 g Fill Weight.

Albion 15 ml EV09/about 240 μl pump with standard actuator dosage about 240 μl with the position of the piston inside the pack set to deliver about 15 g is filled with imiquimod cream about 5% w/w (lot #GJF033).

All the physical test results are acceptable but loss of prime at about 4 weeks testing is at about 79.5% and fails the acceptance criteria limit of about 85.0%.

Summary of Trials #s 2022-2103.

Based on the results from trials #2022, 2023, 2024, 2025, 2026, 2027, 2028, 2029, 2060, 2061, 2062, 2063, 2084, 2085 and 2103, there is a potential for failure for loss of prime using the standard actuator. It is theorized that these failures are attributable to the possibility of drying of the cream at the exposed tip of actuator nozzle.

To prevent the potential of drying of the cream and also protect the cream from the atmospheric environment, a pump with shutter or cocoon actuator is investigated. However, in order to utilize the cocoon actuator, the pump size is adjusted to from about 15 mL to about 30 mL.

Pumps with a cocoon actuator in about 30 mL volume pump are subsequently tested. These pumps also utilize a piston made of low density polyethylene material (standard), while the pumps that are tested previously used high density polyethylene pistons. Initial tests are carried out with pumps with low density polyethylene pistons to check for performance of the pump with the cream.

14.) Filling #2274 (about 3.75%)—about 7.5 g Fill Weight.

Filling #2275 (about 3.75%)—about 15 g fill weight.

Albion 30 mL pump EV9/about 240 μl equipped with a cocoon actuator dosage about 240 μl with the piston made up of low density polyethylene are filled at about 7.5 g and about 15 g fill weights using Imiquimod cream about 3.75% w/w (Lot #GJJ068). The fill weights are determined to be about 10.5 grams with the restitution rate of about 7.5 g and about 18 g with the restitution rate of about 15 g as almost about 3 g of the cream is held back in the dosing chamber. All pumps have their piston moved to the position during the snapping of the actuator unit to avoid empty space on the top of the pump barrel.

Once again, Study #s 2274 and 2275 utilizing pumps with standard piston made of low density polyethylene material, where as all previous studies are conducted using pistons made up of high density polyethylene material.

All the physical test results are acceptable and loss prime at about 4 weeks testing is at about 95.8% and about 96.6% respectively thus possibly confirming the earlier theory that the failure for loss prime may be attributed to drying of the cream at nozzle tip once actuated. The use of the cocoon actuator or shutter surprisingly and unexpectedly, but successfully, corrected the loss of prime issue.

15.) Filling #2324 (about 3.75%)—about 7.5 g Fill Weight.

This study is initiated with Albion 30 mL Pump EV9/about 240 μl and cocoon actuator with piston made of high density polyethylene material (the pump body and the stem are made of polybutylene terephthalate, the actuator is made of polypropylene homopolymer/low density polyethylene and the piston is made of high density polyethylene material). The pump is filled with Imiquimod cream about 3.75% w/w (lot #GJJ068). Based on evaluating the restitution rate, it is estimated that approximately 3 g of the cream is left in the pump chamber. As a result, a fill weight of about 10.5 g is required to meet about 7.5 g Label claim.

The main goal of this study is to prove that the change of piston material from low density to high density polyethylene material does not affect the performance of the pump systems of the present invention.

EXAMPLE 3

Stress and Stability Testing Results

A. Stress Testing/Stability Results

Several observations are made during the stress testing of the about 2.5%, about 3.75% and about 5% w/w imiquimod creams filled in the above filling trials (#2022 to #2029).

The observations are as follows:

1. Delamination is observed of the Nova laminated pouch material when it is stored at accelerated conditions (i.e. ≥about 40° C.). This leads to discontinuing any further development work with this pump model.

2. Loss of prime in both Nova and Albion pump models is observed after one week of storage. This is surprisingly corrected by using the Albion pump with cocoon actuator.

B. Stability Testing Results

Several stability programs per ICH guidelines involving a series of pump options, components, fill weights and imiquimod creams are initiated.

Table 2 illustrates the stability studies and the corresponding creams that are used, fill run number, lot number of bulk cream that is used, fill weight, pump model and packaging description.

Described below is a summary of each of the stability studies that are conducted. The data collected for each stability study can be found in Attachments I-IV.

TABLE 2

Table 2. Imiquimod Cream Stability Studies

| Stability Study | Imiquimod (IMQ) Cream w/w | Fill Run # | Bulk Cream Lot # | Fill Weight | Pump Model | Package Description |
|---|---|---|---|---|---|---|
| GW 805-01 | 2.5% IMQ | 2022 | GJJ067 - 2.5% | 7.5 g | Albion EV09/150 - 1.5 mL | 7.5 g fill in 15 mL Albion pump with 150 µl actuator |
| GW 805-01 | 2.5% IMQ | 2023 | GJJ067 - 2.5% | 15 g | Albion EV09/150 - 15 mL | 15 g fill in 15 mL Albion pump with 150 µl actuator |
| GW 805-01 | 2.5% IMQ | 2024 | GJJ067 - 2.5% | 7.5 g | Nova Pump EV09/150 - 15 mL pouch | 7.5 g fill in 15 mL Nova pump with 15 mL Aluminum pouch |
| GW 805-01 | 2.5% IMQ | 2025 | GJJ067 - 2.5% | 15 G | Nova Pump EV09/150 - 30 mL | 15 g fill in 15 mL Nova pump with 30 mL Aluminum pouch |
| GW 805-01 | 3.75% IMQ | 2026 | GJJ068 - 3.75% | 7.5 g | Albion EV09/150 - 15 mL | 7.5 g fill in 15 mL Albion pump with 150 µl actuator |
| GW 805-01 | 3.75% IMQ | 2027 | GJJ068 - 3.75% | 15 g | Albion EV09/150 - 15 mL | 15 g fill in 15 mL Albion pump with 150 µl actuator |
| GW 805-01 | 3.75% IMQ | 2028 | GJJ068 - 3.75% | 7.5 g | Nova Pump EV09/150 - 15 mL pouch | 7.5 g fill in 15 mL Nova pump with 15 mL Aluminum pouch |
| GW 805-01 | 3.75% IMQ | 2029 | GJJ068 - 3.75% | 15 g | Nova Pump EV09/150 - 30 mL pouch | 15 g fill in 15 mL Nova pump with 30 mL Aluminum pouch |
| GW 906-01 | 5% Aldara | 2080 | GJF033 - 5% | 7.5 g | Albion EV09/150 - 15 mL | 7.5 g fill in 15 mL Albion pump with 150 µl actuator |
| GW 906-01 | 5% Aldara | 2081 | GJF033 - 5% | 15 g | Albion EV09/150 - 15 mL | 15 g fill in 15 mL Albion pump with 150 µl actuator |
| GW 906-01 | 5% Aldara | 2082 | GJF033 - 5% | 7.5 g | Nova Pump EV09/150 - 15 mL pouch | 7.5 g fill in 15 mL Nova pump with 15 mL Aluminum pouch |
| GW 906-01 | 5% Aldara | 2083 | GJF033 - 5% | 15 g | Nova Pump EV09/150 - 30 mL pouch | 15 g fill in 15 mL Albion pump with 30 mL Aluminum pouch |
| GW 805-01 | 2.5% IMQ | 2084 | GJJ067 - 2.5% | 15 g | Albion EV09/240 - 15 mL | 15 g fill in 15 mL Albion pump with 240 µl actuator |
| GW 907-01 | 3.75% IMQ | 2085 | GJJ068 - 3.75% | 15 g | Albion EV09/240 - 15 mL | 15 g fill in 15 mL Albion pump with 240 µl actuator |
| GW 907-01 | 5% Aldara | 2103 | GJF033 - 5% | 15 g | Albion EV09/240 - 15 mL | 15 g fill in 15 mL Albion pump with 240 µl actuator |

TABLE 2-continued

Table 2. Imiquimod Cream Stability Studies

| Stability Study | Imiquimod (IMQ) Cream w/w | Fill Run # | Bulk Cream Lot # | Fill Weight | Pump Model | Package Description |
|---|---|---|---|---|---|---|
| GW 907-01 | 3.75% IMQ | 2274 | GJJ068 - 3.75% | 7.5 g | Albion EV09/240 - 30 mL with cocoon | 15 g fill in 30 mL Albion pump with 240 µl cocoon actuator/PEBD piston |
| GW 921-01 | 3.75% IMQ | 2275 | GJJ068 - 3.75% | 15 g | Albion EV09/240 - 30 mL with cocoon | Albion EV09/240 - 30 mL with cocoon actuator/PEBD piston 15 g fill |
| GW 921-01 | 3.75% IMQ | 2324 | GJJ068 - 3.75% | 7.5 g | Albion EV09/240 - 30 mL with cocoon | Albion EV09/240 - 30 mL with cocoon actuator/PEHD piston 15 |

Figure 8:
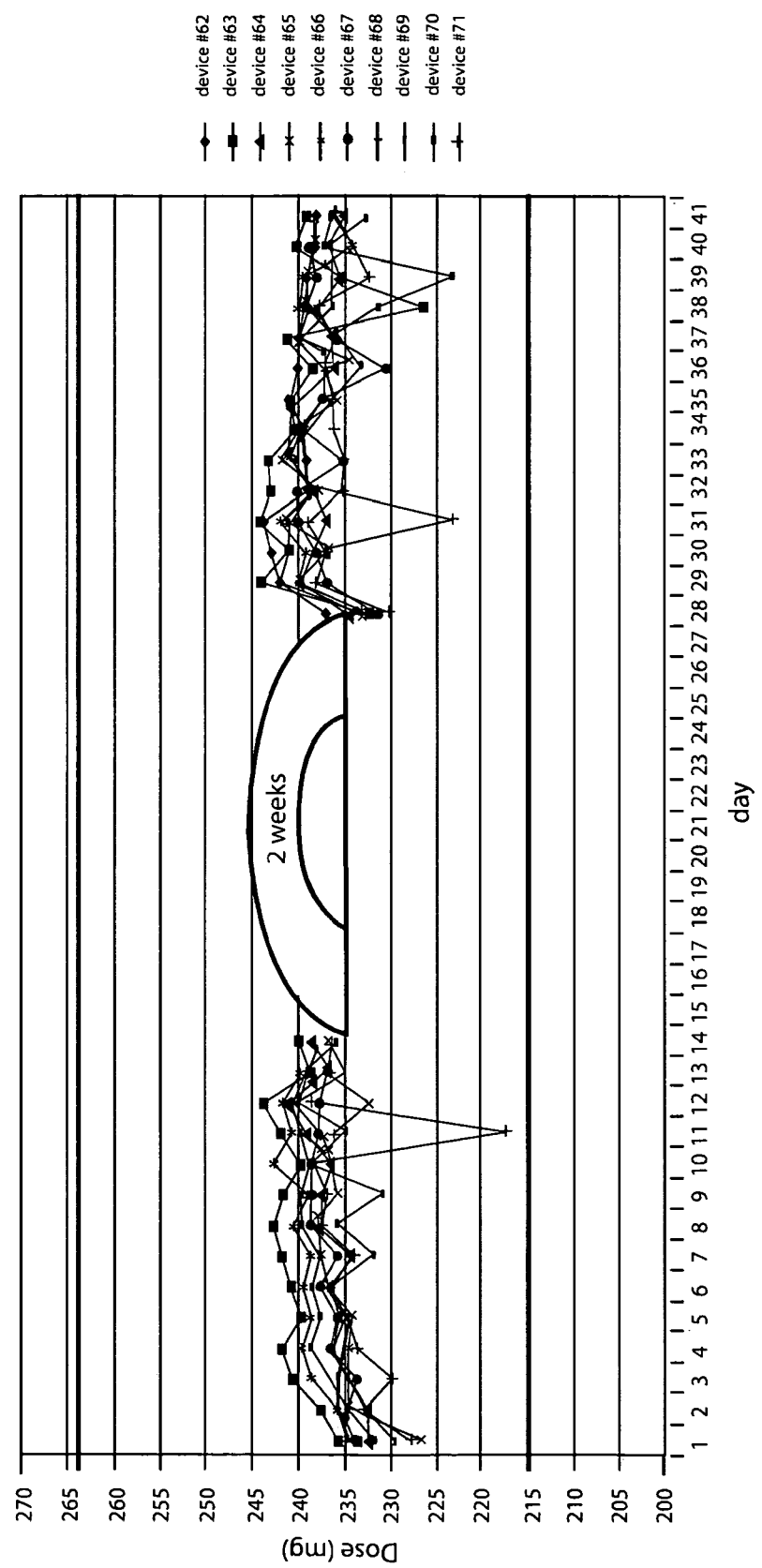
FIG. 8 shows a study regarding the evolution of daily dispensed doses from 10 packagings over a six week cycle using an Albion 30 piston LDPE restitution 7.5 ml+EV09/240+Cocoon pre-filled with an imiquimod 3.75% cream (conditions are under vacuum) to simulate a patient's clinical treatment period of 2×2×2. In this study, a pump is first primed and then actuated once every day for 2 weeks, then left static for 2 weeks, and then again actuated once daily for 2 more weeks to examine dose amount dispensed following each actuation. This study involves three two cycles (2×2×2) and shows that each dose dispensed per single daily actuation during the first two week cycle and again during the third two week cycle was about 240 mg of imiquimod 3.75% cream. See also Attachment VI below.
Figure 9:
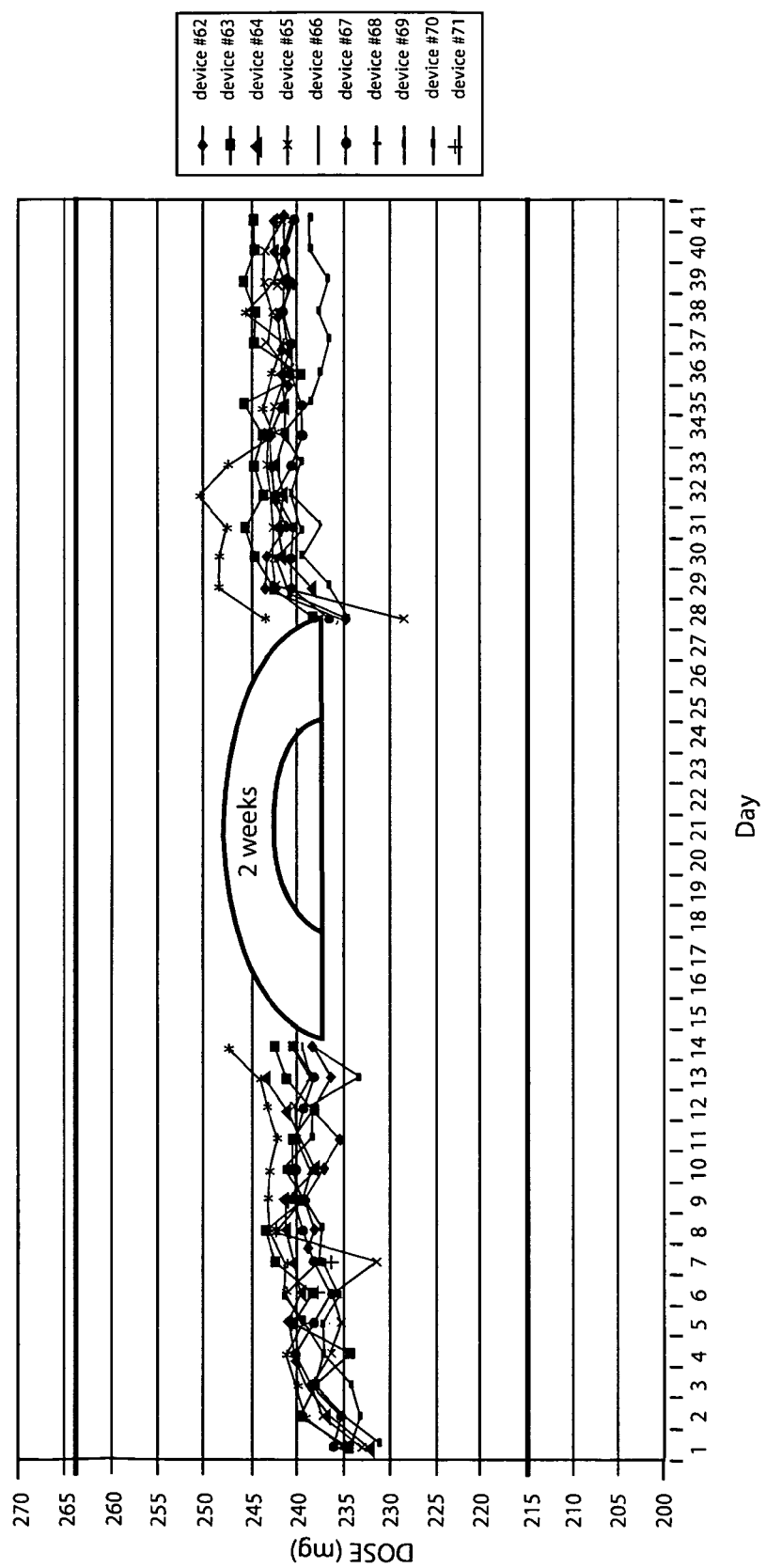
FIG. 9 shows a study regarding the evolution of daily dispensed doses from 10 packagings over a six week cycle using an Albion 30 piston LDPE restitution 15 ml+EV09/240+Cocoon pre-filled with an imiquimod 3.75% cream (conditions are under vacuum) to simulate a patient's clinical treatment period of 2×2×2. In this study, a pump is first primed and then actuated once every day for 2 weeks, then left static for 2 weeks, and then again actuated once daily for 2 more weeks to examine dose amount dispensed following each actuation. This study involves three two cycles (2×2×2) and shows that each dose dispensed per single daily actuation during the first two week cycle and again during the third two week cycle was about 240 mg of imiquimod 3.75% cream (see also Attachment VI below).

*The 2.5%, 3.75% and 5.0% imiquimod creams are isa cream formulation numbers 146, 202 and 16, respectively, and are the creams used in Examples 1-4, FIGS. 8 and 9 and Attachments I-XV, respectively.

1.) Stability Study GW 805-01-Summary.

Several observation/conclusions can be drawn from this study.

First, the delamination of the Nova pump pouch can be clearly viewed as early as about 2 months under accelerated conditions (about 40° C./75% RH).

All other testing (imiquimod assay, viscosity, benzyl alcohol, methyl and propyl parabens, pH, and 4 hydroxy imiquimod) remain well within specification and within the trend that is observed in the stability data for each cream in the commercial sachets presentation. The n-oxide testing is not performed initially as the method is not developed, however the method is available for testing the samples that are stored for about 9 month period at about 25 C160 RH and no detectable levels of n-oxide are observed.

This data can be seen in Attachment I.

2.) Stability Study GW 906-01-Summary.

This study is conducted to determine the compatibility/ stability of the Aldara® about 5% w/w (imiquimod) cream formulation in both about 7.5 g and about 15 g fill weight in Albion and Nova pump systems. The stability of the formulations in both the Albion over about nine months and Nova pumps over about a three month period are consistent and passes all specifications. However, a notable difference in lower viscosities of the formulations at about T=0 and at subsequent time points can be observed which is due to the age (6 months) of the bulk cream that is used for filling trials. Furthermore, the internal surfaces of the pouch for the Nova pumps that is stored at about 40° C./75% RH are observed to delaminate after about 2 months at both fill volumes (about 7.5 and about 15 g), and are subsequently discontinued from testing after the about 3 month time point.

The stability data up to and including about 9 months, indicates that the Albion pump at the fill volumes of about 7.5 and about 15 g with the Aldara® about 5% w/w formulation is suitable for commercial use.

Both fill volumes (about 7.5 and about 15 g) is stored in the Albion pumps at about 40° C. 175% RH for about 3 months passes the PET test for all organisms according to the European Pharmacopeia and for the organism E. coli, which is an additional requirement for the United States Pharmacopeia.

All other testing (imiquimod assay, viscosity, benzyl alcohol, methyl and propyl parabens, pH, and 4 hydroxy imiquimod) remain well within specification and within the trend that is observed in the stability data for Aldara® 5% w/w cream in the commercial sachets presentation.

The samples are also analyzed using the n-oxide method following about 9 months storage at about 25° C./60% RH and no detectable levels of n-oxide are observed.

This data is in Attachment II.

3.) Stability Study GW 907-01-Summary.

The stability of the formulations in the Albion pump over about six months for all three concentrations of imiquimod (about 2.5%, about 3.75% and about 5% w/w) meet all specifications (imiquimod assay, viscosity, benzyl alcohol, methyl and propyl parabens, pH, and 4 hydroxy imiquimod) and compare well with the equivalent formulations that are stored in borosilicate glass vials over the same period of time. The results also demonstrate the same trends that are observed in the stability data for each cream in the commercial sachet presentation. However, a notable difference between the results in this study and those that are observed in other 2.5%, 3.75% and 5% w/w imiquimod creams. In the commercial sachet presentation are the lower viscosities of the formulations at about T=0 and the subsequent time points. This is the direct result of the age of the bulk cream ($\approx$2 months) prior to filling.

The samples are also analyzed using the n-oxide method following 9 months storage at about 25° C./60% RH and no detectable levels of n-oxide are observed.

In addition, all the formulations that are stored in the Albion pumps at about 40° C./75 RH for about 3 months passes Preservative Efficacy Test (PET) for all organisms according to the European Pharmacopeia and for the organism E. coli which is an additional requirement for the United States Pharmacopeia. This data is in Attachment III.

4.) Stability Study GW 921-01-Summary.

The stability of Imiquimod cream about 3.75% in Albion 30 mL EV09/about 240 µl (the pump body and the stem are made of polybutylene terephthalate, the actuator is made of polypropylene homopolymer/low density polyethylene and the piston is made of high density polyethylene material). The pump is equipped with a cocoon actuator. The test results for samples that are stored for about 6 months at about 25° C./60% RH and about 40° C./75 RH meet all specifications (imiquimod assay, viscosity, benzyl alcohol, methyl and propyl parabens, pH, and 4 hydroxy imiquimod). In addition, the data compares well with the equivalent formulation that is stored in borosilicate glass vials over the same period of time and also within the trends that are observed in the stability data for each cream in the commercial sachet presentation. The data for top, middle and bottom samples that are taken for imiquimod, parabens indicate that the product is homogenous in the pump.

All samples are also analyzed using the n-oxide method following 6 months storage at about 25° C./60% RH and about 40° C./75 RH. There are no detectable levels of n-oxide observed. This data is in Attachment IV.

EXAMPLE 4

Additional Studies Conducted

A. USP Extractable Testing

The pump delivery system, Albion 30 mL EV09/about 240 µl is equipped with a cocoon actuator (pump body and the stem are made of polybutylene terephthalate, the actuator is made of polypropylene homopolymer/low density polyethylene and the piston is made of high density polyethylene material) that is selected for commercial use meets USP 32/NF 27 <661> Physicochemical Tests-Plastics, and USP <281> for Residue on Ignition.

This report is provided in Attachment V.

B. Patient in Use Test

In addition to the tests discussed in this report, Albion 30 mL, EV09/about 240 µl with cocoon actuator (the pump body and the stem are made of polybutylene terephthalate, the actuator is made of polypropylene homopolymer/low density polyethylene and the piston is made of high density polyethylene material) is tested to simulate the patient's clinical treatment period for 2 weeks on 2 weeks off and 2 weeks on. See FIGS. 8 and 9 and Attachment VI.

In this study, the pump is primed and actuated once every day for 2 weeks and then left static for 2 weeks. At the end of 2 weeks of no pump actuation, the pump is again actuated for 2 more weeks to check if a consistent and uniform dosage amount of cream is available to patient for the treatment period. The results are acceptable as the pump provides approximately 240 mg cream for each daily application during all 4 weeks of the treatment. See FIGS. 8 and 9. The data is provided in the Attachment VI.

C. Leak Test During Stability Study

During the course of the stability studies (about 12 month time point for GW 805, 906, 907 and 9 months for GW 921), it is decided to place all pumps on their sides to monitor leaking and delivery performance.

There is no leaking of the product from the pumps and all pumps delivery performance is acceptable.

Figure 10:
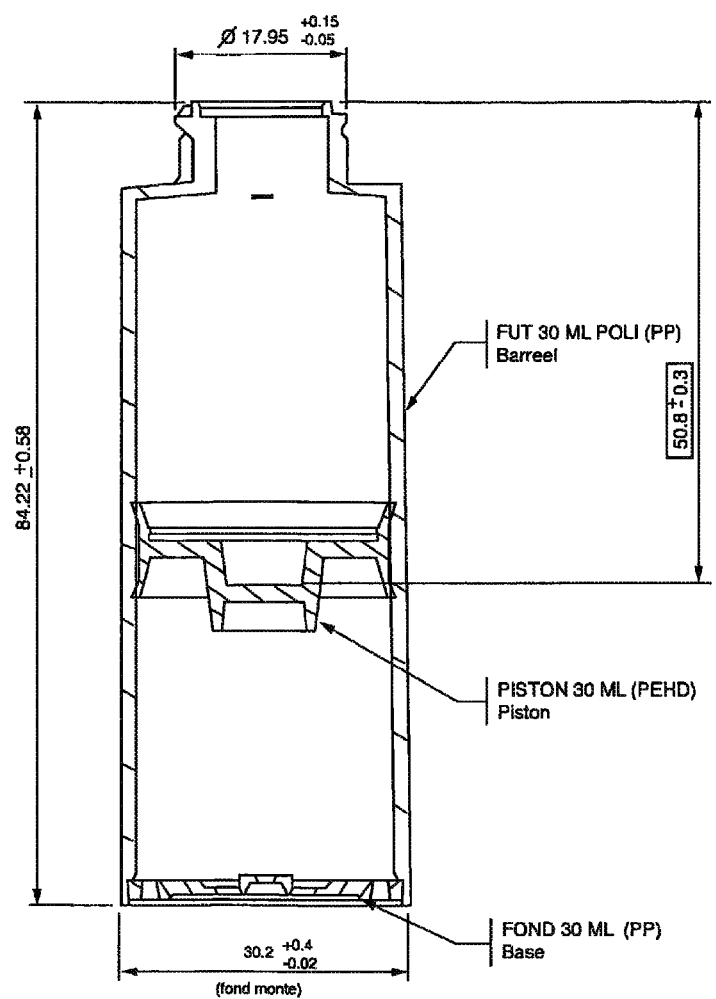
FIG. 10 is a cross-sectional view of a further embodiment of a lower or first subassembly used in the dispensing package of the present invention, which includes a hollow body along with the take-up piston and base closure member (see also Attachment VII below)
Figure 11:
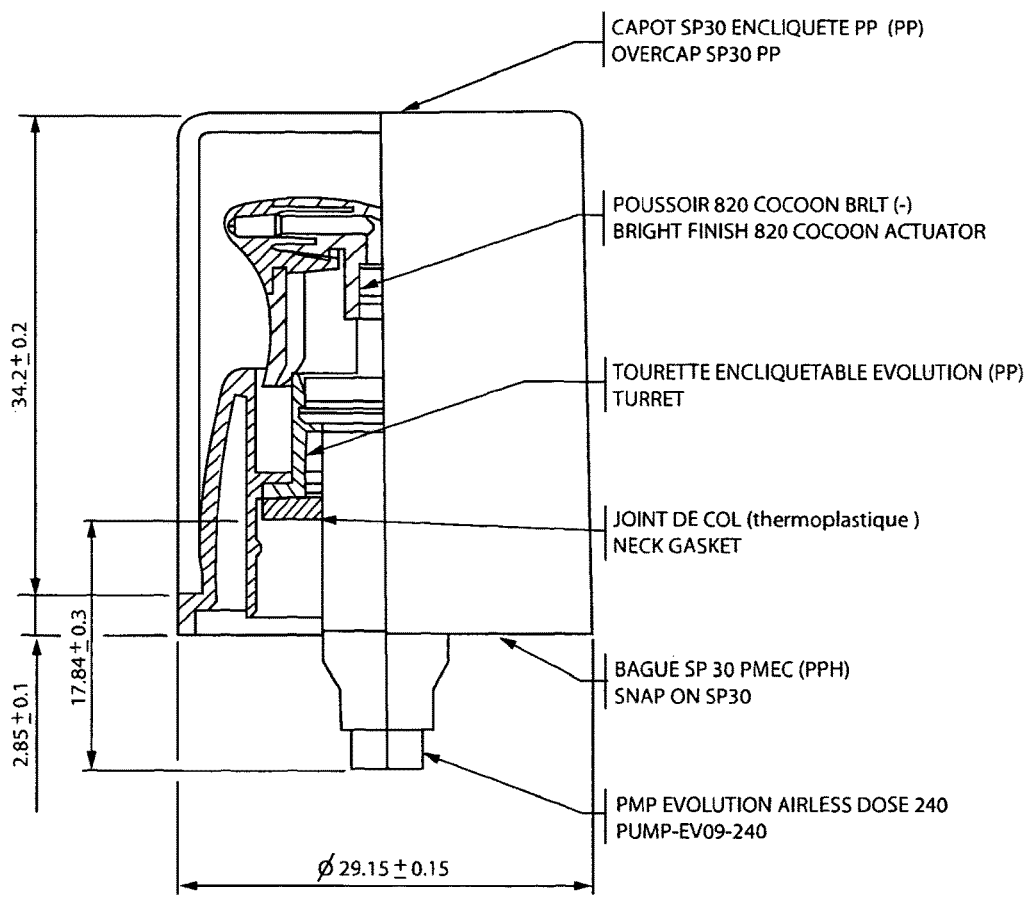
FIG. 11 is a partial cross-sectional view of a further embodiment of an upper or second subassembly used in the dispensing package of the present invention, which includes a dispensing head, a finger-operable pump, a holding member and a cap (no compressed neck gasket) (see also Attachment VII below).
Figure 12:
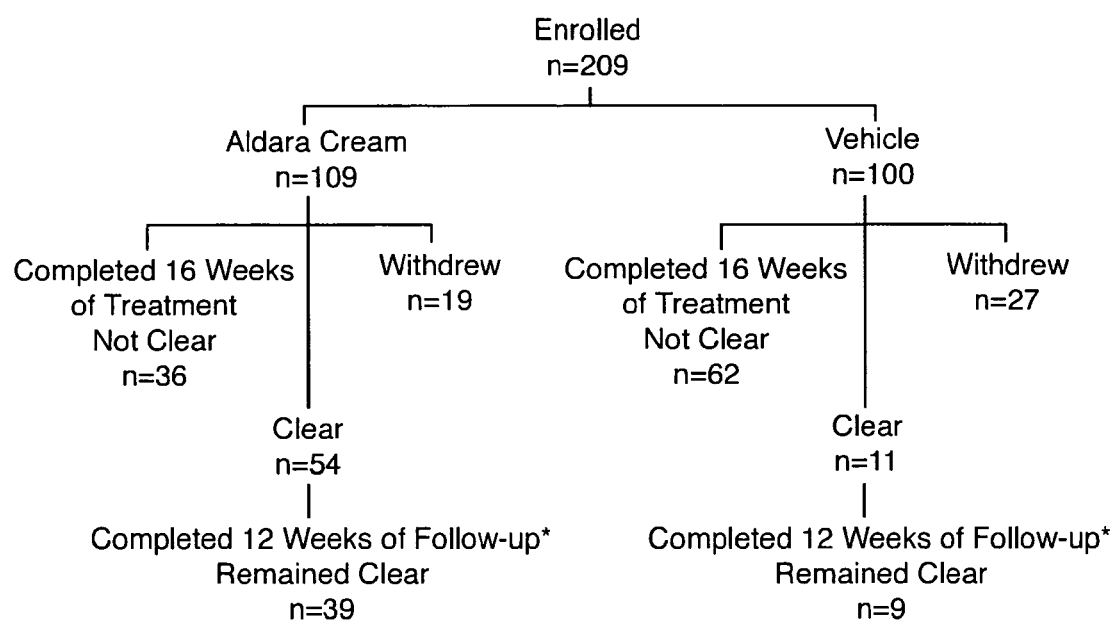
FIG. 12 is a graphic representation of subject accountability (external genital warts).
Figure 13:
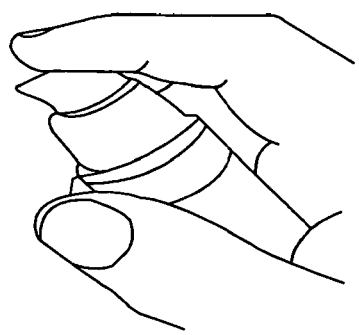
FIG. 13 is a perspective view of a proper methodology for utilizing the pump in accordance with the disclosure.

Based on the satisfactory physical, chemical and performance testing data, Albion 30 mL EV09/about 240 µl cocoon actuator (the pump body and the stem are made of polybutylene terephthalate, the actuator is made of polypropylene homopolymer/low density polyethylene and the piston is made of high density polyethylene material) is remarkable and surprisingly acceptable and, therefore, selected for commercialization. In addition, the NDA registration stability batches using this pump filled at both about 7.5 g and about 15 g fill using 3.75% and 5% w/w imiquimod cream are manufactured and are placed on stability at 3M, Loughborough, UK. This pump system is covered under Valois's DMF number 18156 "Albion 30 nil Piston Assembled Barrel+EV09/240 Pump+PR820 Cocoon Actuator+Cap". The pump parts, assembly and specifications are provided in Attachment VII. See also FIGS. 10 and 11.

EXAMPLE 5

Imiquimod Cream Formulation 5

A cream according to the present invention is prepared from the following ingredients in Table 3.

TABLE 3

Imiquimod Cream Formulation 5

| Oil Phase | Example 5 % by Weight | Example 5 Amount |
|---|---|---|
| 1-isobutyl-1H-imidazo[4,5-c]-quinolin-4-amine | 1.0 | 40.0 g |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase Glycerin | 2.0 | 80.0 g |
| Methylparaben | 0.2 | 8.0 g |
| Propylparaben | 0.02 | 0.8 g |
| Purified water | 76.48 | 3059.2 g |

The materials listed above were combined according to the following procedure.

The glycerin, methylparaben, propylparaben and water were weighed into a 4 liter glass beaker then heated on a hot plate with stirring until the parabens isostearic acid and 1-isobutyl-1H-imidazo[4,5-c]-quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°-75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

EXAMPLES 6-13

Imiquimod Cream Formulations 6-13

Using the general method of Example 5, the imiquimod cream formulations shown in Tables 4 and 5 are prepared.

TABLE 4

Imiquimod Cream Formulations 6-9

| | % by Weight | | | |
|---|---|---|---|---|
| | Example 6 | Example 7 | Example 8 | Example 9 |
| Oil Phase | | | | |
| 1-isobutyl-1H-imidazo[4,5-c]quinolin-4-amine | 1.0 | 1.0 | 1.0 | 1.0 |
| Isostearic acid | 10.0 | 10.0 | 5.0 | 5.0 |
| Benzyl alcohol | | 2.0 | | |
| Cetyl alcohol | | 1.7 | | |
| Stearyl alcohol | | 2.3 | | |

TABLE 4-continued

Imiquimod Cream Formulations 6-9

| | % by Weight | | | |
|---|---|---|---|---|
| | Example 6 | Example 7 | Example 8 | Example 9 |
| Cetearyl alcohol | 6.0 | | 6.0 | 6.0 |
| Polysorbate 60 | 2.55 | 2.55 | 2.55 | 2.55 |
| Sorbitan monostearate | 0.45 | 0.45 | 0.45 | 0.45 |
| Brij ™ 30[a] | | | | 10.0 |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 77.78 | 77.78 | 82.78 | 72.78 |

[a]Brij ™ 30 (polyoxyethylene(4) lauryl ether) is available from ICI Americas, Inc.

TABLE 5

Imiquimod Cream Formulations 10-13

| | % by Weight | | | |
|---|---|---|---|---|
| | Example 10 | Example 11 | Example 12 | Example 13 |
| Oil Phase | | | | |
| 1-isobutyl-1H-imidazo-[4,5-c]quinolin-4-amine | 1.0 | 1.0 | 1.0 | 1.0 |
| Isostearic acid | 10.0 | 25.0 | 10.0 | 6.0 |
| Benzyl alcohol | | 2.0 | | 2.0 |
| Cetyl alcohol | | 2.2 | 1.7 | |
| Stearyl alcohol | | 3.1 | 2.3 | |
| Cetearyl alcohol | 6.0 | | | 6.0 |
| Polysorbate 60 | 2.55 | 3.4 | 2.55 | 2.55 |
| Sorbitan monostearate | 0.45 | 0.6 | 0.45 | 0.45 |
| Brij ™ 30[a] | 10.0 | | | |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

[a]Brij ™ 30 (polyoxyethylene(4) lauryl ether) is available from ICI Americas, Inc.

EXAMPLE 14

Imiquimod Cream Formulation 14

A cream according to the present invention is prepared from the following ingredients in the following Table 6.

TABLE 6

Imiquimod Cream Formulation 14

| | % by Weight | Amount |
|---|---|---|
| Oil Phase | | |
| 1-isobutyl-1H-imidazo[4,5-c]quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |
| Aluminum stearate | 8.0 | 24.0 g |
| Cetyl alcohol | 4.0 | 12.0 g |
| Witconol ™ 14[a] | 3.0 | 9.00 g |
| Acetylated lanolin | 1.0 | 3.0 g |
| Propylparaben | 0.063 | 0.19 g |

TABLE 6-continued

Imiquimod Cream Formulation 14

| | % by Weight | Amount |
|---|---|---|
| Aqueous Phase | | |
| Veegum ™ K[b] | 1.0 | 3.0 g |
| Methylparaben | 0.12 | 0.36 g |
| Purified water | 49.017 | 147.05 g |

[a]Witconol ™ 14 (polyglyceryl4 oleate) is available from Witco Chemical Corp. Organics Division
[b]Veegum ™ K (colloidal magnesium aluminum silicate) is available from R. T. Vanderbilt Company Inc.

The materials listed above were combined according to the following procedure: The 1-isobutyl-1H-imidazo[4,5-c]quinolin-4-amine and the isostearic acid were weighed into a glass jar and heated with occasional stirring until the amine was dissolved (the temperature reached 68° C.). To this solution was added, the petrolatum, mineral oil, aluminum stearate, cetyl alcohol, Witconol™ 14, acetylated lanoline and propylparaben. The mixture was heated to 75° C. In a separate beaker, the methylparaben and water were combined and heated until the paraben dissolved (the temperature reached 61° C.). The Veegum™ K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

EXAMPLE 15

Imiquimod Ointment Formulation 15(a) and 15(b)

An ointment according to the present invention is prepared from the ingredients in the following Table 7.

TABLE 7

Imiquimod Ointment Formulation 15(a)

| | Example 15(a) % by Weight | Example 15(a) Amount |
|---|---|---|
| 1-isobutyl-1H-imidazo [4,5-c]quinolin-4-Amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| Witconol ™ | 143.0 | 0.60 g |
| Aluminum stearate | 8.0 | 1.60 g |

The materials listed above are combined according to the following procedure.

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

Using the general procedure of Example 15, an ointment containing the ingredients in the following Table 8 is prepared.

TABLE 8

Imiquimod Ointment Formulation 15(b)

| | Example 15(b) % by Weight | Example 15(b) Amount |
|---|---|---|
| 1-isobutyl-1H-imidazo[4,5-c]quinolin-4-Amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

EXAMPLES 16-18

Imiquimod Cream Formulations 16-18

Creams of the present invention are prepared using the ingredients shown in Table 9. The Example 1 except that benzyl alcohol was used with the isostearic acid to dissolve the 1-isobutyl-1H-imidazo[4,5-c]quinolin-4-amine.

TABLE 9

Imiquimod Cream Formulations 16-18

| | Example 16 Amount % by Weight | Example 17 Amount % by Weight | Example 18 Amount % by Weight |
|---|---|---|---|
| Oil Phase | | | |
| 1-isobutyl-1H-imidazo[4,5-c]quinolin-4-amine | 5.0 | 5.0 | 4.85 |
| Isostearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum | 3.0 | | 2.91 |
| Polysorbate 60 | 3.4 | 3.4 | 4.13 |
| Sorbitan monostearate | 0.6 | 0.6 | 0.73 |
| Stearic acid | | | 9.71 |
| Aqueous Phase | | | |
| Glycerin | 2.0 | 2.0 | 1.94 |
| Methylparaben | 0.2 | 0.2 | 0.19 |
| Propylparaben | 0.02 | 0.02 | 0.02 |

EXAMPLES 19 and 20

Imiquimod Cream Formulations 19 and 20

A cream according to the present invention is prepared from the ingredients in the following Table 10.

TABLE 10

Imiquimod Cream Formulations 19 and 20

| | Example 19 % by Weight | Example 20 % by Weight Amount |
|---|---|---|
| Oil Phase | | |
| 1-isobutyl-1H-imidazo[4,5-c]quinolin-4-Amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |
| Aqueous Phase | | |
| 1-isobutyl-1H-imidazo[4,5-c]quinolin-4-amine | 1.0 | 0.2 g |
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above are combined according to the following procedure: The isostearic acid and 0.8 g of 1-isobutyl-1H-imidazo[4,5-c]quinolin-4-amine or 1-(2-methylpropyl-1H-imidazo[4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

EXAMPLE 21

Imiquimod Cream Formulations 21-254

Topical Imiquimod Pharmaceutical Cream Formulations

TABLE 11

Lower Dosage Strength Imiquimod Cream Formulations 21-254

| Excipients | % w/w | % w/w | % w/w | % w/w | % w/w | % w/w |
|---|---|---|---|---|---|---|
| Formulation | 21 | 22 | 23 | 24 | 25 | 26 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.98 | 66.98 | 64.98 | 61.98 | 60.73 | 60.73 |
| Benzyl alcohol | 2.00 | 2.00 | 2.00 | 2.00 | 2.00 | 2.00 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Formulation | 27 | 28 | 29 | 30 | 31 | 32 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.98 | 60.98 | 60.98 | 57.08 | 58.98 | 55.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Formulation | 33 | 34 | 35 | 36 | 37 | 38 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.48 | 67.08 | 59.98 | 58.98 | 56.98 | 61.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Formulation | 39 | 40 | 41 | 42 | 43 | 44 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.73 | 66.73 | 64.73 | 61.73 | 60.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Formulation | 45 | 46 | 47 | 48 | 49 | 50 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.73 | 60.73 | 60.73 | 56.83 | 58.73 | 55.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |
| Formulation | 51 | 52 | 53 | 54 | 55 | 56 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.23 | 66.83 | 59.73 | 58.73 | 56.73 | 61.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |
| Formulation | 57 | 58 | 59 | 60 | 61 | 62 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.48 | 66.48 | 64.48 | 61.48 | 60.23 | 60.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |
| Formulation | 63 | 64 | 65 | 66 | 67 | 68 |
| Fatty acid | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.48 | 60.48 | 60.48 | 56.58 | 58.48 | 55.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |
| Formulation | 69 | 70 | 71 | 72 | 73 | 74 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.98 | 66.58 | 59.48 | 58.48 | 56.48 | 61.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Formulation | 75 | 76 | 77 | 78 | 79 | 80 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.23 | 66.23 | 64.23 | 61.23 | 59.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Formulation | 81 | 82 | 83 | 84 | 85 | 86 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.23 | 60.23 | 60.23 | 56.33 | 58.23 | 55.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Formulation | 87 | 88 | 89 | 90 | 91 | 92 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.73 | 66.33 | 59.23 | 58.23 | 56.23 | 61.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Formulation | 93 | 94 | 95 | 96 | 97 | 98 |
|---|---|---|---|---|---|---|
| Fatty acid* | 10.00 | 12.50 | 25.00 | 10.00 | 15.00 | 20.00 |
| Cetyl alcohol | 2.20 | 2.20 | 2.70 | 4.00 | 4.00 | 2.20 |
| Stearyl alcohol | 3.10 | 3.10 | 3.80 | 2.00 | 2.00 | 3.10 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.00 |
| Sorbitan Monostearate | 0.60 | 0.60 | 0.60 | 1.00 | 1.00 | 1.00 |
| Glycerin | 5.00 | 5.00 | 2.00 | 1.00 | 3.00 | 3.00 |
| Xanthan gum | 0.50 | 0.50 | 0.50 | 0.30 | 0.70 | 0.75 |
| Purified water | 65.98 | 63.48 | 54.78 | 70.28 | 64.28 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |
| Formulation | 99 | 100 | 101 | 102 | 103 | 104 |
| Fatty acid* | 10.00 | 12.50 | 25.00 | 10.00 | 15.00 | 25.00 |
| Cetyl alcohol | 2.20 | 2.20 | 2.70 | 4.00 | 4.00 | 2.70 |
| Stearyl alcohol | 3.10 | 3.10 | 3.80 | 2.00 | 2.00 | 3.80 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.40 |
| Sorbitan Monostearate | 0.60 | 0.60 | 0.60 | 1.00 | 1.00 | 0.60 |
| Glycerin | 5.00 | 5.00 | 2.00 | 1.00 | 3.00 | 2.00 |
| Xanthan gum | 0.50 | 0.50 | 0.50 | 0.30 | 0.70 | 0.50 |
| Purified water | 65.98 | 63.48 | 54.78 | 70.28 | 64.28 | 54.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |
| Formulation | 105 | 106 | 107 | 108 | 109 | 110 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.48 | 66.08 | 58.98 | 57.98 | 55.98 | 60.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |
| Formulation | 111 | 112 | 113 | 114 | 115 | 116 |
| Fatty acid* | 15.00 | 12.50 | 25.00 | 15.00 | 10.00 | 20.00 |
| Cetyl alcohol | 2.20 | 2.20 | 2.20 | 2.00 | 2.00 | 2.20 |
| Stearyl alcohol | 3.10 | 3.10 | 3.10 | 2.00 | 2.40 | 3.10 |
| White petrolatum | 6.00 | 5.00 | 3.00 | 3.40 | 2.80 | 3.00 |
| Polysorbate 60 | 3.00 | 3.00 | 3.40 | 3.80 | 3.80 | 3.00 |
| Sorbitan Monostearate | 1.00 | 1.00 | 0.60 | 0.20 | 1.00 | 1.00 |
| Glycerin | 5.00 | 5.00 | 2.00 | 3.00 | 3.00 | 3.00 |
| Xanthan gum | 1.00 | 0.50 | 1.00 | 0.30 | 0.30 | 0.75 |
| Purified water | 60.23 | 63.23 | 55.23 | 66.83 | 70.23 | 59.48 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |
| Formulation | 117 | 118 | 119 | 120 | 121 | 122 |
| Fatty acid* | 15.00 | 12.50 | 25.00 | 15.00 | 10.00 | 25.00 |
| Cetyl alcohol | 2.20 | 2.20 | 2.20 | 2.00 | 2.00 | 2.70 |
| Stearyl alcohol | 3.10 | 3.10 | 3.10 | 2.00 | 2.40 | 3.80 |
| White petrolatum | 6.00 | 5.00 | 3.00 | 3.40 | 2.80 | 3.00 |
| Polysorbate 60 | 3.00 | 3.00 | 3.40 | 3.80 | 3.80 | 3.40 |
| Sorbitan Monostearate | 1.00 | 1.00 | 0.60 | 0.20 | 1.00 | 0.60 |
| Glycerin | 5.00 | 5.00 | 2.00 | 3.00 | 3.00 | 2.00 |
| Xanthan gum | 1.00 | 0.50 | 1.00 | 0.30 | 0.30 | 0.50 |
| Purified water | 60.23 | 63.23 | 55.23 | 66.83 | 70.23 | 54.53 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |
| Formulation | 123 | 124 | 125 | 126 | 127 | 128 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.23 | 65.83 | 58.73 | 57.73 | 55.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |
| Formulation | 129 | 130 | 131 | 132 | 133 | 134 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 2.50 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.98 | 65.48 | 63.48 | 60.48 | 59.23 | 59.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |
| Formulation | 135 | 136 | 137 | 138 | 139 | 140 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 65.48 | 59.48 | 59.48 | 55.58 | 57.48 | 54.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |
| Formulation | 141 | 142 | 143 | 144 | 145 | 146 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.98 | 65.58 | 58.48 | 57.48 | 55.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |
| Formulation | 147 | 148 | 149 | 150 | 151 | 152 |
| Fatty acid* | 15.00 | 18.00 | 15.00 | 20.00 | 12.50 | 20.00 |
| Cetyl alcohol | 2.00 | 2.00 | 2.00 | 2.00 | 2.20 | 2.20 |
| Stearyl alcohol | 2.00 | 2.00 | 2.40 | 2.40 | 3.10 | 3.10 |
| White petrolatum | 3.40 | 2.80 | 3.40 | 2.80 | 5.00 | 3.00 |
| Polysorbate 60 | 3.00 | 3.80 | 3.00 | 3.00 | 3.40 | 3.00 |
| Sorbitan Monostearate | 1.00 | 1.00 | 0.20 | 0.20 | 0.60 | 1.00 |
| Glycerin | 3.00 | 2.00 | 1.00 | 3.00 | 6.00 | 3.00 |
| Xanthan gum | 0.30 | 0.70 | 0.70 | 0.30 | 0.50 | 0.75 |
| Purified water | 65.08 | 62.48 | 67.08 | 61.08 | 61.48 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |
| Formulation | 153 | 154 | 155 | 156 | 157 | 158 |
| Fatty acid* | 15.00 | 18.00 | 15.00 | 20.00 | 12.50 | 25.00 |
| Cetyl alcohol | 2.00 | 2.00 | 2.00 | 2.00 | 2.20 | 2.70 |
| Stearyl alcohol | 2.00 | 2.00 | 2.40 | 2.40 | 3.10 | 3.80 |
| White petrolatum | 3.40 | 2.80 | 3.40 | 2.80 | 5.00 | 3.00 |
| Polysorbate 60 | 3.00 | 3.80 | 3.00 | 3.00 | 3.40 | 3.40 |
| Sorbitan Monostearate | 1.00 | 1.00 | 0.20 | 0.20 | 0.60 | 0.60 |
| Glycerin | 3.00 | 2.00 | 1.00 | 3.00 | 6.00 | 2.00 |
| Xanthan gum | 0.30 | 0.70 | 0.70 | 0.30 | 0.50 | 0.50 |
| Purified water | 65.08 | 62.48 | 67.08 | 61.08 | 61.48 | 53.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |
| Formulation | 159 | 160 | 161 | 162 | 163 | 164 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.48 | 65.08 | 57.98 | 56.98 | 54.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |
| Formulation | 165 | 166 | 167 | 168 | 169 | 170 |
| Fatty acid* | 15.00 | 20.00 | 15.00 | 20.00 | 10.00 | 20.00 |
| Cetyl alcohol | 2.00 | 2.00 | 4.00 | 4.00 | 2.20 | 2.20 |
| Stearyl alcohol | 2.00 | 2.40 | 2.40 | 2.40 | 3.10 | 3.10 |
| White petrolatum | 3.40 | 2.80 | 2.50 | 3.40 | 5.00 | 3.00 |
| Polysorbate 60 | 3.00 | 3.00 | 3.00 | 3.80 | 3.40 | 3.00 |
| Sorbitan Monostearate | 1.00 | 0.20 | 1.00 | 1.00 | 0.60 | 1.00 |
| Glycerin | 3.00 | 3.00 | 1.00 | 3.00 | 5.00 | 3.00 |
| Xanthan gum | 0.30 | 0.30 | 0.30 | 0.70 | 0.50 | 0.75 |
| Purified water | 64.83 | 60.83 | 65.33 | 57.23 | 64.73 | 58.48 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Formulation | 171 | 172 | 173 | 174 | 175 | 176 |
|---|---|---|---|---|---|---|
| Fatty acid* | 15.00 | 20.00 | 15.00 | 20.00 | 10.00 | 25.00 |
| Cetyl alcohol | 2.00 | 2.00 | 4.00 | 4.00 | 2.20 | 2.70 |
| Stearyl alcohol | 2.00 | 2.40 | 2.40 | 2.40 | 3.10 | 3.80 |
| White petrolatum | 3.40 | 2.80 | 2.50 | 3.40 | 5.00 | 3.00 |
| Polysorbate 60 | 3.00 | 3.00 | 3.00 | 3.80 | 3.40 | 3.40 |
| Sorbitan Monostearate | 1.00 | 0.20 | 1.00 | 1.00 | 0.60 | 0.60 |
| Glycerin | 3.00 | 3.00 | 1.00 | 3.00 | 5.00 | 2.00 |
| Xanthan gum | 0.30 | 0.30 | 0.30 | 0.70 | 0.50 | 0.50 |
| Purified water | 64.83 | 60.83 | 65.33 | 57.23 | 64.73 | 53.53 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Formulation | 177 | 178 | 179 | 180 | 181 | 182 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.23 | 64.83 | 59.98 | 56.73 | 54.73 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Formulation | 183 | 184 | 185 | 186 | 187 | 188 |
|---|---|---|---|---|---|---|
| Fatty acid* | 15.00 | 10.00 | 12.50 | 19.00 | 20.00 | 20.00 |
| Cetyl alcohol | 2.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.00 |
| Sorbitan Monostearate | 0.20 | 0.60 | 0.60 | 0.60 | 0.60 | 1.00 |
| Glycerin | 1.00 | 4.00 | 5.00 | 2.00 | 6.00 | 3.00 |
| Xanthan gum | 0.70 | 0.50 | 0.50 | 0.50 | 0.50 | 0.75 |
| Purified water | 66.58 | 65.48 | 61.38 | 60.48 | 56.48 | 58.23 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Formulation | 189 | 190 | 191 | 192 | 193 | 194 |
|---|---|---|---|---|---|---|
| Fatty acid* | 15.00 | 10.00 | 12.50 | 19.00 | 20.00 | 25.00 |
| Cetyl alcohol | 2.00 | 2.20 | 2.20 | 2.20 | 2.20 | 2.70 |
| Stearyl alcohol | 2.40 | 3.10 | 3.10 | 3.10 | 3.10 | 3.80 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.40 |
| Sorbitan Monostearate | 0.20 | 0.60 | 0.60 | 0.60 | 0.60 | 0.60 |
| Glycerin | 1.00 | 4.00 | 5.00 | 2.00 | 6.00 | 2.00 |
| Xanthan gum | 0.70 | 0.50 | 0.50 | 0.50 | 0.50 | 0.50 |
| Purified water | 66.58 | 65.48 | 61.38 | 60.48 | 56.48 | 53.28 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Formulation | 195 | 196 | 197 | 198 | 199 | 200 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.98 | 64.58 | 57.48 | 56.48 | 54.48 | 59.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Formulation | 201 | 202 | 203 | 204 | 205 | 206 |
|---|---|---|---|---|---|---|
| Fatty acid* | 20.00 | 20.00 | 25.00 | 18.75 | 20.00 | 21.25 |
| Cetyl alcohol | 4.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 2.80 | 3.00 | 3.00 | 5.00 | 5.00 | 3.75 |
| Polysorbate 60 | 3.00 | 3.40 | 3.40 | 3.00 | 3.40 | 3.40 |
| Sorbitan Monostearate | 1.00 | 0.60 | 0.60 | 1.00 | 0.60 | 0.60 |
| Glycerin | 1.00 | 2.00 | 2.00 | 5.00 | 5.00 | 5.00 |
| Xanthan gum | 0.30 | 0.50 | 0.50 | 0.50 | 0.50 | 0.50 |
| Purified water | 64.53 | 59.23 | 54.23 | 55.48 | 54.23 | 54.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Formulation | 207 | 208 | 209 | 210 | 211 | 212 |
|---|---|---|---|---|---|---|
| Fatty acid* | 20.00 | 20.00 | 20.00 | 25.00 | 18.75 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 59.23 | 53.23 | 53.23 | 54.33 | 55.48 | 53.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Formulation | 213 | 214 | 215 | 216 | 217 | 218 |
|---|---|---|---|---|---|---|
| Fatty acid* | 25.00 | 20.00 | 20.00 | 20.00 | 20.00 | 21.00 |
| Cetyl alcohol | 2.20 | 4.00 | 2.20 | 2.20 | 2.20 | 2.20 |
| Stearyl alcohol | 3.10 | 2.40 | 3.10 | 3.10 | 3.10 | 3.10 |
| White petrolatum | 3.00 | 3.40 | 5.00 | 3.00 | 5.00 | 5.00 |
| Polysorbate 60 | 3.40 | 3.80 | 3.40 | 3.40 | 3.40 | 3.40 |
| Sorbitan Monostearate | 0.60 | 1.00 | 0.60 | 0.60 | 0.60 | 0.60 |
| Glycerin | 2.00 | 3.00 | 2.00 | 5.00 | 5.00 | 5.00 |
| Xanthan gum | 1.00 | 0.70 | 0.50 | 0.50 | 0.50 | 0.50 |
| Purified water | 53.73 | 55.73 | 57.23 | 56.23 | 54.23 | 53.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |
| Formulation | 219 | 220 | 221 | 222 | 223 | 224 |
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |
| Formulation | 225 | 226 | 227 | 228 | 229 | 230 |
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |
| Formulation | 231 | 232 | 233 | 234 | 235 | 236 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.48 | 64.08 | 56.98 | 55.98 | 53.98 | 58.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |
| Formulation | 237 | 238 | 239 | 240 | 241 | 242 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.73 | 63.73 | 61.73 | 58.73 | 57.48 | 57.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |
| Formulation | 243 | 244 | 245 | 246 | 247 | 248 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 63.73 | 57.73 | 57.73 | 53.83 | 55.73 | 52.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |
| Formulation | 249 | 250 | 251 | 252 | 253 | 254 |
| Fatty acid* | 25.00 | 15.00 | 20.00 | 20.00 | 20.0 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.20 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.23 | 63.83 | 56.73 | 55.73 | 53.73 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

*The Fatty acid referenced in this Table 11 can be, for example, linoleic acid (la), stearic acid (sa), palmitic acid (pa), isostearic acid (isa), unrefined oleic acid, (uoa), refined oleic acid, such as super refined oleic acid (roa), or mixtures thereof.

The materials listed below in this Example 21 are combined according to the following procedure to make cream formulations in the above Table 11 of this Example 21.

The work area, all vessels and equipment is initially cleaned prior to commencing manufacture. A 2 L glass container and paddle stirrer blade are placed onto a balance and the weight is recorded. The paddle is then removed from the vessel. The isostearic acid and benzyl alcohol are weighed directly into the 2 L glass container. The imiquimod is then weighed into the 2 L glass container and a spatula is used to ensure the imiquimod is wetted with the isostearic acid and benzyl alcohol mixture. The 2 L container is then heated in a water bath to about 55±5° C. while stirring with a Heidolph mixer (Note: aluminum foil is placed around the top of the vessel and the paddle for the mixer, to limit evaporation). The solution is visually inspected to confirm the imiquimod has fully dissolved prior to mixing with cetyl alcohol, stearyl alcohol, white petrolatum, polysorbate 60 and sorbitan monostearate.

Cetyl alcohol, stearyl alcohol, white petrolatum, polysorbate 60 and sorbitan monostearate are then weighed directly into the 2 L container and mixing is continued at about 55±5° C. until the oil phase is completely in solution. Separately, about 2 L of water are placed into a beaker and heated to 55±5° C. while stirring with a magnetic follower.

Briefly, about 500 ml of the heated water is transferred into a 1 L beaker and placed into the water bath maintained at about 55±5° C.

Half of the amount of glycerin required for the final formulation is then weighed into the beaker along with the total amount of methylparaben and propylparaben to the water (where both methyl and propyl paraben are weighed into weighing boats first, a pipette is used to remove a portion of the heated water to wash out the weighing boats to ensure total transfer of both the propyl- and methylparaben into the aqueous phase). The mixture is continuously stirred at about 55±5° C. (this is the aqueous phase).

The remaining glycerin is then added to a 28 ml vial and the xanthan gum is added and mixed using a small overhead mixer (1KA®-Werke Lab Egg) with paddle attachment for about 10 min.

The glycerin and xanthan mixture are then added slowly into the vortex of the aqueous phase, and a further aliquot of about 20 ml of heated water is used to rinse the vessel out into the water phase to ensure complete transfer.

The water phase is then heated and mixed at about 55±5° C. until the xanthan gum mixture is fully and evenly dispersed into the aqueous phase. The temperatures of both the water phase and oil phase are both maintained at about 55±5° C.

The aqueous phase is then transferred into the oil phase and the speed of the Heidolph mixer is increased during addition. The mixture is then homogenized on high speed for about 3 min and transferred immediately back to the Heidolph mixture; however, the contents of the homogenized sample, about 2 L, are mixed at about room temperature and allowed to cool to about 35° C.

The container and contents and the paddle from the overhead mixer are then re-weighed and the weight of the paddle and 2 L beaker, as determined above, are subtracted to determine the total weight of the formulation remaining.

The total weight (about 1 kg) of the cream is then made up to weight with heated water (Note: water evaporated during heating, which needs to be corrected at this point). The mixture is then transferred back onto the Heidolph mixer at about room temperature and mixed until the temperature of the formulation is below about 28° C. The lid of the container is then placed onto the vessel and stored at room temperature.

While the procedure above describes making an imiquimod cream using isostearic acid as the fatty acid, it is believed that this procedure may be applicable for preparing imiquimod creams based upon other fatty acids, such as those described in Table 11 above.

The lower dosage strength formulations of this Example 21 are believed to be stable and consistent with the specifications for the commercially available Aldara® (imiquimod) 5% cream. More preferably, low dosage formulations of this Example 21, especially as to those lower dosage strength formulations wherein the vehicle comprises an isostearic acid as the fatty acid, are believed to have the following:

(1) Stability. The imiquimod formulations of the present invention, when they are measured on HPLC at 25° C./60% RH, 30° C./65% RH and 40° C./75% RH over, one, two, three and six months, demonstrate stability consistent with the Aldara® 5% imiquimod cream;

(2) Degradation Products. No degradation products are detected in the formulations of the present invention, at its current recommended storage temperatures of about 4-25° C. In addition, there are no degradation products detected at any of the temperatures or time points mentioned under "Stability" above, when analyzed at about 318 nm.

(3) Homogeneity. The amount of imiquimod that is recovered from the formulations at any of the above-mentioned temperatures and time points is between about 90 to about 110% w/w thereby demonstrating good homogeneity;

(4) Benzyl Alcohol Content. The formulations of the present invention are also within specifications for the Aldara® (imiquimod) 5% cream, i.e., between 1.0% w/w and 2.1% w/w, at any of the above-mentioned temperatures and time points as to benzyl alcohol content.

(5) Microscopic Stability. There is no change in the particle size and no crystals are detected in the formulations of the present invention when they are stored at 25° C./60% RH and analyzed over a six month period;

(6) Macroscopic Stability. There are no obvious physical changes in the formulations of the present invention when they are stored at 25° C./60% RH and analyzed over a six month period;

(7) Viscosity. The formulations of the present invention are within the range of the specifications for the Aldara® (imiquimod) 5% cream, i.e., between 2000 cPs and 35,000 cPs, when they are stored at 25° C./60% RH and analyzed over a six month period; pH Stability. The formulations of the present invention are within the range of the specifications for the Aldara® (imiquimod) 5% cream, i.e., between pH 4.0 and pH 5.5) when they are stored at 25° C./600% RH and analyzed over a six month period;

(8) Preservative Efficacy Test ("PET"). The formulations of the present invention demonstrate sufficient reductions in colony forming unit counts for each of the organisms with which the formulations are inoculated, i.e., S. aureus, E. coli, Ps. Aeruginosa, C. albicans, and A. niger, at 2-8° C. and 40° C. over a 28 day test period and meet the requirements specified in both the USP and EP;

(9) Imiquimod In vitro Release. The Aldara® (imiquimod) 5% cream releases statistically significant ($p<0.05$) higher amounts of imiquimod over a 3 hour time period in comparison to the lower dosage strength formulations of the present invention through a synthetic membrane, e.g., Microporous polyethylene film 3M No. 9711 CoTran™. There is no statistical difference ($p<0.05$) in the total cumulative amount of imiquimod that is released from any of the 3.75% w/w imiquimod formulations. There is no statistical difference ($p<0.05$) in the total cumulative amount of imiquimod that is released from any of the 2.5% w/w imiquimod formulations. The Aldara® (imiquimod) 5% cream also statistically significantly ($p<0.05$) releases imiquimod at a faster rate over a 3 hour time period in comparison to the lower dosage strength formulations of the present invention through a synthetic membrane, e.g., Microporous polyethylene film 3M No. 9711 CoTran™. There is no statistical difference ($p<0.05$) between the imiquimod release rates for any of the 3.75% w/w imiquimod formulations. There is no statistical difference ($p<0.05$) between the imiquimod release rates for any of the 2.5% w/w imiquimod formulations. Thus, the greater the amount of imiquimod in a formulation, the faster and greater the total amount of imiquimod that is released from such formulation that the amount and rate of release of imiquimod are concentration dependant and that the rates and amounts of release of imiquimod from the formulations of the present invention are linear and dose proportionate to the Aldara® 5% imiquimod cream;

(10) Imiquimod In vitro Skin Permeation (Franz Cell Study). With respect to statistical analyses, there is no statistical difference between the lower dosage strength formulations of the present invention and the Aldara® (imiquimod) 5% cream as to the amount of imiquimod recovered from the receiver fluid, epidermis and dermis combined. Nonetheless, there is a statistically significant ($p<0.05$) dose proportionate difference between the amount of imiquimod recovered from each of the matrices with respect to the concentration of imiquimod in the lower dosage strength formulations of the present invention and the Aldara® (imiquimod) 5% cream for both un-absorbed and stratum corneum. Thus there is a linear dose release between the amount of imiquimod that is applied and recovered in each of the matrices, i.e., receiver fluid, unabsorbed dose, stratum corneum, epidermis and dermis.

ANOVA statistical analysis at 95% confidence level is used to analyze the stability data generated, including the data generated for the membrane and skin permeation experiments.

It is also believed that the formulations of the present invention, including the formulations identified in this Example 21, have Hydrophilic-lipophilic balance (HLB) values between about 12 and 15, and more preferably between about 12.4 and about 13.4.

The complete disclosures of the patents, patent documents, labels and publications cited herein, including U.S. Pat. No. 6,991,139 and Attachments I-XV, are incorporated herein by reference in their entireties as if each were individually reproduced and incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

The invention claimed is:

1. A system for treating a subject diagnosed with a dermal and/or mucosal-associated condition, said system comprising:
   a dispensing device that includes:
      a lower subassembly that has a tubular body portion that defines an elongated interior fluid storage chamber into which a take-up piston element is slidably disposed; and
      an upper subassembly mounted upon the lower subassembly and including a dispensing head and an airless pumping mechanism, the dispensing head having an internal fluid passage formed therein which terminates in a self-closing outlet, the dispensing head also including and a finger-operated actuator which is operatively associated with the airless pumping mechanism; and
   an imiquimod cream formulation disposed at least partially within the fluid storage chamber defined in the tubular body portion of the lower subassembly of the dispensing package, and wherein operation of the finger-operated actuator causes the airless pumping mechanism to withdraw a portion of the imiquimod cream formulation from within the interior chamber and to dispense the imiquimod cream formulation into the internal fluid passage formed in the dispensing head wherein the pressure of dispensed cream causes the self-closing outlet to open thereby discharging a predefined effective unit dose amount of imiquimod cream from the dispensing package.

2. The system of claim 1, wherein the imiquimod cream formulation contains imiquimod in an amount by weight of between 1% and 10% w/w.

3. The system of claim 1, wherein the imiquimod cream formulation contains imiquimod in an amount by weight of between 1% and 5% w/w.

4. The system of claim 1, wherein the imiquimod cream formulation contains imiquimod in an amount by weight selected from a group consisting of 2.5%, 3.75% and 5% w/w.

5. The system of claim 1, wherein the fluid storage chamber is adapted and configured for storing about 7.5 grams of imiquimod cream formulation.

6. The system of claim 1, wherein the take-up piston is disposed within the tubular body portion so as to partially define the fluid storage chamber, wherein the take-up position moves axially towards the pumping device when the pumping device is manually operated, so as to reduce the volume of the fluid storage chamber by an amount which is equivalent to the volume of imiquimod cream formulation dispensed from the dispensing package.

7. The system of claim 1, wherein upon each operation of the pumping device an amount of the imiquimod cream formulation which is within about 15% of the predefined unit dose amount is discharged from the dispensing device.

8. The system of claim 1, wherein after multiple operations of the pumping device, the overall average of the dose value is within about 10% of the predefined unit dose amount.

9. The system of claim 1, wherein the predefined unit dose amount is about 240 mg.

10. The system of claim 1, wherein no more than 5 manual actuations of the pumping mechanism are required in order to prime the pumping mechanism, and start observing the discharging of imiquimod cream formulation from the self-closing discharge orifice.

11. The system of claim 1, wherein about 85% of the imiquimod cream formulation contained within the internal fluid passage of the dispensing head following an application remains in the internal fluid passage during storage.

12. The system of claim 1, wherein the dermal and/or mucosal-associated condition comprises any of: external genital warts, perianal warts, actinic keratosis, and superficial basal cell carcinoma.

13. The system of claim 1, wherein the dispensing package is configured so that a single actuation dispenses the predefined unit dose amount.

14. The system of claim 1, further comprising:
   a cap for sealing the self-closing outlet.

15. An airless pump pre-filled with an imiquimod cream for treating a subject diagnosed with a dermal and/or mucosal-associated condition with predefined single unit-dose amounts of the imiquimod cream dispensed from the pump, said airless pump comprising:
   a dispensing device that includes:
      a lower subassembly that has a tubular body portion that defines an elongated interior fluid storage chamber into which a take-up piston element is slidably disposed; and
      an upper subassembly mounted upon the lower subassembly and including a dispensing head and an airless pumping mechanism, the dispensing head having an internal fluid passage formed therein which terminates in a self-closing outlet, the dispensing head also including and a finger-operated actuator which is operatively associated with the airless pumping mechanism; and
   between about 5 grams and about 30 grams of the imiquimod cream disposed at least partially within the fluid storage chamber defined in the tubular body portion of the lower subassembly of the dispensing package,
   wherein operation of the finger-operated actuator causes the airless pumping mechanism to withdraw a portion of the imiquimod cream from within the interior chamber and to dispense the imiquimod cream formulation into the internal fluid passage formed in the dispensing head,
   wherein the pressure of the dispensed imiquimod cream causes the self-closing outlet to open thereby discharging the predefined single unit-dose amount of the imiquimod cream from the dispensing package,
   wherein the take-up piston is disposed within the tubular body portion so as to partially define the fluid storage chamber, wherein the take-up position moves axially towards the pumping mechanism when the pumping mechanism is manually operated, so as to reduce the volume of the fluid storage chamber by an amount which is equivalent to the volume occupied by the predefined single effective unit-dose amount of the imiquimod cream dispensed from the dispensing package.

16. The airless pump of claim 15, wherein the predefined single unit-dose amount is about 240 mg and the imiquimod cream comprises any of a 2.5% imiquimod cream, a 3.75% imiquimod cream, a 5% imiquimod cream.

17. The airless pump of claim 15, wherein the pump is configured to dispense at least about 85% of the single unit dose amount during each said pumping step during treatment.

18. The airless pump of claim 15, wherein the dispensing device is adapted to dispense a single product stored therein, the single product comprising the imiquimod formulation.

19. The airless pump of claim 15, wherein the dispensing device is adapted to protect a remaining imiquimod formulation remaining within the dispensing device after each actuation from air contact, oxidation, degradation and contamination such that subsequent actuations of the dispensing device each dispense a subsequent effective unit-dose amount.

20. The airless pump of claim 15, wherein the dispensing device is configured such that repeated actuations consistently and repeatedly dispense the effective unit-dose amount upon each actuation during treatment.

21. The airless pump of claim 15, wherein the dispensing device is pre-filled with a pre-fill amount corresponding to the treatment regimen such that repeated actuations of the dispensing device deliver a predefined number of single unit-dose amounts effective to treat the dermal and/or mucosal condition in accordance with the effective treatment regimen.

22. The airless pump of claim 15, wherein the dispensing device is configured such that a substantial portion of the imiquimod formulation drawn into the dispensing duct upon each actuation remains within the dispensing duct after actuation so that a uniform and consistent amount unit-dose of the imiquimod formulation is dispensed per each subsequent actuation.

23. The airless pump of claim 15, wherein the dispensing device is configured such that about 85% or more of the imiquimod formulation drawn into the dispensing duct upon each actuation remains within the dispensing duct after actuation so that a uniform and consistent amount unit-dose of the imiquimod formulation is dispensed per each subsequent actuation.

24. The airless pump of claim 15, wherein the dispensing device is configured such that an amount of the imiquimod formulation dispensed per one actuation is the same upon each subsequent actuation when actuating the dispensing device during treatment.

25. The airless pump of claim 15, wherein the dispensing device is configured so as to not be readily disassemblable by the patient so that a remaining amount of imiquimod formulation remaining with the dispensing duct after each actuation remains effective and to avoid exposing the patient to excess imiquimod formulation.

* * * * *